United States Patent [19]
Lowe et al.

[11] Patent Number: 5,807,732
[45] Date of Patent: Sep. 15, 1998

[54] GDP-L-FUCOSE: β-D-GALACTOSIDE 2-α-L-FUCOSYLTRANSFERASES, DNA SEQUENCES ENCODING THE SAME, METHOD FOR PRODUCING THE SAME AND A METHOD OF GENOTYPING A PERSON

[76] Inventors: John B. Lowe, 3125 Bolgos Cir., Ann Arbor, Mich. 48105; Gregory Lennon, 8309 Norris Canyon, Castro Valley, Calif. 94552; Sylvie Rouquier; Dominique Giorgi, both of 5, rue du Cannau, 34000 Montpellier, France; Robert J. Kelly, 3164 Concord, Trenton, Mich. 48183

[21] Appl. No.: 395,800

[22] Filed: Feb. 28, 1995

[51] Int. Cl.$^6$ .............................. C12N 5/00; C12N 1/20; C12N 15/00; C07H 21/04

[52] U.S. Cl. .................................. 435/240.2; 435/252.2; 435/252.3; 435/69.1; 435/320.1; 435/193; 536/23.2; 935/70

[58] Field of Search ................................... 435/193, 69.1, 435/70.3, 320.1, 240.2, 252.1, 252.8, 244.1, 252.2, 252.3; 536/23.2; 935/70

[56] References Cited

U.S. PATENT DOCUMENTS

| | | |
|---|---|---|
| 4,205,129 | 5/1980 | Podolsky et al. . |
| 4,411,994 | 10/1983 | Gilbert et al. . |
| 4,438,200 | 3/1984 | Taubman et al. . |
| 4,593,004 | 6/1986 | Boross et al. . |
| 4,634,665 | 1/1987 | Axel et al. . |
| 4,745,055 | 5/1988 | Schenk et al. . |
| 5,324,663 | 6/1994 | Lowe . |

FOREIGN PATENT DOCUMENTS

WO 90/13300  11/1990  WIPO .

OTHER PUBLICATIONS

Sarnesto et al. "Purification of the secretor–type beta–galactoside alpha1,2–fucosyltransferase from human serum" J. Biol. Chem. 267, 2737–2744, Feb. 5, 1992.

Piau et al. "Evidence for two distinct alpha(1,2)–fucosyltransferase gene differentially expressed throughout the rat colon" Biochem. J. 300, 623–626, 1994.

Kelly et al. "Sequence and expression of a candidate for the human secretor blood group alpha(1,2)fucosyltransferase gene (fut2)" J. Biol. Chem. 270, 4640–4649, Mar. 3, 1995.

Hitoshi et al. "Molecular coloning and expression of two types of rabbit beta–glactoside alpha1,2–fucosyltransferase" J. Biol. Chem. 270, 8844–8850, Apr. 14, 1995.

Masutani et al. "Purification and characterization of secretory–type–GDP–L–fucose:beta–D–galactoside 2–alpha–L–fucosyltransferase from human gastric mucosa" J. Biochem. 118, 541–545, 1995.

Lowe et al, FASEB Abstract Form, "Blood Group H α–2–L–Fucosyltransferase Expressed in Mouse Cells After Stable Transfection with Human DNA", (1988).

Kukowska–Latallo et al, (Sep. 22, 1988 Submission to UCLA Glycobiology Symposium).

Ernst et al, (Sep. 22, 1988 Submission to UCLA Glycobiology Symposium).

Lowe et al, (Sep. 22, 1988 Submission to UCLA Glycobiology Symposium).

Ernst et al, J. Biol. Chem., "Stable Expression of Blood Group H Determinants and GDP–L–fucose:β–D–Galactoside 2–α–L–Fucosyltransferase in Mouse Cells after Transfection with Human DNA", (1989) 264, pp. 3436–3447.

Rajan et al, J. Biol. Chem., "A Cloned Human DNA Restriction Fragment Determines Expression of GDP–L–Fucose:β–D–Galactoside 2–α–L–fucosyltransferase in Transfected Cells", (1989) 264, pp. 11158–11167.

Larsen et al, Proc. Natl. Acad. Sci., "Molecular Cloning, Sequence and Expression of a Human GDP–L–fucose:β–D–galactoside 2–α–L–fucosyltransferase cDNA that can Form the H Blood Group Antigen",(1990)87,pp. 6674–6678.

Larsen et al, Proc. Natl. Acad. Sci., "Isolation of a cDNA Encoding a Murine UDPgalactose:β–D–galactosyl–1, 4–N–acetyl–D–glucosaminide α–1,3–galactosyltransferase: Expression Cloning by Gene Transfer", (1989) 86, pp. 8227–8231.

Graham et al, Virology, "A New Technique for the Assay of Infectivity of Human Adenovirus 5 DNA", (1973) 52, pp. 456–467.

Kukowska–Latallo et al, Genes & Devel., "A Cloned Human cDNA determines expression of a Mouse Stage–Specific Embryonic Antigen and the Lewis Blood Group α(1,3/1, 4)fucosyltransferase", (1990) 4, pp. 1288–1303.

Weber et al, Mol. Cell. Biol., "Molecular Cloning and Biological Characterization of a Human Gene, ERCC2, That Corrects the Nucleotide Excision Repair Defect in CHO UV5 Cells", (1988) 8, pp. 1137–1146.

Ripka et al, Biochem. & Biophys. Res. Comm., "DNA–Mediated Transformation of N–Acetylglucosaminyl–transferase I Activity into an Enzyme Deficient Cell Line", (1989), 159, pp. 554–560.

Ripka et al, (preprint) "Co–transformation of Lec1 CHO Cells with N–Acetylgucosaminyltransferase I Activity and a Selectable Marker".

Chao et al, Science, "Gene Transfer and Molecular Cloning of the Human NGF Receptor", (1986), 232, pp. 518–521.

Kavathas et al, Proc. Natl. Acad. Sci., "Stable Transformation of Mouse L Cells for Human Membrane T–Cell Differentiation Antigens, HLA and $β_2$–microglobulin: Selection by Fluorescence–activated Cell Sorting", (1983), 80, pp. 524–528.

Southern et al, J. Mol. Appl. Genet., "Transformation of Mammalian Cells to Antibiotic Resistance with a Bacterial Gene Under Control of the SV40 Early Region Promoter", (1982), 1, pp. 327–341.

(List continued on next page.)

Primary Examiner—Robert A. Wax
Assistant Examiner—Nashaat T. Nashed
Attorney, Agent, or Firm—Oblon, Spivak, McClelland, Maier & Neustadt, P.C.

[57] ABSTRACT

The gene encoding GDP-L-fucose: β-D-Galactoside 2-α-L-fucosyltransferase has been cloned, and a mutation in this gene has been found to be responsible for an individual being a non-secretor.

12 Claims, 23 Drawing Sheets

OTHER PUBLICATIONS

Kuhn et al, *Cell,* "Gene Transfer, Expression, and Molecular Cloning of the Human Transferrin Receptor Gene", (1984), 37, pp. 95–103.

Wigler et al, *Cell,* "Biochemical Transfer of Single–Copy Eucaryotic Genes Using Total Cellular DNA as Donor", (1978), 14, pp. 725–731.

Littman et al, *Cell,* "The Isolation and Sequence of the Gene Encoding T8: A Molecule Defining Functional Classes of T Lymphocytes", (1985), 40, pp. 237–246.

Toone et al, *Tetrahedron Rep.,* (1989) "Enzyme–Catalyzed Synthesis of Carbohydrates" pp. 5365–5422.

Hodgson, *Bio/Techn.,* "Capitalizing in Carbohydrates", (1990), 8, pp. 83–111 (partial).

Stinson, *C&EN,* "Controlled Linkage Techniques for Monosaccharides Introduced", (1989), Aug. 28, 1989, pp. 25–26.

*C&EN,* "Yale Carbohydrate Technology Licensed", (1990), Jan. 15, 1990, pp. 7–8.

Shaper et al, *Proc. Natl. Acad. Sci.,* "Bovine Galactosyltransferase: Identification of a Clone by Direct Immunological Screening of a cDNA Expression Library", (1986), 83, pp. 1573–1577.

Appert et al, *Biochem. Biophys. Res. Comm.,* "Isolation of a cDNA Coding for Human Galactosyltransferase", (1986), 139, pp. 163–168.

Narimatsu et al, *Proc. Natl. Acad. Sci,* "Cloning and Sequencing of cDNA of Bovine N–acetylglucosamine ($\beta$1–4)galactosyltransferase", (1986), 83, 4720–4724.

Prieels et al, *J. Biol. Chem.,* "Purification of the Lewis Blood Group N–Acetylglucosaminide $\alpha$1–4 Fucosyltransferase and an N–Acetylglucosaminide $\alpha$1–3 Fucosyltransferase from Human Milk", (1981) 256, pp. 10456–10463.

Eppenberger–Castori et al, *Glycoconjugate J,* "Purification of the N–Acetylglucosaminide $\alpha$(1–3/4) Fucosyltransferase of Human Milk", (1989), 6, pp. 101–114.

Elices et al, *J. Biol. Chem.,* "Purification and Characterization of UDP–Gal:$\beta$–D–Gal(1,4)–D–GlcNAc $\alpha$(1,3)–Galactosyltransferase from Ehrlich Ascites Tumor Cells", (1986) 261, pp. 6064–6072.

Blanken et al, *J. Biol. Chem.,* "Biosynthesis of Terminal Gal$\alpha$1–3Gal$\beta$1–4GlcNAc–R Oligosaccharide Sequences on Glyconconjugates", (1985), 260, pp. 12927–12934.

Beyer et al, *J. Biol. Chem.,* "Purification to Homogeneity of the H Blood Group $\beta$–Galactoside $\alpha$1–2 Fucosyltransferase from Porcine Submaxillary Gland", (1980), 255, pp. 5364–5372.

Beyer et al, *J. Biol. Chem.,* "Enzymatic Properties of the $\beta$–Galactoside $\alpha$1–2 Fucosyltransferase from Porcine Submaxillary Gland", (1980), 255, pp. 5373–5379.

Weinstein et al, *J. Biol. Chem.,* "Primary Structure of $\beta$–Galactoside $\alpha$2,6–Sialyltransferase", (1987), 262, pp. 17735–17743.

Weinstein et al, *J. Biol. Chem.,* "Purification of a Gal$\beta$1–4GlcNAc $\alpha$2–6 Sialyltransferase and a Gal$\beta$1–3(4)GlcNAc $\alpha$2–3 Sialyltransferase to Homogeneity from Rate Liver", (1982), 250, pp. 13835–13844.

Creeger et al, *Meth. Enz.,* "Complex Carbohydrates", (1982), 83, pp. 326–331 (ed. V. Ginsborg).

Natsuka et al, *J. Biol. Chem.,* "Molecular Cloning of a cDNA Encoding a Novel Human Leukocyte $\alpha$–1,3–Fucosyltransferase Capable of Synthesising the Sialyl Lewis x Determinant", (1994), 269(24), pp. 16789–16794.

Natsuka et al, *J. Biol. Chem.,* (*Additions and Corrections*), "Molecular Cloning of a cDNA Encoding a Novel Human Leukocyte $\alpha$–1,3–Fucosyltransferase Capable of Synthesising the Sialyl Lewis x Determinant", (1994), 269(32), pp. 20806.

Sasaki et al, *J. Biol. Chem.,* "Expression Cloning of a Novel $\alpha$–1,3–Fucosyltransferase that is Involved in Biosynthesis of the Sialyl Lewis x Carbohydrate Determinant in Leukocytes", (1994), 269(20), pp. 14730–14737.

Sarnesto et al, *J. Biol. Chem.,* "Purification of the $\beta$–N–Acetylglucosaminide $\alpha$1–3–Fucosyltransferase from Human Serum", (1992),267, pp. 2745–2752.

Mollicone et al, *Eur. J. Biochem.,* "Acceptor Specificity and Tissue Distribution of Three Human $\alpha$–3–fucosyltransferases", (1990), 191, pp. 169–176.

Holmes et al, *J. Biol. Chem.,* "Biosynthesis of the Sialyl–Le$^x$ Determinant Carried by Type 2 Chain Glycosphingolipids (IV$^3$NeuAcIII$^3$FucnLe$_4$, VI$^3$NeuAcV$^3$FucnLc$_6$, and VI$^3$NeuAcIII$^3$V$^3$Fuc$_2$nLc$_6$) in Human Lung Carcinoma PC9 Cells", (1986), 261, pp. 3737–3743.

Weston et al, *J. Cell. Biochem,* "Defining a Glycosyltransferase Gene Family: Cloning and Expression of a Gene Encoding a GDP–Fucose: N–Acetylglucosaminide 3–$\alpha$–L–Fucosyltransferase Homologous to But Distinct from Known Human $\alpha$(1,3)Fucosyltransferases", (1992), p. 150.

Weston et al, *J. Biol. Chem.,* "Isolation of a Novel Human $\alpha$(1,3)Fucosyltransferase Gene and Molecular Comparison to the Human Lewis Blood Group $\alpha$(1,3/1,4)Fucosyltransferase Gene", (1992), 267, pp. 4152–4160.

Holmes et al, *J. Biol. Chem.,* "Enzymatic Basis for the Accumulation of Glycolipids with X and Dimeric X Determinants in Human Lung Cancer Cells (NCI–H69)", (1985), 260, pp. 7619–7627.

Weston et al, *J. Biol. Chem.,* "Molecular Cloning of a Fourth Member of a Human $\alpha$(1,3)Fucosyltransferase Gene Family", (1992), 267, pp. 24575–24585.

Koszdin et al, *Biochem. and Biophys. Res. Comm.,* "The Cloning and Expression of a Human $\alpha$–1,3 Fucosyltransferase Capable of Forming the E–Selectin Ligand", (1992), 187, pp. 152–157.

Nishihara et al, *Biochem. and Biophys. Res. Comm.,* "Human $\alpha$–1,3 Fucosyltransferase (FucT–VI) Gene is Located at Only 13 Kb 3' to the Lewis Type Fucosyltransferase (FucT–III) Gene on Chromosome 19", (1993), 190, pp. 42–46.

Mulligan et al, *J. Exp. Med.,* "Protective Effects of Sialylated Oligosaccharides in Immune Complex–induced Acute Lung Injury", (1993), 178, pp. 623–631.

Mulligan et al, *Nature,* "Protective Effects of Oligosaccharides in P–selectin–dependent Lung Injury", (1993), 364, pp. 149–151.

```
Sec1 AA 328 (a
             (b  - - - - - - L A - - - . . . . G Q   A G Q N G L *
             (c
Sec1 DNa 980 GCCTTCCTGCCAGAGTGGGTGGGCCTTGCGGCTGACCTT.........GGACAGGCTGGACAGAACGGCCTCTAGCCAGCCCTGACATGTGCCTGGTCCTCATCCTGTGACCCGAGGGC 1089
             |||||||||||||||||  ||  ||||  ||||||||             |||||||||||||     |||||   ||||||||||  |||||||||| |||||||||||||||||||| ||
H DNA   1030 GCCTTCCTGCCCGAGTGGGTGGGCATTAATGCAGACTGTCTCCACTCTGGACACTGCTAAGCCTTGAGAGCCAGGAGACTTCTGAAGTAGCCTGATCTTTCTAGAGCCAGCCAGTAC 1149
H AA     344 A F L P E W V G I N A D L S P L W T L A K P *

| Wild type probe | Phenotype | Mutant probe |
|---|---|---|
| ● | Cloned wild type allele | |
| | Cloned Trp 143 → ter allele | ● |
| ● | Secretor | ● |
| ● | Secretor | |
| | Non-secretor | ● |
| | Non-secretor | ● |
| | Non-secretor | ● |
| | Non-secretor | ● |
| | Non-secretor | ● |
| | Non-secretor | ● |

FIG. 11B

# GDP-L-FUCOSE: β-D-GALACTOSIDE 2-α-L-FUCOSYLTRANSFERASES, DNA SEQUENCES ENCODING THE SAME, METHOD FOR PRODUCING THE SAME AND A METHOD OF GENOTYPING A PERSON

This invention was made in part with Government support under Grant No. HL48859 awarded from the National Institute of Health and Grant No. W-7405-ENG-48 awarded from the Department of Energy. The U.S. government has certain rights in this invention.

BACKGROUND OF THE INVENTION

1. Field of the Invention

The present invention relates to novel GDP-L-fucose: β-D-Galactoside 2-α-L-fucosyltransferases, DNA which encodes such enzymes, plasmids which contain such DNA, transformed microorganisms which contain such plasmids, methods for procuding such enzymes, and a method for determining if a person is a secretor or nonsecretor.

2. Discussion of the Background

Mammalian cells display a complex variety of carbohydrate antigens on their surface. The structures of these carbohydrate moieties are determined largely by the glycosyltransferases responsible for oligosaccharide synthesis. The human H blood group oligosaccharide determinant serves as an essential precursor for the action of specific glycosyltransferases that construct the A and B blood group antigens (Watkins, W. M., *Adv. Hum. Genet.*, vol. 10, 1–116 (1980); Sadler, J. E., In "Biology of Carbohydrates", eds. Ginsburg, V. & Robbins, P. W. (Wiley, New-York) Vol. 2, pp 199–213 (1984); Kuijpers, T. W., Blood, vol. 81, 873–882 (1993)). The H gene locus (or FUT1) encodes an α(1,2) fucosyltransferase that catalyzes the synthesis of the H determinant via a transglycosylation reaction that transfers L-fucose from the substrate GDP-fucose to the β-D-galactose residue at the non-reducing terminus of glycoconjugates to form H-active Fucα(1,2)Gal-β-moieties. Genetic and biochemical studies indicate that the human genome encodes at least one other distinct α(1,2)fucosyltransferase activity, thought to be encoded by a second locus termed the Secretor blood group locus (Se or FUT2) (Oriol, R., Danilovs, J. and Hawkins, B. R., *Am. J. Hum. Genet.*, vol. 33, 421–431 (1981); Le Pendu, J., Cartron, J. P., Lemieux, R. U. and Oriol, R., *Am. J. Hum. Genet.*, vol. 37, 749–760 (1985); Kelly, R. J., Ernst, L. K., Larsen, R. D., Bryant, J. G., Robinson, J. S. and Lowe, J. B., *Proc. Natl. Acad. Sci. USA*, vol. 91, 5843–5847 (1994)). The Secretor locus-determined α(1,2)fucosyltransferase, like the H locus encoded enzyme, can also synthesize blood group H determinants. Experimental evidence also indicates that the H and Se loci express their cognate α(1,2)fucosyltransferases, as well as the corresponding cell surface and soluble H-active oligosaccharide products, in characteristic tissue-specific expression patterns (Oriol, R., Danilovs, J. and Hawkins, B. R., *Am. J. Hum. Genet.*, vol. 33, 421–431 (1981); Le Pendu, J., Cartron, J. P., Lemieux, R. U. and Oriol, R., *Am. J. Hum. Genet.*, vol. 37, 749–760 (1985); Kelly, R. J., Ernst, L. K., Larsen, R. D., Bryant, J. G., Robinson, J. S. and Lowe, J. B., *Proc. Natl. Acad. Sci. USA*, vol. 91, 5843–5847 (1994)). It has been shown, for example, that expression of the H locus is largely restricted to tissues derived from mesoderm (like erythrocyte progenitors) or ectoderm (epidermis) (reviewed in Oriol, R., *J. Immunogenet.*, vol. 17, 235–245 (1990)), whereas expression of the Se locus is apparently restricted to epithelia derived from embryonic endoderm, including those epithelial cells that line the stomach, intestine, and salivary glands (Oriol, R., Danilovs, J. and Hawkins, B. R., *Am. J. Hum. Genet.* vol. 33, 421–431 (1981); Le Pendu, J., Cartron, J. P., Lemieux, R. U. and Oriol, R., *Am. J. Hum. Genet.*, vol. 37, 749–760 (1985); Oriol, R., *J. Immunogenet.*, vol. 17, 235–245 (1990)).

Fucosyltransferases have often been used as genetic markers in linkage analyses. Indeed, the first human autosomal linkage group described was that of the ABH Secretor locus and the Lutheran blood group locus LU (Mohr, J., *Acta Path. Microbiol. Scand.*, vol. 28, 339–344 (1951)). Later work established that these loci lie on chromosome 19q (Eiberg, H., Mohr, J., Staub Nielsen, L. and Simonsen, N., *Clin. Genet.*, vol. 24, 159–170 (1983); Ball, S. P., Buckton, K. E., Corney, G., Fey, G., Monteiro, M., Noades, J. E., Pym, B., Robson, E. B. and Tippett, P., *Cytogenet. Cell Genet.*, vol. 37, 411 (1984); Whitehead, A. S., Solomon, E., Chambers, S., Bodmer, W. F., Povey, S. and Fey, G., *Proc. Natl. Acad. Sci. USA*, vol. 79, 5021–5025 (1982)). It was subsequently demonstrated that FUT1 and FUT2 are very closely linked (Oriol, R., Le Pendu, J., Bernez, L. Lambert, F., Dalix, A. M. and Hawkins, B. R., *Cytogenet. Cell. Genet.*, vol. 37, 564 (1984); Ball, S. P., Tongue, N., Gibaud, A., Le Pendu, J., Mollicone, R., Gerard, G. and Oriol, R., *Ann. Hum. Genet.*, vol. 55, 225–233 (1991)), suggesting that these genes may have evolved by gene duplication and subsequent divergence (Oriol, R., Danilovs, J. and Hawkins, B. R., *Am. J. Hum. Genet.*, vol. 33, 421–431 (1981)). To date, only the FUT1 gene-encoded α(1,2)fucosyltransferase has been cloned (Kelly, R. J., Ernst, L. K., Larsen, R. D., Bryant, J. G., Robinson, J. S. and Lowe, J. B., *Proc. Natl. Acad. Sci. USA*, vol. 91, 5843–5847 (1994); Larsen, R. D., Ernst, L. K., Nair, R. P. and Lowe, J. B., *Proc. Natl. Acad. Sci. USA*, vol. 87, 6674–6678 (1990)). Mapping studies using somatic cell hybrids have assigned FUT1 to chromosome 19 (Larsen, R. D., Ernst, L. K., Nair, R. P. and Lowe, J. B., *Proc. Natl. Acad. Sci. USA*, vol. 87, 6674–6678 (1990)). FUT1 has recently been localized to 19q13.3, distal to the APOE and APOC2 loci, using fluorescence in situ hybridization approaches (Rouquier, S. Giorgi, D., Bergmann, A., Brandriff, B. and Lennon, G., *Cytogenet. Cell Genet.*, vol. 66, 70–71 (1994)).

The ABO blood group antigens consist of oligosaccharides synthesized by the sequential action of glycosyltransferases. While these molecules were classically defined as polymorphic red cell antigens, subsequent studies demonstrated that soluble forms of these molecules may be found in the saliva, and in other secretions, in some, though not all humans (reviewed in Watkins, W. M., *Adv. Hum. Genet.*, vol. 10, 1–116 (1980); Sadler, J. E., In: *Biology of Carbohydrates* (Ginsburg, V., and Robbins, P. W., eds.), vol. 2, pp 199–213, Wiley, New York (1984), and Oriol, R., *J. Immunogenet.*, vol. 17, 235–245 (1990)). The ability to elaborate soluble A, B, and H antigens is determined by the Secretor blood group locus. Homozygosity for null alleles at this locus occurs in approximately 20% of most populations (Mourant, A. E., Kop èc, A. C., and Domaniewska-Sobczak, K., *The distribution of the human blood groups and other biochemical polymorphisms*, 2nd Ed., Oxford University Press, London. (1976)), and yield the non-Secretory phenotype, characterized by absence of normal amounts of soluble A, B, and H substance in the saliva (Watkins, W. M., *Adv. Hum. Genet.*, vol. 10, 1–116 (1980)). By contrast, most humans maintain the secretor phenotype, and elaborate soluble blood group substance in amounts easily detectable by standard hemagglutination-inhibition assays (Gaensslen, R. E., Bell, S. C., and Lee, H. C., *J. of Forensic Sciences*, vol. 32, 1016–1058 (1987); Milne, R. W., and Dawes, C., *Vox Sang.*, vol. 25, 298–307 (1973)). The penultimate step in the pathway leading to synthesis of soluble and membrane-associated A and B antigens is catalyzed by α(1,2) fucosyltransferases (Watkins, W. M., *Adv. Hum. Genet.*, vol. 10, 1–116 (1980); Sadler, J. E., In: *Biology of Carbohydrates* (Ginsburg, V., and Robbins, P. W., eds.), vol. 2, pp 199–213, Wiley, New York (1984); Oriol, R., *J. Immunogenet.*, vol. 17, 235–245 (1990)). These enzymes form a precursor oligosaccharide substrate (Fuc α(1,2)Galβ-) termed the H antigen, which is an essential substrate for the final step in the pathway, catalyzed by allelic glycosyltransferases encoded by the ABO locus (Watkins, W. M., *Adv. Hum. Genet.*, vol. 10, 1–116 (1980)). Genetic (Oriol, R., Danilovs, J. and Hawkins, B. R., *Am. J. Hum. Genet.*, vol. 33, 421–431 (1981); Larsen, R. D., Ernst, L. K., Nair, R. P. and Lowe, J. B., *Proc. Natl. Acad. Sci. USA*, vol. 87, 6674–6678 (1990); Kelly, R. J., Ernst, L. K., Larsen, R. D., Bryant, J. G., Robinson, J. S. and Lowe, J. B., *Proc. Natl. Acad. Sci. USA*, vol. 91, 5843–5847 (1994); Le Pendu, J., Cartron, J. P., Lemieux, R. U. and Oriol, R., *Am. J. Hum. Genet.*, vol. 37, 749–760 (1985)) and biochemical (Le Pendu, J., Cartron, J. P., Lemieux, R. U. and Oriol, R., *Am. J. Hum. Genet.*, vol. 37, 749–760 (1985); Kumazaki, T. and Yoshida, A., *Proc. Natl. Acad. Sci. USA*, vol. 81, 4193–4197 (1984), Sarnesto, A., Kohlin, T., Thurin, J., and Blaszczyk-Thurin, M., *J. Biol. Chem.*, vol. 265, 15067–15075 (1990); Sarnesto, A., Kohlin, T., Hindsgaul, O., Thurin, J., and Blaszczyk-Thurin, M., *J. Biol. Chem.*, vol. 267, 2737–2744 (1992)) analyses indicate that the H blood group locus represents an α(1,2) fucosyltransferase gene expressed in the erythroid lineage, and determines expression of the H antigen (along with A and/or B antigens) on red cells. By contrast, these studies are consistent with a hypothesis (Oriol, R., Danilovs, J. and Hawkins, B. R., *Am. J. Hum. Genet.*, vol. 33, 421–431 (1981)) that the Secretor locus corresponds to a closely linked but distinct α(1,2)fucosyltransferase gene whose expression is restricted to secretory epithelial cells in the salivary glands, gastrointestinal tract, and elsewhere, where it controls expression of soluble H antigen (and thus A or B antigen synthesis) in saliva and other secretions (reviewed in Oriol, R., *J. Immunogenet.*, vol. 17, 235–245 (1990)).

SUMMARY OF THE INVENTION

Accordingly, one object of this invention is to provide novel DNA sequences which encode an enzyme exhibiting the activity of transferring a fucose residue to a type II acceptor or a type I acceptor such that the fucose is linked in the alpha 1,2 configuration to the terminal galactose.

It is another object of the present invention to provide novel DNA sequences which encode novel GDP-L-fucose: β-D-Galactoside 2-α-L-fucosyltransferases.

It is another object of the present invention to provide plasmids or vectors which contain such a sequence of DNA.

It is another object of the present invention to provide cells transfected with such a plasmid or vector.

It is another object of the present invention to provide novel monoclonal antibodies which specifically bind to such enzymes.

It is another object of the present invention to provide novel immunoassays to detect and/or quantitate such enzymes.

It is another object of the present invention to provide a method for preparing such an enzyme by culturing a cell which has been transformed with such a vector or plasmid.

It is another object of the present invention to provide a method of genotyping an individual as a secretor or non-secretor.

These and other objects, which will become apparent during the following detailed description, have been achieved by the inventors' cloning and expression of a human GDP-L-fucose: β-D-Galactoside 2-α-L-fucosyltransferase and their discovery that a nonsense mutation in this enzyme is responsible for the non-secretor genotype.

Thus, the present inventors have isolated two human DNA segments that represent candidates for the Secretor α(1,2)fucosyltransferase locus because they cross hybridize with the H blood group α(1,2)fucosyltransferase gene, and are in close physical proximity to this locus on chromosome 19. One of these, termed Sec1, represents a pseudogene. The other sequence, termed Sec2, encodes a polypeptide of 332 amino acids in length (and an isoform that is longer by 11 NH2-terminal amino acids) that in turn functions as an α(1,2)fucosyltransferase with catalytic properties corresponding to those assigned previously to the Secretor locus-encoded α(1,2)fucosyltransferase. The inventors have found that each of six unrelated non-secretor individuals maintains homozygosity for an allele at this locus which contains an enzyme-inactivating translational termination codon corresponding to amino acid residue 143. Ten of 52 (19%) randomly chosen individuals were determined to be homozygous for the mutant allele, in close correspondence to the frequency of the non-secretor phenotype in most populations. These results confirm that this newly described α(1,2)fucosyltransferase gene is the FUT2 gene corresponding to the human Secretor blood group locus.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIGS. 8a and b shows a comparison between the DNA and derived protein sequences of the H blood group locus and the Sec1 sequence. The DNA and derived protein sequences for the Sec1 DNA segment and the H gene (Larsen, R. D., Ernst, L. K., Nair, R. P. and Lowe, J. B. *Proc. Natl. Acad. Sci. USA*, vol. 87, 6674–6678 (1990); Kelly, R. J., Ernst, L. K., Larsen, R. D., Bryant, J. G., Robinson, J. S. and Lowe, J. B. *Proc. Natl. Acad. Sci. USA*, vol. 91, 5843–5847 (1994)) are aligned to maximize DNA sequence identity using the GCG program Align (Devereux, J., Haeberli, P., and Smithies, O. *Nucl. Acids. Res.*, vol. 12, 387–395 (1984)). Amino acid sequence residue numbers are indicated at the left and right of the sequence listings. Nucleotide sequences are numbered in a similar manner, assigning the A residue of the translation initiation codon as position number 1. Nucleotide sequence identity is denoted by a vertical line between the two sequences. Dots (.) denote gaps introduced to maximize sequence identity between the DNA or protein sequences. The derived protein sequences are displayed above (for Sec1) or below (for H) the corresponding DNA sequence. The reading frame used to predict maximally-similar Sec1-derived amino acid sequence is indicated at left by "a", "b", or "c". Amino acid residues within the Sec1-derived protein sequence that are identical to corresponding residues in the H α(1,2)fucosyltransferase sequence are indicated by a dash (-) in the Sec1-derived amino acid sequence. Amino acid residues within putative membrane-spanning hydrophobic segments in each amino acid sequence are doubly underlined. A methionine codon that yields an open reading frame with amino acid sequence similarity to the H α(1,2)fucosyltransferase is singly underlined, as is the initiator methionine in the H α(1,2) fucosyltransferase. Potential asparagine-linked glycosylation sites are indicated by dotted underlining. The frameshift and non-sense "mutations" that must be conceptually suppressed to maintain amino acid sequence similarity between the protein sequence predicted by the Sec1 DNA sequence are indicated above that sequence;

DETAILED DESCRIPTION OF THE PREFERRED EMBODIMENTS

Figure 9E:
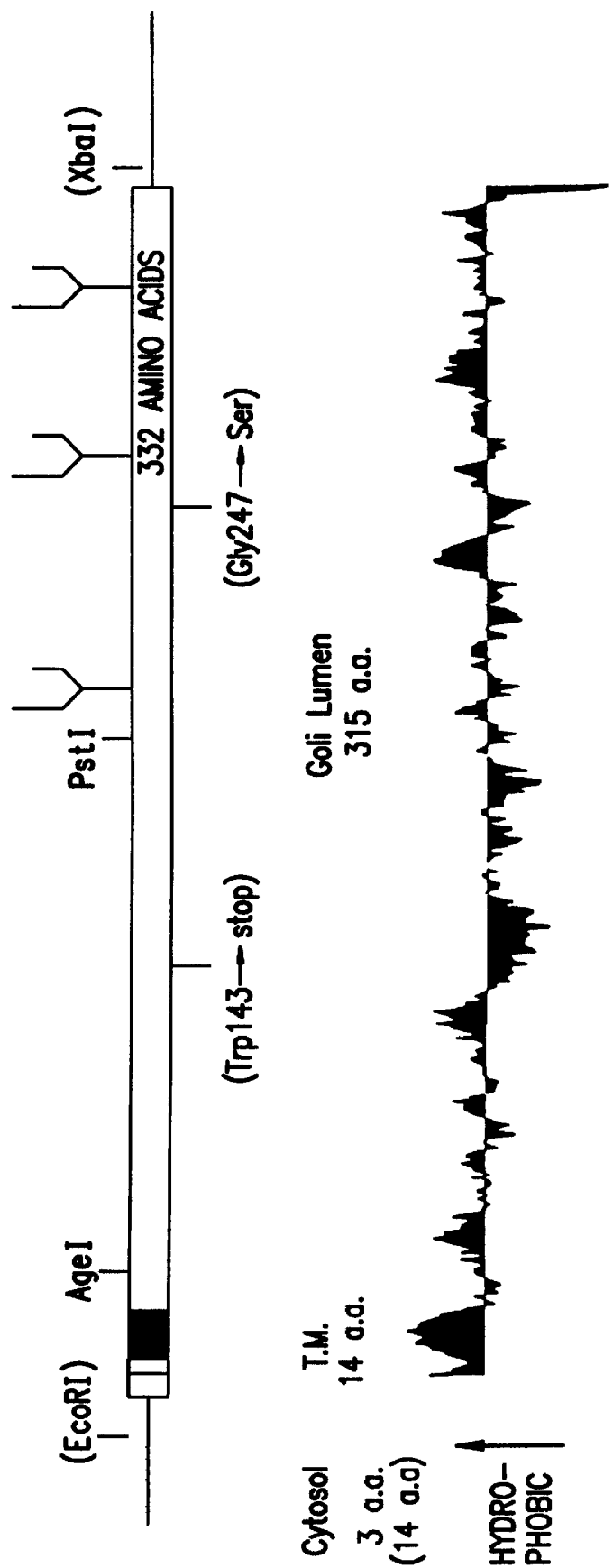
FIGS. 9a, b and c show the sequence and predicted structure of the enzyme encoded by Sec2. The DNA sequence for Sec2 is SEQ ID No: 7 in the Sequence Listing, and the amino acid sequence for Sec2 is SEQ ID No: 8 in the Sequence Listing. Nucleotide position –96 in FIG. 9a corresponds to nucleotide position 1 in SEQ ID NO: 7, and amino acid position –11 in FIG. 9a corresponds to amino acid position 1 in SEQ ID NO: 8. (a) Comparison between the DNA and derived protein sequences of the H blood group locus and the Sec2 sequence. The DNA and derived protein sequences for the Sec2 and H genes are aligned to maximize DNA sequence identity, using the GCG program Align (Devereux, J., Haeberli, P., and Smithies, O. Nucl. Acids. Res., vol. 12, 387–395 (1984)). Amino acid sequence residue numbers are indicated at the left and right of the sequence listings. Nucleotide sequences are numbered in a similar manner, assigning the A residue of the translation initiation codon of the shortest predicted polypeptide (indicated by the downward pointing arrow) as position number 1. Nucleotide sequence corresponding to codon sequence is displayed by capital letters, whereas sequence predicted to correspond to non-translated regions is denoted by lower case letters. Nucleotide sequence identity is denoted by a vertical line between the two sequences. Gaps introduced to maximize sequence identity between the DNA sequences are indicated by dotted lines. The derived protein sequences are displayed above (for Sec2) or below (for H) the corresponding DNA sequence. Amino acid residues within the Sec2-derived sequence that are identical to corresponding residues in the H α(1,2)fucosyltransferase sequence are indicated by the "." symbol above the Sec2-encoded residue. Amino acid residues within putative membrane-spanning hydrophobic segments in each protein are doubly underlined. The methionine codon that may initiate the longest of two potential Sec2-encoded polypeptides is singly underlined, as is the initiator codon for the H gene. This predicted protein is 11 amino acid residues longer (indicated in lower case letters) than the shorter Sec2-encoded α(1,2)fucosyltransferase. The (second) methionine codon tentatively assigned as an initiator codon for this latter protein is singly underlined, and the corresponding methionine residue is indicated by an arrow. Potential asparagine-linked glycosylation sites are indicated by dotted underlining. The polymorphic DNA sequence residues that either inactivate the enzyme (Trp143→ter), or that are functionally neutral (Gly247→Ser), are underlined ("wild type" nucleotide sequence is shown). The corresponding amino acid residue is indicated in bold type. The sequence of the alternative allele, and its corresponding protein sequence change, are indicated above these positions. Protein sequence-neutral DNA sequence polymorphisms are also indicated ("wild type" nucleotide sequence is shown). The sequence of the alternative allele is indicated above these positions. The singly underlined section of the Sec2 sequence 3' to the coding region corresponds exactly to the DNA sequence of the partial cDNA derived from this locus; (b) Schematic diagram of the α(1,2)fucosyltransferase encoded by the Sec2 sequence. Proposed domain structure, above, and hydropathy plot (Kyte, J., and Doolittle, R. F. *J. Mol. Biol.*, vol. 157, 105–132 (1982)), below, for the 332 amino acid polypeptide predicted by the Sec2 DNA sequence. The relative positions of the potential asparagine-linked glycosylation sites (Ψ), the inactivating non-sense mutation (Trp143→stop), and transmembrane segment (■), are indicated on the rectangular schematic representation of the fucosyltransferase. Hydrophobic regions within the predicted protein are indicated by the shading above the horizontal axis of the hydropathy plot. The predicted intracellular locations of the NH$_2$-terminal (Cytosol), hydrophobic transmembrane (T.M.), and catalytic (Golgi Lumen) domains are indicated with their amino acid lengths. The potential 11 amino acid long NH2-terminal extension is indicated by the dotted rectangle appended to the shorter Sec2-encoded α(1,2)fucosyltransferase. The positions of the AgeI and PstI restriction sites, and synthetic (see Materials and Methods) AgeI and EcoRI sites (in parentheses) used to create various expression vectors are also displayed.

Thus, in a first embodiment, the present invention provides novel DNA sequences which encode novel GDP-L-fucose: β-D-Galactoside 2-α-L-fucosyltransferases. Suitably, the present DNA sequence is any which encodes the amino acid sequence shown for Sec2 in FIG. 9a. More preferably, the DNA sequence is any which encodes a protein having the sequence corresponding to from position 18 to position 332 in the amino acid sequence shown for Sec2 in FIG. 9a.

Of course, the DNA sequence may encode a protein which corresponds to any of those described above but in which up to 17 amino terminal amino acid residues have been added, deleted, or substituted, provided that the protein retains its activity. In this context a protein is considered to retain its activity if it retains at least 10%, preferably at least ⅓, more preferably at least ½ of the specific activity of the native enzyme to transfer fucose to the acceptors phenyl-β-D-galactoside, or lacto-N-biose I, or N-acetyllactosamine as determined by the assay described in the Examples.

In a preferred embodiment, the DNA sequence has the nucleotide sequence shown for Sec2 in FIG. 9a. More preferably, the DNA sequence has the nucleotide sequence corresponding to from position 52 to position 1066 in the nucleotide sequence shown for sec2 in FIG. 9a.

The cloning of the full length DNA sequence shown as Sec2 in FIG. 9a is described in great detail in the Examples below. The shorter length fragments of this sequence as well as the other DNA sequences of the present invention may be obtained by conventional techniques, such as solid state DNA synthesis, site-directed mutagenesis, or the polymerase chain reaction (Maniatis, T., et al, *Molecular Clon-* ing: *A Laboratory Manual*, Cold Spring Harbor Laboratory Press, Cold Spring Harbor, N.Y. (1989)).

In another embodiment, the present invention provides novel GDP-L-fucose: β-D-Galactoside 2-α-L-fucosyltransferases. Suitably, the enzyme has the amino acid sequence shown as Sec2 in FIG. 9a. Alternatively, the enzyme has an amino acid sequence corresponding to from position 18 to position 332 in the amino acid sequence shown as Sec2 in FIG. 9a. As discussed above, the enzyme may also have one of the amino acid sequences described above and in which up to 17 amino terminal amino acid residues have been added, deleted, or substituted.

The present invention also provides novel fusion proteins in which any of the enzymes of the present invention are fused to a polypeptide such as protein A, streptavidin, fragments of c-myc, maltose binding protein, IgG, IgM, amino acid tag, etc. Preferably, the polypeptide fused to the present invention is fused to the amino terminus of the present enzyme. In addition, it is preferred that the polypeptide fused to the enzyme of the present invention is chosen to facilitate the release of the fusion protein from a prokaryotic cell into the culture medium.

In yet another embodiment, the present invention provides novel plasmids or vectors which contain a DNA sequence according to the present invention. The present plasmid may be either a cloning vector or an expression plasmid. Suitable plasmids or vectors are those obtained by inserting a DNA sequence of the present invention into a plasmid or vector such as pCDM8 pCDNA1, pREP8, pCEP4, pTZ18, etc. In the case of an expression plasmid, the DNA sequence of the present invention is preferably inserted into the plasmid downstream from a promoter and in the correct reading frame. The insertion of a DNA sequence according to the present invention into any conventional expression plasmid in the correct reading frame and the insertion of a DNA sequence of the present invention into a conventional cloning vector can easily be accomplished by the skilled artisan using conventional recombinant DNA technology.

The present invention also provides transformed cells which contain a plasmid or vector according to the present invention. Suitable host cells include any mammalian cell. Preferred host cells include Chinese hamster cells, COS cells, etc. The transformation of such host cells with a plasmid or vector according to the present invention may be carried out using conventional techniques (Maniatis, T., et al, *Molecular Cloning: A Laboratory Manual*, Cold Spring Harbor Laboratory Press, Cold Spring Harbor, N.Y. (1989); and Conzelmann, A., et al, *J. Exp. Med.*, vol. 167, pp. 119–131 (1988)).

In another embodiment, the present invention provides a method for producing an enzyme of the present invention by culturing in a culture medium a transformed cell according to the present invention for a time sufficient to produce the enzyme. Preferably, the cell has been transformed with an expression plasmid such as pCDM8-CT, pCDNAI-α(1,2)FT Se-short. Of course, the particular culture conditions, such as temperature, medium, etc., will depend on the type and identity of the transformed cell. However, the selection of appropriate conditions is well within the abilities of the skilled artisan. For example, suitable culture conditions and media for a variety of cell types are taught in Maniatis, T., et al, *Molecular Cloning: A Laboratory Manual*, Cold Spring Harbor Laboratory Press, Cold Spring Harbor, N.Y. (1989), which is incorporated herein by reference.

In another embodiment, the present invention provides novel monoclonal antibodies which specifically bind to the present enzymes. Such monoclonal antibodies may be produced using conventional methods such as described in Harlow, et al, *Antibodies. A Laboratory Manual*, Cold Spring Harbor Laboratory Press, Cold Spring Harbor, N.Y. (1988), which is incorporated herein by reference. The present antibodies may be labelled with any conventional label, such as a radiolabel, a chromophore (e.g., a fluorescent label), or an enzyme (e.g., horseradish peroxidase).

The present invention also provides novel immunoassays for the detection and/or quantitation of the present enzymes in a sample. The present immunoassays will utilize one or more of the present monoclonal antibodies which specifically bind to the present enzymes. The present immunoassay may be a competitive assay, a sandwich assay, or a displacement assay, such as those described in Harlow, et al, *Antibodies. A Laboratory Manual*, Cold Spring Harbor Laboratory Press, Cold Spring Harbor, N.Y. (1988) and Ausebel, F. M., et al, *Current Protocols in Molecular Biology*, John Wiley and Sons, NY (1989) and may rely on the signal generated by a radiolabel, a chromophore, or an enzyme.

Figure 11A:
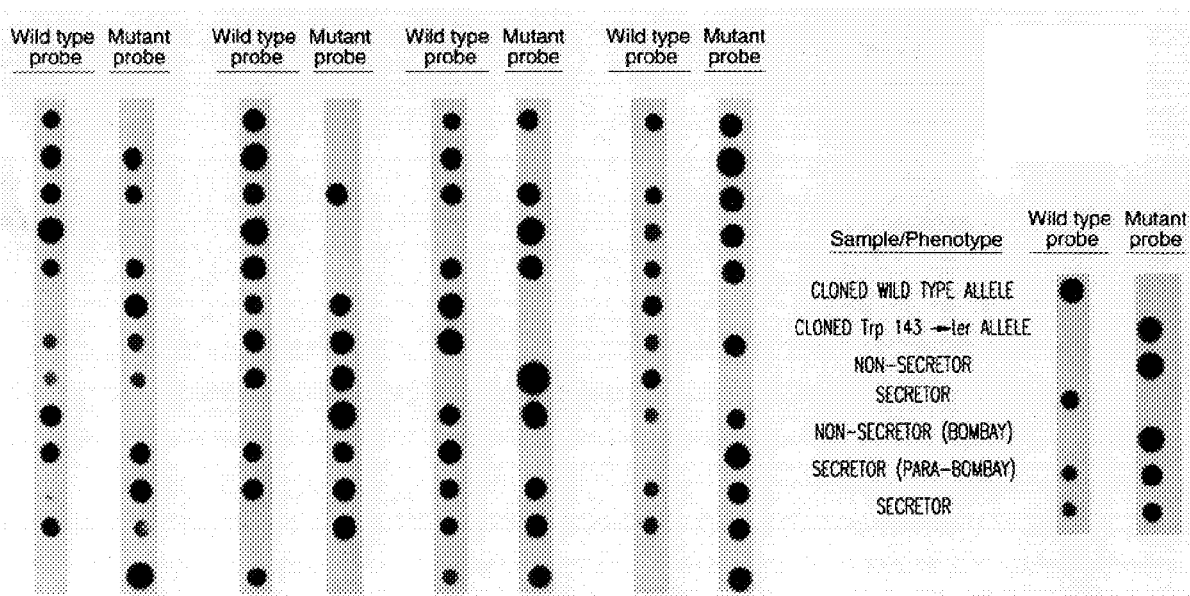
FIGS. 11a and b show the results of allele-specific oligonucleotide (ASO) hybridization analysis of the Trp143→ter codon polymorphism. (a) ASO analysis of 52 random individuals, and 8 control samples. A DNA segment encompassing the polymorphic site was amplified from genomic DNA obtained from each of 52 randomly sampled individuals and probed with a radiolabeled oligonucleotide corresponding to the Trp143 allele ("wild-type probe"), or with a radiolabeled oligonucleotide corresponding to the ter143 allele ("mutant probe"), using reagents and conditions described in "Materials and Methods". Results obtained with control samples derived from cloned versions of each allele, or from individuals with known phenotypes, are displayed in the boxed area at right. (b) ASO analysis of six non-secretor individuals, two secretor individuals, and cloned control samples, using reagents and procedures identical to those used in FIG. 11a, above.

In another embodiment, the present invention provides a method for genotyping an individual as either a secretor or a non-secretor. In particular, the present method involves determining whether the individual's DNA encodes the present GDP-L-fucose: β-D-Galactoside 2-α-L-fucosyltransferase (secretor) or contains the nonsense mutation Trp143→ter (non-secretor). The present method may be carried out by obtaining a tissue sample from the individual (preferred tissues include hair folicles, blood cells, skin cells, buccal epithelial cells, semen, tears, or any tissue obtained by rinsing a body cavity), and isolating the DNA from the tissue using standard methods. The isolated DNA is then assayed for the presence of the Trp143→ter allele, using standard methods such as those described in FIGS. 11a and b and in Maniatis, T., et al, *Molecular Cloning: A Laboratory Manual*, Cold Spring Harbor Laboratory Press, Cold Spring Harbor, N.Y. (1989).

This invention is a heretofore undiscovered DNA sequence that encodes a specific (and heretofore undiscovered) protein sequence capable of functioning as a GDP-L-fucose: β-D-Galactoside 2-α-L-fucosyltransferase. This enzyme, when expressed by the cloned DNA sequence described here, has been shown to function within mammalian cells to generate de novo expression of specific cell surface glycoconjugate structures on those cells. These structures are recognized by an antibody against the blood group H antigen (structure Fuc α(1,2)[Gal(β1,3/4)]GlcNAc). This enzyme, when expressed by the cloned DNA sequence described here, has also been shown to function in the enzymatic manner implied in its name, when assayed in extracts prepared from cells that express the DNA sequence. The oligosaccharide product of this enzyme represents fucose linked in alpha 1,2 configuration to the terminal galactose in a "type II" acceptor or to a "type I" acceptor. Throughout the remainder of this disclosure, these products will be referred to as terminal α(1,2)fucose residues. The catalytic domain of this enzyme has also been localized by inference to experiments done with a structurally similar enzyme, the blood group H GDP-L-fucose: β-D-Galactoside 2-α-L-fucosyltransferase. The enzymatic properties of the enzyme encoded by this cDNA, and chromosomal localization studies, indicate that this cDNA is the product of the human Secretor blood group locus.

The utilities of the present DNA, enzyme and tranformed cells include:

i. Construction of animal cell lines with specific capabilities with respect to post-translational modification of the oligosaccharides on cell-surface, intracellular, or secreted proteins or lipids by terminal α(1,2)fucose residues that represent the products of this enzyme (for the production of diagnostics and therapeutics by the biotechnology industry).

Specifically, the cloned DNA sequence described here may be introduced by standard technologies into a mammalian cell line that does not normally express the cognate enzyme or its product (terminal α(1,2)fucose residues on oligosaccharides), and transcribed in that cell in the "sense" direction, to yield a cell line capable of expressing terminal α(1,2)fucose residues on oligosaccharides on cell-surface, intracellular, or secreted proteins or lipids. Alternatively, this cloned DNA sequence may be introduced by standard technologies into a mammalian cell line that does express the cognate enzyme and its product (terminal α(1,2)fucose residues), and transcribed in that cell in the "anti-sense" direction, to yield a cell line incapable of expressing terminal α(1,2)fucose residues on cell-surface, intracellular, or secreted proteins or lipids. Alternatively, the endogenous GDP-L-fucose: β-D-Galactoside 2-α-L-fucosyltransferase gene(s), in a mammalian cell expressing the cognate enzyme (s), might be inactivated with the DNA sequence described here by homologous recombination techniques, or by "antisense" oligonucleotide approaches based upon the DNA sequence described herein, or by dominant negative mutant fucosyltransferase sequences that inactivate endogenous GDP-L-fucose: β-D-Galactoside 2-α-L-fucosyltransferase (s) and that may be derived via mutagenesis and genetic selection schemes, in conjunction with the present sequence information.

This method may be used to construct animal cell lines, or transgenic animals, that will be suitable host cells for the production of diagnostic or therapeutic materials whose usefulness or efficacy depends upon the specific post-translational modification determined by this cloned DNA sequence and its cognate enzyme. For example, it is known that the biological effectiveness of many therapeutic proteins or peptides, recombinant or otherwise, may depend critically upon the oligosaccharide structure(s) that are covalently attached to them. The structure of these oligosaccharides is primarily a function of the number and kind of glycosyltransferase enzymes that are found in the cell used to produce these therapeutic products. Animal cells and yeasts are competent to perform these glycosylation reactions; however, not all glycosyltransferase enzymes are produced by every animal cell or yeast, and therefore, some oligosaccharide structures (including terminal α(1,2)fucose residues generated by the enzyme encoded by the DNA sequence described here) are not produced by them. The converse is also true, namely, that producing cells may express a glycosyltransferase analagous to, or identical to, the GDP-L-fucose: β-D-Galactoside 2-α-L-fucosyltransferase encoded by the present DNA sequence. It is likely that terminal α(1,2)fucose residues may alter the bioactivity (for better or for worse) of natural or recombinant therapeutic or diagnostic agents (oligosaccharides, glycoproteins or glycolipids) produced by mammalian or other eukaryotic hosts. Eukaryotic host cells that the biotechnology industry uses to produce these recombinant agents may be altered with the present DNA sequence information, to add terminal α(1,2)fucose residues to the oligosaccharides on recombinant products by expressing all or part of the cloned sequences described here in the desired host. Alternatively, terminal α(1,2)fucose residues may be eliminated from the product produced in these host cells by the use of transfected "anti-sense" vector constructs, recombination-based gene inactivation, "anti-sense" oligonucleotide approaches, or dominant negative mutant fucosyltransferases, outlined above.

The old "methods" used for this process include an empirical approach to identify a cell line that does or does not express this particular enzyme or an enzyme that functions in a similar or identical manner, for the production of the appropriately modified recombinant or natural product. This is not always optimal since cell lines with this particular post-translation modification capabilities may not exist naturally, or may not be especially suited to high level production of an appropriately modified product. Alternatively, unwanted terminal α(1,2)fucose residues present on a therapeutic material produced by an empirically identified animal cell line must be removed chemically or enzymatically, a process that may be costly or inefficient. The advantages of using the present cloned, functional DNA sequence in conjunction with the technologies outlined above, relative to these older methods, include the ability to construct lines that specifically lack the capability to generate terminal α(1,2)fucose residues on the oligosaccharides of glycoproteins and glycolipids; properly constructed, these cell lines will eliminate any need for chemical or enzymatic treatment of a therapeutic or diagnostic material to remove unwanted terminal α(1,2)fucose residues. Moreover, in the event that terminal α(1,2)fucose residues residues are found to be desireable for a particular diagnostic or therapeutic product produced by animal cells, cell lines may be engineered with the cloned DNA sequence described here to generate these residues.

ii. Isolation of reagents suitable for efficient enzymatic synthesis and production of oligosaccharides (in enzyme reactors, for example).

Oligosaccharides may have therapeutic utility as immunomodulatory reagents in the field of organ transplantation. In particular, soluble and solid-phase oligosaccharides may find use as therapeutic agents with which to block or ameliorate antibody-mediated organ transplant rejection in cases involving incompatibility due to differences in the major blood group antigen systems of the organ donor and the recipient, including the Lews blood group system. Likewise, soluble oligosaccharides may find use as therapeutic agents that function by blocking attachment of bacterial, viral, or parasitic pathogens to glycoconjugate "receptors" found on the surface of the animal tissues that these pathogens invade. For example there is evidence that portions of the Lewis b blood group oligosaccharide antigen (containing terminal α(1,2)fucose residues) serve as "receptors" for some forms of uropathogenic bacteria. Another important association between terminal α(1,2)fucose residues and bacterial pathogens concerns the observation that non-secretors (who are genetically deficient in the gene disclosed here) maintain an increased relative risk (1.5-fold) for duodenal ulcers. This observation is especially interesting in the context of recent work demonstrating that the bacterial organism *Helicobactor pylori* can attach to gastric epithelium via type I H and Lewis b oligosaccharide determinants, whose expression in gastrointestinal tissues is determined by the Secretor locus, or by Secretor and Lewis blood group loci, respectively. Since colonization of the gastrointestinal tract by this organism in humans has been associated with histologic gastritis, gastric lymphoma, gastric carcinoma, gastric ulcer, and recurrence of duodenal ulcers, it is possible that Secretor locus-dependent expression of soluble H-active and Lewis b-active glycoconjugates in the gastrointestinal tract prevents (or allows) *Helicobactor pylori* colonization, and indirectly determines susceptibility to the gastrointestinal diseases noted above. These observations also suggest that oligosaccharides (like type I H and Lewis b oligosaccharide determinants) constructed by a recombinant form of the Secretor locus-encoded GDP-L-fucose: β-D-Galactoside 2-α-L-fucosyltransferase described here might be used as therapeutic agents that block *Helicobactor pylori* attachment to gastric epithelium, and thus prevent histologic gastritis, gastric lymphoma, gastric carcinoma, gastric ulcer, and recurrent duodenal ulcers.

Glycoconjugates, including terminal α(1,2)fucose residues, have also been implicated in modulating adhesive events between cells, and between cells and their environment during developmental and differentiation processes. These events included binding of spermatozoa to eggs, and the initial events that mediate attachment of fertilized ova to the uterine wall at the beginning of implanatation. These observations suggest, for example, the possibility of contraceptive uses for (biologically "natural") oligosaccharide molecules.

Currently, oligosaccharides containing terminal α(1,2) fucose residues are produced by chemical synthesis (a procedure that is inefficient and costly) or by isolation from natural sources (using costly and inefficient procedures that often require the processing of large quantities of animal or plant material, and the purification of the desired oligosaccharide from other contaminating oligosaccharides). The present invention provides a mechanism to synthesize abundant quantities of purified GDP-L-fucose: β-D-Galactoside 2-α-L-fucosyltransferase. This could be used to construct an enzyme bioreactor (enzyme in solution or immobilized on a solid phase matrix, for example via the protein-A moiety fused to the catalytic domain of the enzyme capable of enzymatic synthesis of structures containing terminal α(1, 2)fucose residues. This may be more efficient than approaches involving chemical synthesis of structures containing terminal α(1,2)fucose residues or their purification from natural sources, for a variety of reasons. One, the only chemicals necessary would be the enzyme substrates; these are easily obtained or synthesized. Two, enzymatic synthesis of such structures will produce only the desired product and the nucleotide diphosphate product of substrate hydrolysis. This latter chemical is found as the natural by-products of these reactions in animal cells, is relatively non-toxic, and may be easily separated from the oligosaccharide synthetic product. By contrast, chemical synthetic procedures typically generate numerous products of side reactions which must be removed, and which may be toxic as well. Similarly, purification of oligosaccharides from natural sources requires the removal of other contaminating oligosaccharides present in the natural material. Three, enzymatic catalysis is extraordinarily efficient; nearly complete conversion of substrate to product might be achieved. By contrast, chemical synthesis of terminal α(1,2)fucose residues on oligosaccharides is a multi-step process; yields at each step may be much less than 100%, and the cumulative efficiency of current chemical synthesis procedures does not approach the efficiency possible with enzymatic synthesis. Similarly, purification of oligosaccharides with terminal α(1,2)fucose residues from natural materials can entail significant losses inherent to the purification procedures required to separate the desired oligosaccharide from contaminating, irrelevant oligosaccharides, with inefficient isolation of the desired oligosaccharide. Although the GDP-L-fucose: β-D-Galactoside 2-α-L-fucosyltransferase encoded by the present DNA sequence may be purified from animal tissues for synthetic use, these purifications are themselves inefficient, primarily because the enzyme is typically present in very low abundance. The present invention provides two mechanisms that may provide for the abundant production of this enzyme. First, this may be done through the construction and selection of animal cells that produce relatively large quantities of the enzymes. Alternatively, this cloned nucleic acid sequences may then be used with standard recombinant DNA technologies to produce large quantities of glycosyltransferases in yeasts or in prokaryotic hosts. Furthermore, the sequence encoding this enzyme may be modified via standard molecular cloning schemes or mutagenesis to yield a recombinant fucosyltransferase with novel properties that make it more desirable than the wild-type enzyme. For example, the modifications might be made to the enzyme that make it more stable, or more suitable for immobilization in a bioreactor.

iii. Isolation of reagents suitable for producing recombinant GDP-L-fucose: β-D-Galactoside 2-α-L-fucosyltransferase to be used directly as a research reagent, or to be used to generate antibodies against the GDP-L-fucose: β-D-Galactoside 2-α-L-fucosyltransferase, for research applications.

The present invention provides two mechanisms for producing large quantities of this enzyme (see ii. above—i.e. specially constructed animal cells, or via natural or synthetic genes encoding these enzymes) which may be used as a research tool with which to study the structures and functions of oligosaccharides and glycoproteins. Likewise, the enzyme produced by this method, or the nucleic acid sequence and derived protein sequence provided by this method, may be used to generate antibodies to this enzyme (via synthetic peptides). These antibodies may be used as research reagents to study the biosynthesis and processing of these enzymes, and may be used as an aid in their purification for all the uses described in this disclosure.

iv. Antibodies to glycosyltransferases as diagnostic reagents.

Aberrant expression of GDP-L-fucose: β-D-Galactoside 2-α-L-fucosyltransferase has been associated with malignancy in humans, suggesting that this enzyme might serve as a tumor marker for early detection of malignancy involving a number of human tissues. Enzyme tumor markers have typically been assayed in body fluids by activity assays, which may be subject to non-specificity due to competing glycosyltransferase activity. These assays may also be insensitive since it is possible that inactive enzymes might be useful as tumor markers but would not be detected by enzyme activity assays.

The present invention provides a mechanism for generating antibodies to this enzyme (monoclonal and polyclonal antibodies against synthetic peptides constructed from information derived from cloned DNA sequence encoding GDP-L-fucose: β-D-Galactoside 2-α-L-fucosyltransferase, or against the recombinant enzyme produced by eukaryotic or prokaryotic hosts). Antibodies specific for this GDP-L-fucose: β-D-Galactoside 2-α-L-fucosyltransferase may be used to detect and quantitate this glycosyltransferases in body fluids, with specificity and sensitivity exceeding enzyme activity assays, and serving as a tumor marker for early detection of malignancy.

v. Recombinant enzyme for use in screening natural and synthetic compounds for fucosyltransferase inhibitors or inactivators.

There may be an association between increased numbers of cell surface terminal α(1,2)fucose residues on oligosaccharides of a cell and the ability of that cell to metastasize in a malignant fashion. Thus, drugs that inhibit the enzyme encoded by the present DNA sequence may be used as anti-tumor agents. The present reagents may be used for screening compounds for anti-fucosyltransferase activity, since the cloned sequence may be used with standard techniques to produce relatively large amounts of pure fucosyltransferase. This will aid in screening since the effects of potential inhibitors will be tested on a pure enzyme, without the confounding effects that may occur in whole cell extracts or with partially purified enzyme.

vi. Engineering of glycosyltransferase substrate specificity to generate novel glycoconjugate structures on secreted or cell-associated glycoconjugates.

The present invention provides a reagent (a cloned GDP-L-fucose: β-D-Galactoside 2-α-L-fucosyltransferase cDNA) and the genetic selection method used to isolate it, that, when used with appropriate mutagenesis schemes, may allow the generation of mutant GDP-L-fucose: β-D-Galactoside 2-α-L-fucosyltransferases that generate glycosidic linkages different from that generated by the wild-type enzyme. These novel linkages may or may not be naturally occuring, and may be used to enhance bioactivity of the molecules to which they are attached. Alternatively, mutagenesis and selection approaches may be used to generate mutant GDP-L-fucose: β-D-Galactoside 2-α-L-fucosyltransferases that act in a dominant negative fashion. The dominant negative mutants so generated might be used to inactivate endogenous glycosyltransferase activities when the product(s) of such an enzyme are not desired. Mutant GDP-L-fucose: β-D-Galactoside 2-α-L-fucosyltransferases might also be generated, for example, that function as fucosidases that hydrolyze various sugar linkages (fucose, mannose, or others) from oligosaccharides in vivo and in vitro. The latter capability may be used in an enzyme bioreactor.

vii. Genotyping individuals at the Se locus.

The present data indicate that many, and perhaps most, or even all, human non-secretors, maintain this phenotype because of an enzyme inactivating point mutation in the coding region of the gene disclosed here. Detection of this mutation is technically straightforward using contemporary molecular methods, and can lead to an unambiguous determination of an individual's geneotype, and thus phenotype, at the Se locus. This is in contrast to current methods for determining Secretor status (involving hemagglutination inhibition assays that detect secreted blood group substances in human saliva), which can be rather imprecise, can yield false negatives resulting in misassignment of secretor status, and cannot unambiguously determine the genotype of an individual at this locus. The sequence information disclosed here, and the identification of a common inactivating mutation at this locus, allow, and facilitate determination of an individual's genotype, and phenotype, at the Se locus. Since such information can have utility in forensic and paternity circumstances, the present sequence and polymorphisms of the kind reported herein, in conjunction with standard DNA genotyping procedures, may find utility in forensic and paternity circumstances, as well as in organ transplanation procedures, or as a measure of succeptibility to infections caused by pathogens that may use blood group structures as receptors for invasion (as in urinary tract infections, for example).

Other features of the invention will become apparent in the course of the following descriptions of exemplary embodiments which are given for illustration of the invention and are not intended to be limiting thereof.

EXAMPLES

MATERIALS AND METHODS:

cDNA, cosmid, YAC and BAC Probes.

The FUT1 coding sequence probe was a PCR product of the FUT1 cDNA from position 1 to 1133 (Larsen, R. D., Ernst, L. K., Nair, R. P. and Lowe, J. B., *Proc. Natl. Acad. Sci. USA*, vol. 87, 6674–6678 (1990)) subcloned in plasmid pTZ (Pharmacia). Fifty ng of the gel purified PCR product were labeled by random-priming to a specific activity of $>10^8$ cpm/µg, according to (Feinberg, A. P. and Vogelstein, B., *Anal. Biochem.*, vol. 132, 6–15 (1983)). Cosmid insert probes were prepared as described (Rouquier, S., Giorgi, D., Trask, B., Bergmann, A., Phillips, M. S., MacLennan, D. H., and de Jong, P., *Genomics*, vol. 17, 330–340 (1993)). YAC and BAC probes were generated by Alu-PCR. For the YACs, primers PDJ33, PDJ34 and PDJ66 (Aslanidis, C. and de Jong, P. J., *Proc. Natln. Acad. Sci. USA*, vol. 88, 6765–6769 (1991), Shutler, G., Korneluk, R. G., Tsilfidis, C., Mahadevan, M., Bailly, J., Smeets, H., Jansen, G., Wieringa, B., Lohman, F., Aslanidis, C. and de Jong, P. J., Genomics, vol. 13, 518–525 (1992)) were used independently or in combination, two by two as described (Rouquier, S., Giorgi, D., Trask, B., Bergmann, A., Phillips, M. S., MacLennan, D. H., and de Jong, P., *Genomics*, vol. 17, 330–340 (1993)). BAC probes were generated from 150 ng of an alkaline lysis minipreparation by single primer Alu-PCR as described above except that primers ALE 1 and ALE 3 (Cole, C. G., Goodfellow, P. N., Bobrow, M. and Bentley, D. R., *Genomics*, vol. 10, 816–826 (1991)) were also used. Labelling of the PCR products was performed as described (Rouquier, S., Giorgi, D., Trask, B., Bergmann, A., Phillips, M. S., MacLennan, D. H., and de Jong, P., *Genomics*, vol.17, 330–340 (1993)).

Chromosome 19 cosmid library screening.

Two cosmid libraries (F and R) were generated from human chromosome 19 (de Jong, P. J., Yokobata, K., Chen, C., Lohman, F., Pederson, L., McNinch, J and Van Dilla, M., *Cytogenet. Cell. Genet.*, vol. 51, 985 (1989)) flow-sorted from the Chinese hamster-human hybrid cell line (5HL9-5B). This hybrid contains a chromosome 19 as its only human material (Siciliano, M. J., Carrano, A. V. and Thompson, L. H., *Mutat. Res.*, vol. 174, 303–308 (1986)). The libraries were constructed in the cosmid vectors Lawrist 5 (library F) (de Jong, P. J., Yokobata, K., Chen, C., Lohman, F., Pederson, L., McNinch, J and Van Dilla, M., *Cytogenet. Cell. Genet.*, vol. 51, 985 (1989)) or Lawrist 16 (library R), that are modifications of the LORIST series of vectors originally described in (Gibson, T. J., Coulson, A. R., Sulston, J. E. and Little, P. F. R., *Gene*, vol. 53, 275–281 (1987)). These vectors contain a double cos site, two unique SfiI sites and bacteriophage promoters (T7 and SP6 for the F library or T7 and T3 for the R library) flanking the insert. A total of about 19,100 individual clones, corresponding approximately to an eight-fold coverage of chromosome 19, were arrayed in microtiter dishes and spotted in high density arrays onto Nylon membranes (Hybond N) using a Beckman Biomek 1000 workstation (1536 clones/membrane) (Olsen, A. S., Combs, J., Garcia, E., Elliot, J., Amemiya, C., de Jong, P., Threadgill, G., *Biotechniques*, vol. 14, 116–117 (1993)). Filter hybridizations were performed in duplicate according to standard procedures (Sambrook, J., Fritsch, E. F. and Maniatis, T., "Molecular cloning, A Laboratory Manual", 2nd Ed, Cold Spring Harbor Laboratory Press, Cold Spring Harbor, N.Y. (1989)) with a labeled probe concentration of $10^6$ cpm/ml. For suppression of repetitive sequences, the probes were prehybridized in the presence of sheared human placental DNA as described (Pontarotti, P., Chimini, G., Boretto, J. and Jordan, B. R., *Nucl. Acids Res.*, vol. 16, 6767–6777 (1988)). Following hybridization, filters were briefly washed in 2× SSC, 0.1% SDS at room temperature; once in 2× SSC, 0.1% SDS at 65° C. (30 min); and once in 0.1× SSC, 0.1% SDS at 65° C. (30 min). For low stringency hybridizations used to detect imperfectly homologous sequences within the same species, filters were washed using low stringency conditions (rinsed in 2× SSC, 0.1% SDS at room temperature, followed by one 30 min wash in 2× SSC, 0.1% SDS at 50° C.).

YAC and BAC library screening.

High density filters containing 18,000 clones from the Imperial Cancer Research Fund (ICRF) YAC library (Larin, Z., Monaco, A. P. and Lehrach, H., *Proc. Natl. Acad. Sci. USA*, vol. 88, 4123–4127 (1991)) were processed for colony hybridization as described in (Brownstein B. H., Silverman, G. A., Little, R. D., Burke, D. T., Korsmeyer, S. J., Schlessinger, D. and Olson, M. V., *Science*, vol. 244, 1348–1351 (1989)). The filters were washed as described above for the cosmid filters. High density filters containing 15,000 clones from the California Institute of Technology (Pasadena, Calif.) BAC library (Shizuya, H., Birren, B., Kim, U-J., Mancino, V., Slepak, T, Tachiiri, Y. and Simon, M., *Proc. Natl. Acad. Sci. USA*, vol. 89, 8794–8797 (1992)) were hybridized according to standard procedures (Sambrook, J., Fritsch, E. F. and Maniatis, T., "Molecular cloning, A Laboratory Manual", 2nd Ed, Cold Spring Harbor Laboratory Press, Cold Spring Harbor, N.Y. (1989)).

Cosmid, YAC and BAC DNA preparation.

Cosmid DNA samples were isolated from cultures of 5 ml LB medium (Sambrook, J., Fritsch, E. F. and Maniatis, T., "Molecular cloning, A Laboratory Manual", 2nd Ed, Cold Spring Harbor Laboratory Press, Cold Spring Harbor, N.Y. (1989)) containing 20 µg/ml of kanamycin, by alkaline lysis and purification on Qiagen tip-20 columns, following the procedure recommended by the manufacturer (Qiagen, Inc. Chatsworth, Calif.). Yeast DNA was isolated in 100 µl agarose blocks as described (Rouquier, S., Giorgi, D., Trask, B., Bergmann, A., Phillips, M. S., MacLennan, D. H., and de Jong, P., *Genomics*, vol. 17, 330–340 (1993)). BAC DNA was isolated from 5 ml LB broth medium cultures containing 12.5 µg/ml of chloramphenicol by a standard alkaline lysis procedure (Birnboim, H. C., and Doly, J., *Nuc. Acids Res.*, vol. 7, 1513 (1979)).

Cosmid clone analysis. contig assembly and restriction mapping.

Assessment of contig integrity, contig size, cosmid overlap and fine EcoRI mapping was carried out either by total restriction enzyme digestion, or by partial digestion followed by Southern blot analysis (Sambrook, J., Fritsch, E. F. and Maniatis, T., "Molecular cloning, A Laboratory Manual", 2nd Ed, Cold Spring Harbor Laboratory Press, Cold Spring Harbor, N.Y. (1989)) of selected cosmids. For total digestion, cosmid DNAs were single-digested with SfiI, EcoRI or PstI, or double-digested with EcoRI-SfiI and EcoRI-PstI. Restriction digests were fractionated by electrophoresis through 0.4% and 1.2% agarose gels. The size of each cosmid was then determined by summing the sizes of restriction fragments visualized on the gels under ultraviolet irradiation after ethidium bromide staining. The gels were alkali blotted as described (Gemmill, R. M., Coyle-Morris, J. F., McPeek, F. D., JR,. Ware-Uribe, L. F. and Hecht, F., *Gene Anal. Techn.*, vol. 4, 119–131 (1987)) onto nylon membrane (Gene Screen Plus, DuPont) and used for hybridization as described in "cosmid screening". For partial digests, 6 µg of each cosmid were first digested to completion with SfiI to excise the insert from the Lawrist vector. The buffer was then adjusted to 50 mM NaCl and 100 mM Tris pH 7.5 to be compatible with EcoRI, and two series of four 15 µl aliquots, each containing 0.5 µg of the Sfi I digest, were partially digested using 0, 0.05, 0.15 and 0.5 unit of EcoRI for 45 min at 37° C. followed by an incubation at 68° C. for 10 min to inactivate the enzyme. These samples, and complete SfiI-EcoRI digests, were fractionated through a 0.4% agarose gel in 0.5× TBE for 20 h at 30 volts. The gels were blotted as described above, and hybridized separately for 12 h at 37° C. with 10 pmoles of $^{32}$P-ATP end labeled (Sambrook, J., Fritsch, E. F. and Maniatis, T., "Molecular cloning, A Laboratory Manual", 2nd Ed, Cold Spring Harbor Laboratory Press, Cold Spring Harbor, N.Y. (1989)) oligonucleotides (T3 and T7, for the R clones; Sp6 and T7 for the F clones), in 6× SSC, 5× Denhardt's solution, 0.05% sodium pyrophosphate, 0.1% SDS. The filters were then subjected to two, 1 hour 37° C. washes, in the same buffer without Denhardt's solution. The positions of the EcoRI sites relative to both vector-insert junctions were deduced from the autoradiograms by measuring the sizes of the successive partial EcoRI fragments hybridizing at one end with the radioactive T3, T7 or Sp6 primers. Similarly, the PstI restriction map of the 18.10 kb EcoRI fragment from cosmid 16240 was established by digesting cosmid DNA to completion with EcoRI, followed by a PstI partial restriction, and hybridization with labeled Sp6 primer. To determine the size of the cosmid contig, and to establish the extent of overlaps between cosmids, each cosmid was digested completely with EcoRI, and was subjected to Southern blot analysis with the SfiI insert of each cosmid. This allowed the determination of which EcoRI fragments are unique to each cosmid, which are shared by adjacent cosmids, and which correspond to vector/insert junction fragments.

YAC and BAC clone analysis.

Undigested YAC clones were analyzed by Pulsed Field Gel Electrophoresis (PFGE) using a contour-clamped homogeneous electric field apparatus (CHEF; Bio-Rad DRII) as described (Rouquier, S., Giorgi, D., Trask, B., Bergmann, A., Phillips, M. S., MacLennan, D. H., and de Jong, P., *Genomics*, vol. 17, 330–340 (1993)). After ethidium bromide staining, gels were destained in water for 30 minutes prior to alkali blotting on nylon membranes (Gene Screen plus, DuPont). For restriction analysis, 100 µl YAC blocks were enzyme-digested and analyzed as described (Rouquier, S., Giorgi, D., Trask, B., Bergmann, A., Phillips, M. S., MacLennan, D. H., and de Jong, P., *Genomics*, vol. 17, 330–340 (1993)). We isolated the YAC ends by an inverse PCR method described in (Rouquier, S., Giorgi, D., Trask, B., Bergmann, A., Phillips, M. S., MacLennan, D. H., and de Jong, P., *Genomics*, vol. 17, 330–340 (1993); Joslyn, G., Carlson, M., Thliveris, A., Albertsen, H., Gelbert, L., Samowitz, W., Groden, J., Stevens, J., Spirio, L., Robertsen, M., Sargent, L., Krapcho, K., Wolff, E., Burt, R., Hughes, J. P., Warrington, J., McPherson, J., Wasmuth, J., Le Paslier, D., Abderrahim, H., Cohen, D., Leppert, M. and White, R., *Cell*, vol. 66, 601–613 (1991)), using two sets of restriction endonucleases (set 1: Sau3AI, TaqI or HaeIII; set 2; AluI, HhaI or HaeIII), each set pertaining to one end of the YAC vectors. Yeast DNA was digested, ligated and amplified by PCR to obtain human sequence from each end of the YAC, using two primer sets: YAK5-U and YAK5-R for the left arm (set 1 ligated DNA), YAK3-U and YAK3-R for the right arm (set 2 ligated DNA), and PCR conditions described in (Joslyn, G., Carlson, M., Thliveris, A., Albertsen, H., Gelbert, L., Samowitz, W., Groden, J., Stevens, J., Spirio, L., Robertsen, M., Sargent, L., Krapcho, K., Wolff, E., Burt, R., Hughes, J. P., Warrington, J., McPherson, J., Wasmuth, J., Le Paslier, D., Abderrahim, H., Cohen, D., Leppert, M. and White, R., *Cell*, vol. 66, 601–613 (1991)). PCR fragments corresponding to the amplified YAC ends were isolated by agarose gel electrophoresis, labeled by random priming, and used as probes.

Insert BAC DNA was separated from the vector by a NotI digestion (BRL). Separation of the digested DNA was carried out by PFGE on a Bio-Rad CHEF Mapper apparatus for 20 h, at a field strength of 6 V/cm in a 1% agarose gel in 0.5× TBE, at 16° C., with a linear pulse from 5 to 15 sec. After ethidium bromide staining, the gel was alkali blotted as described above. cDNA selection using magnetic bead capture ("hybrid selection").

cDNA sequences were isolated using a modified procedure of the hybrid selection method described in (Parimoo, S., Patanjali, S. R., Shukla, H., Chaplin, D. D. and Weissman, S. M. *Proc. Natl. Acad. Sci. USA*, vol. 88, 9623–9627 (1991); Lovett, M., Kere, J. and Hinton, L. *Proc. Natl. Acad. Sci. USA*, vol. 88, 9628–9632 (1991); Morgan, J. G., Dolganov, G. M., Robbins, S. E., Hinton, L. M. and Lovett, M. *Nuc. Acids Res.*, vol, 20, 5173–5179 (1992); Korn, B., Sedlacek, Zdenek, Manca, A., Kioschis, P., Konecki, D., Lehrach, H. and Poustka, A. *Human Molec. Genet.*, vol. 1, 235–242 (1992); Tagle, D. A., Swaroop, M., Lovett, M. and Collins, F. *Nature*, vol. 361, 751–753 (1993)), using magnetic beads (Dynabeads M-280, Dynal, Oslo). Double-stranded cDNA was synthesized from 200 ng of polyadenylated human fetal brain RNA (Clontech, Palo Alto, Calif.), blunt-ended with T4 DNA polymerase. A UNI-Amp adaptor was then ligated to both ends of 2 ng of the cDNA molecules (UNI-Amp Plus kit, Clontech). The UNI-Amp primer was used to amplify ¼ of the ligation reaction. One tenth of this first amplification was submitted to a second PCR reaction with the same primer. One $\mu$g of this double-amplified cDNA was prehybridized overnight with 5 $\mu$g of Cot1 DNA, to block human repetitive sequences within the cDNA, and then hybridized for 24 h with 100 ng of biotinylated cosmid DNA (BioNick, BRL), following hybridization conditions recommended by the manufacturer (Dynal). After hybridization, cosmid-cDNA hybrids were separated from unbound cDNA using streptavidin coated magnetic beads. The biotin-streptavidin reaction, the washes to remove unspecifically bound cDNA, and the elution of specific cDNAs were performed as described in (Morgan, J. G., Dolganov, G. M., Robbins, S. E., Hinton, L. M. and Lovett, M., *Nuc. Acids Res.*, vol. 20, 5173–5179 (1992)). The eluate was then desalted by chromatography over a Sephadex G-50 (Pharmacia) spin column. For secondary cycles of enrichment, approximately 1 $\mu$g of amplified, eluted cDNA was recycled through the above process, including the repeat blocking step. After the second round of enrichment, the eluted cDNAs were amplified again by PCR and subcloned directly in the TA vector (Invitrogen). The recombinant clones were analyzed by PCR. All the PCR reactions were performed with UNI-Amp primer for 35 cycles, following the conditions of the manufacturer (Clontech). Specificity for cDNA origin of hybrid selected products was confirmed using the UNI-Amp primer and cosmid DNA (instead of cDNA) template.

Northern and genomic Southern blot analysis.

Samples of human colon, small intestine, kidney, and liver were obtained through an agreement with the Cooperative Human Tissue Network (Columbus, Ohio). Total RNA was prepared from these tissues by guanidine isothiocyanate lysis and cesium chloride gradient ultracentrifugation procedures (Sambrook, J., Fritsch, E. F. and Maniatis, T., "Molecular cloning, A Laboratory Manual", 2nd Ed, Cold Spring Harbor Laboratory Press, Cold Spring Harbor, N.Y. (1989)). Polyadenylated mRNA was prepared by two rounds of oligo dT cellulose affinity chromatography (Sambrook, J., Fritsch, E. F. and Maniatis, T., "Molecular cloning, A Laboratory Manual", 2nd Ed, Cold Spring Harbor Laboratory Press, Cold Spring Harbor, N.Y. (1989)). Five micrograms of polyadenylated mRNA from each tissue were fractionated through MOPS-buffered agarose gels, transferred to nylon hybridization membranes, and hybridized with radiolabeled DNA fragments, using procedures for Northern blotting described elsewhere (Kelly, R. J., Ernst, L. K., Larsen, R. D., Bryant, J. G., Robinson, J. S. and Lowe, J. B., *Proc. Natl. Acad. Sci. USA*, vol. 91, 5843–5847 (1994), Sambrook, J., Fritsch, E. F. and Maniatis, T., "Molecular cloning, A Laboratory Manual", 2nd Ed, Cold Spring Harbor Laboratory Press, Cold Spring Harbor, N.Y. (1989), Smith, D. F. Larsen, R. D., Mattox, S., Lowe, J. B. and Cummings, R. D., *J. Biol. Chem.*, vol. 265, 6225–6234 (1990)). After hybridization, blots were rinsed in 2× SSC, 0.1% SDS at room temperature, were then washed for 30 minutes at 65° C. in 0.2× SSC, 0.1% SDS, and were subjected to autoradiography. EcoRI digested genomic DNA (10 $\mu$g per lane) was subjected to Southern blot analysis as described (Sambrook, J., Fritsch, E. F. and Maniatis, T., "Molecular cloning, A Laboratory Manual", 2nd Ed, Cold Spring Harbor Laboratory Press, Cold Spring Harbor, N.Y. (1989), Smith, D. F. Larsen, R. D., Mattox, S., Lowe, J. B. and Cummings, R. D., *J. Biol. Chem.*, vol. 265, 6225–6234 (1990)).

DNA sequence analysis.

The cDNA insert in a TA cloning vector (PCRII, Invitrogen) was sequenced by the method of Sanger et al. (Sanger, F., Nicklen, S. and Coulson, A. R., *Proc. Natl. Acad. Sci. USA*, vol. 74, 5463–5467 (1977)) using the T7 DNA polymerase kit (Pharmacia) and M13 forward and reverse primers and 17-mer oligonucleotide primers synthesized according to the sequence of the cDNA insert. The 8.2 kb and 18.5 kb EcoRI fragments of cosmid 31553 were digested with PstI. The 1.1 kb EcoRI-PstI and 1.3 kb PstI-PstI fragments that cross-hybridized with the FUT1 cDNA probe were subcloned in Bluescript KS+ (Stratagene) and sequenced.

Fluorescence in situ hybridization.

Cosmids 27513 and 31553 were localized to chromosome bands by fluorescence in situ hybridization (FISH) analysis to metaphase chromosome spreads as previously described (Trask, B., Christensen, M., Fertitta, A., Bergmann, A., Ashworth, L., Branscomb, E., Carrano, A. and van den Engh, G., *Genomics*, vol. 14, 162–167 (1992), Schweizer D., *Chromosoma*, vol. 58, 307–324 (1976), Tucker, J. D., Christensen, M. L., Carrano, A. V., *Cytogen Cell Genet.*, vol. 48, 103–106 (1988)). Two-color fluorescence in situ hybridization was performed to map these cosmids relative to each other or relative to other chromosome 19 cosmids whose localization to chromosome bands has been previously reported (Trask, B. J., Fertitta, A., Christensen, M., Tynan, K., Youngblom, J., Bergmann, A., Copeland, A., de Jong, P., Mohrenweiser, H., Olsen, A. and Carrano, A. V., *Genomics*, vol. 15, 133–145 (1993)). With this approach, markers must lie at least ~1Mb (megabasepairs) apart for their order to be determined (Lawrence, J. B., Singer, R. H. and McNeil, J. A., *Science*, vol. 249, 928–932 (1990)). These cosmids were chosen from 19q13.2–13.3 to 19q13.3–13.4 and include 10384, 16236, 18618, 15743, 19556, 16957, 20019, 18887 (Trask, B. J., Fertitta, A., Christensen, M., Tynan, K., Youngblom, J., Bergmann, A., Copeland, A., de Jong, P., Mohrenweiser, H., Olsen, A. and Carrano, A. V., *Genomics*, vol. 15, 133–145 (1993), Trask, B. J., Massa, H. F., Kenwrick, S. and Gitschier, J., *Am. J. Hum. Genet.*, vol.48, 1–15 (1991)). The physical distance between cosmids 27513 and 31553 was measured in interphase chromatin, in 200 randomly selected interphase nuclei, as an estimate of the distance between them on the linear DNA molecule (Trask, B. J., Pinkel, D. and van den Engh, G. J., *Genomics*, vol. 5, 710–717 (1989), van den Engh, G. J., Sachs, R. and Trask, B. J., Science, vol. 257, 1410–1412 (1992)). Chromosomal assignment of YAC clones was done using Alu-PCR products as probes (Lengauer, C., Green, E. D. and Cremer, T., *Genomics*, vol. 13, 826–828 (1992)). Two hundred ng of each biotinylated PCR product were blocked for repetitive sequences with human Cot1 DNA (BRL) (Lengauer, C., Green, E. D. and Cremer, T., *Genomics*, vol. 13, 826–828 (1992)), and then hybridized to metaphase chromosome spreads as described above. The slides were labeled with fluoresceinconjugated detection reagents and the YAC PCR products were mapped as described above.

Molecular cloning and sequencing of the Sec1 and Sec2 DNA segments

Cosmid 31553 was mapped using a 1.3 kb probe made from the coding region of the human H blood group α(1,2) fucosyltransferase gene (Larsen, R. D., Ernst, L. K., Nair, R. P. and Lowe, J. B., *Proc. Natl. Acad. Sci. USA*, vol. 87, 6674–6678 (1990), Kelly, R. J., Ernst, L. K., Larsen, R. D., Bryant, J. G., Robinson, J. S. and Lowe, J. B., *Proc. Natl. Acad. Sci. USA*, vol. 91, 5843–5847 (1994)) (FUT 1). Two sequences related to FUT 1, termed Sec1 and Sec2 (Secretor candidates 1 and 2), were identified in this cosmid. The Sec1 sequence is contained within an 8.2 kb EcoRI fragment that cross-hybridizes with the H α(1,2)fucosyltransferase coding region probe. This 8.2 kb fragment was subcloned into the EcoRI site of the mammalian expression vector pcDNAI (Invitrogen), to create the vector pcDNAI-Sec1. Approximately 3.0 kb of this 8.2 kb fragment, representing the cross hybridizing portion of this fragment, was subjected to DNA sequencing by the dideoxy chain termination method (Sanger, F., Nicklen, S., and Coulson, A. R., *Proc. Natl. Acad. Sci. USA*, vol. 74, 5463–5467 (1977)) using T7 DNA polymerase (Sequenase, Amersham Life Sciences, Inc.). Both strands were sequenced using oligonucleotide primers corresponding to the insert sequence. The Sec2 sequence is contained within an 18.5 kb EcoRI restriction fragment of the cosmid that cross-hybridizes with the H α(1,2) fucosyltransferase coding region probe. Four cross-hybridizing and co-linear PstI fragments were subcloned into the PstI site of pTZ19R (Pharmacia LKB Biotechnology, Inc.) and their sequence determined. Direct sequencing of the cosmid was also performed to verify restriction fragment junctions.

Molecular cloning and sequencing of two alleles at the Sec2 locus

Preliminary sequence analysis of the Sec2 allele within cosmid 31553 suggested that a nonsense codon at codon 143 might be an alternative to a tryptophan codon in a potential functional, wild type allele, by way of comparison to the H α(1,2)fucosyltransferase DNA and protein sequence at this position. This analysis predicted that a putative wild type allele at this position would maintain an intact BstNI cleavage site (CCTGG), whereas this restriction site would not exist at this position in the putative Trp143→ter null allele (CCTGA) within the cosmid sequence. Preliminary analysis of a secretor-positive individual indicated that he was heterozygous for the BstI restriction site at this position. The coding regions of both alleles were therefore cloned at the Sec2 locus from this individual, using the PCR (Saiki, R. K., Scharf, S., Faloona, F., Mullis, K. B., Horn, G. T., Erlich, H. A., and Arnheim, N., *Science*, vol. 230, 1370–1374 (1985)) and primers that flank the codon corresponding to the Trp143→ter polymorphism. Each primer contains 30 bp derived from the Sec2 DNA sequence (below, underlined) and 10 bp that contains a restriction site (EcoRI, GAATTC; XbaI, TCTAGA) to facilitate subcloning. One primer pair amplifies the DNA sequence between base pairs −216 and −187 (GCGCGAATTCTATAAACACACTTGAGATA-CATGCCTGTGC; Sec2 sequence underlined), 5' to the "short" initiation codon, and between base pairs 535 and 564 (GCGCTCTAGAATGGACCCCTACAAAGGTGCCCGG CCGGCT; Sec2 sequence underlined) within the putative coding region of Sec2, and 3' to the polymorphic DNA sequence corresponding to codon 143. The second primer pair amplifies the DNA sequence between base pairs 369 and 398 (GCGCGAATTCGAGGAATACCGCCACATCC CGGGGGAGTAC; Sec2 sequence underlined) of the coding sequence, at a position 5' to the polymorphic site, and between base pairs 1049 and 1088 (GCGCTCTAGAGAACCATGTGCTTCTCATGCCCGGG CACTC; Sec2 sequence underlined), 50 base pairs 3' to the termination codon. Genomic DNA isolated (Ausubel, J., and Frederick, M., *Molecular Biology-Laboratory Manuals*, vols. 1 and 2, John Wiley and Sons, New York (1987)) from this secretor-positive individual was subjected to 30 cycles of PCR amplification (denaturation at 94° C. for 1.5 min, annealing/extension for 2.5 min at 72° C.). Fragments generated with these primers were restricted with EcoRI and XbaI, gel purified, and cloned into EcoRI/XbaI-cleaved pTZ19R. Clones corresponding to the putative wild type allele, and the putative Trp143→ter allele, were distinguished by restriction digestion with BstNI. The DNA sequences of a representative number of fragments from each allele were determined (Sanger, F., Nicklen, S., and Coulson, A. R., *Proc. Natl. Acad. Sci. USA*, vol. 74, 5463–5467 (1977)). Both strands were sequenced using oligonucleotide primers corresponding to the insert sequence. Multiple clones corresponding to each allele were sequenced to distinguish PCR errors from actual sequence polymorphisms.

Expression vector construction and analysis

For expression of Sec1, the vector pcDNAI-Sec1 (described above), was used and a related vector (pcDNAI-Sec1-rev) containing the identical 8.2 kb EcoRI fragment of Sec1 but cloned in the opposite orientation in pcDNAI. For the expression of the Sec2 allele in cosmid 31553, the PCR and cosmid 31553 template DNA were used to construct an expression vector (pcDNAI-α(1,2)FTse) with an insert encompassing the coding sequence of Sec2. The pair of PCR primers used amplifies the Sec2 sequence from a position bounded by base pair −15 and base pair 15 (assigning the A of the initiation codon, highlighted in bold type, as position 1; GCGCGAATTCCCTTTCTCCTTTCCCATG-GCCCACTTCATC; Sec2 sequence underlined), to a position bounded by base pair 1000 and 1029, immediately 3' to the stop codon at base pairs 997–999 (GCGCTCTAGAGGAGAAAAGGTCTCAAAGGACGG GCCAGCA; Sec2 sequence underlined). PCR conditions were used that minimize PCR-mediated DNA sequence alterations (Weston, B. W., Smith, P. L., Kelly, R. J., and Lowe, J. B., *J. Biol.Chem.*, vol. 267, 24575–24584 (1992)). The product from this amplification was restricted with EcoRI and XbaI, gel purified and ligated into EcoRI-XbaI-doubly digested pcDNAI. Clones with a single insert in the correct orientation were subjected to DNA sequence analysis to identify one without PCR-mediated DNA sequence alterations; one such clone was termed pcDNAI-α(1,2)FTse. Other expression vectors containing single or multiple DNA sequence polymorphisms were assembled with restriction fragment exchange procedures (Ausubel, J., and Frederick, M., *Molecular Biology-Laboratory Manuals*, Vols. 1 and 2, John Wiley and Sons, New York (1987)) using restriction sites within pcDNAI-α(1,2)FTSe. The vector pcDNAI-α(1,2)FTSe-int, containing the wild type sequence corresponding to codon 143 (TGG; Trp) along with wild type protein sequence-neutral DNA sequence polymorphisms at DNA sequence positions 171 (wild type=A; cosmid-derived=G) and 216 (wild type=C; cosmid-derived=T), was constructed by replacing the 0.4 kb AgeI/PstI restriction fragment (base pairs 90 to 524) in pcDNAI-α(1,2)FTse, that encompasses these three polymorphisms, with the corresponding 0.4 kb AgeI/PstI restriction fragment from the wild type allele. This latter fragment was derived from a 599 bp fragment encompassing this 150 bp EcoRI-AgeI fragment, using the PCR, genomic DNA template from the heterozygous secretor-positive individual described above, a synthetic oligonucleotide PCR primer (GCGCGAATTCTATAAAC ACACTTGAGATACATGCCTGTGC; Sec2 sequence underlined) corresponding to a position approximately 100 bp upstream from the "short" initiation codon, and a primer corresponding to base pairs 535 and 564 of the Sec2 coding region (GCGCGAATTCATGGACCCCTACAAAGGTGC CCGGCCGGCT; Sec2 sequence underlined). A vector encompassing the "short" form of the entire wild type allele (pcDNAI-α(1,2)FTSe-short) was constructed by exchanging the 0.5 kb PstI/XbaI restriction fragment (base pairs 524 to 1029) of pcDNAI-α(1,2)FTSe-int (encodes Ser at codon 247) with the same fragment from the wild type allele (encodes Gly at codon 247) prepared from the heterozygous secretor-positive individual described above, using the PCR. To reiterate, this exchange replaces the serine codon found at protein sequence position 247 in the allele derived from cosmid 31553 with a glycine codon found at this position in the wild type allele. Finally, plasmid pcDNAI-α(1,2)FTSe-long was constructed by replacing a 130 bp EcoRI-AgeI in pcDNAI-α(1,2)FTSe-short (encompasses the "short" initiation codon) with a 150 bp EcoRI-AgeI fragment encompassing the "long" initiation codon. This latter fragment was generated using the PCR, wild type allele template DNA, and a primer pair that amplifies the DNA sequence between base pairs −35 and −6 of the Sec2 sequence (GCGCGAATTCCCATGCTGGTCGTTCAGATGCCTTT CTCCT; Sec2 sequence underlined), corresponding to the "long" initiation codon (indicated in bold in the PCR primer sequence), and between base pairs 535 and 564 of the Sec2 coding region (GCGCGAATTCATGGACCCCTACAAAG GTGCCCGGCCGGCT; Sec2 sequence underlined). Plasmid pcDNAI without an insert served as the negative control vector.

COS-7 cells were grown in Dulbecco's modified Eagle's medium supplemented with 10% fetal calf serum, and transfected with expression vectors using a DEAE-dextran procedure, all as described previously (Larsen, R. D., Ernst, L. K., Nair, R. P. and Lowe, J. B., *Proc. Natl. Acad. Sci. USA*, vol. 87, 6674–6678 (1990), Kelly, R. J., Ernst, L. K., Larsen, R. D., Bryant, J. G., Robinson, J. S. and Lowe, J. B., *Proc. Natl. Acad. Sci. USA*, vol. 91, 5843–5847 (1994)). A control plasmid (pCDM7-CAT; ref. Kelly, R. J., Ernst, L. K., Larsen, R. D., Bryant, J. G., Robinson, J. S. and Lowe, J. B., *Proc. Natl. Acad. Sci. USA*, vol. 91, 5843–5847 (1994)) encoding bacterial chloramphenicol acetyltransferase, was cotransfected to allow normalization for transfection efficiency. Cell extracts were prepared 72 h after transfection and were used in α(1,2)fucosyltransferase assays as described below. An aliquot of the cell culture medium was also subjected to assay for α(1,2)fucosyltransferase activity. Cell extracts were also subjected to chloramphenicol acetyltransferase activity assays (Ausubel, J., and Frederick, M., *Molecular Biology-Laboratory Manuals*, vols. 1 and 2, John Wiley and Sons, New York (1987)).

Fucosyltransferase assays

Cell extracts containing 1% Triton X-100, 10% glycerol were prepared from transfected COS-7 cells using procedures previously described (Kelly, R. J., Ernst, L. K., Larsen, R. D., Bryant, J. G., Robinson, J. S. and Lowe, J. B., *Proc. Natl. Acad. Sci. USA*, vol. 91, 5843–5847 (1994)). Cell extract protein concentrations were determined using the micro-BCA assay reagent (Pierce Chemical Co.). Fucosyltransferase assays were performed in a volume of 20 μl and contained 3 μM GDP-[$^{14}$C]fucose, various concentrations of unlabeled GDP-fucose, 5 mM ATP, 25 mM sodium phosphate at pH 6.0, 2–8 μl of cell extract (approximately 25–42 μg of protein), and various concentrations of different low molecular weight glycan acceptors, as described previously (Kelly, R. J., Ernst, L. K., Larsen, R. D., Bryant, J. G., Robinson, J. S. and Lowe, J. B., *Proc. Natl. Acad. Sci. USA*, vol. 91, 5843–5847 (1994), Weston, B. W., Smith, P. L., Kelly, R. J., and Lowe, J. B., *J. Biol.Chem.*, vol. 267, 24575–24584 (1992), Rajan, V. P., Larsen, R. D., Ajmera, S., Ernst, L. K., and Lowe, J. B., *J. Biol. Chem.*, vol. 264, 11158–11167 (1989)). Preliminary assays were used to adjust the amount of cell extract added to each assay to ensure that reactions were linear (no more than 10% of GDP-fucose consumed prior to assay termination). All assays were performed in duplicate, along with parallel control reactions containing no added acceptor. Reactions were incubated at 37° C. for 2 h, and then terminated by adding 20 μl of ethanol and either 1 ml of water (for phenyl-β-D-galactoside acceptor assays) or 560 μl of water (for all other acceptor assays). The reactions were centrifuged for 5 minutes at 15,000×g, and the supernatant was collected and used to determine the amount of fucosylated product formed. When phenyl-β-D galactoside was used as the acceptor, a hydrophobic interaction chromatography procedure was used, in which the product of the reaction is retained by, and then eluted from, a Sep-Pak column (Waters-Millipore) (Rajan, V. P., Larsen, R. D., Ajmera, S., Ernst, L. K., and Lowe, J. B., *J. Biol. Chem.*, vol. 264, 11158–11167 (1989)). When neutral acceptors were used (lacto-N-biose and N-acetyllactosamine), a portion of the reaction was applied to a 500 μl column of Dowex 1×2–400, formate form (Weston, B. W., Smith, P. L., Kelly, R. J., and Lowe, J. B., *J. Biol.Chem.*, vol. 267, 24575–24584 (1992)). Unincorporated GDP-fucose is retained on the column, and radiolabeled product is recovered in the column flow-through fractions and quantitated by liquid scintillation counting. For all acceptors tested, background counts obtained in the absence of added acceptor was no more than 1% of the total added radiolabel. When total enzyme activity was measured in a plate of transfected COS-7 cells, and in the media prepared from those cells, units were defined as pmol of product (phenyl-β-D galactoside acceptor) formed per hour, per unit one μl volume of cell extract or cell media assayed.

For pH optimum determination, reactions were buffered with either 25 mM sodium acetate (pH 4.5–6.0), 25 mM sodium phosphate (pH 5.5–7.5) or 25 mM Tris-HCl (pH 7.0–9.0), using concentrated solutions of these buffers previously titrated to the various pH values. The final pH of each reaction was directly determined with a micro pH electrode as described previously (Rajan, V. P., Larsen, R. D., Ajmera, S., Ernst, L. K., and Lowe, J. B., *J. Biol. Chem.*, vol. 264, 11158–11167 (1989)). Phenyl-β-D galactoside was used as the acceptor in these assays. These experiments were completed using the enzyme derived from the pCDNAI-α (1,2)FTSe-short vector.

In assays to determine the apparent Km values, the concentration of the acceptors was varied as follows:

phenyl-β-D galactoside, 0–170 mM; lacto-N-biose I, 0–10 mM; N-acetyllactosamine, 0–12.5 mM. These assays were performed in 25 mM sodium phosphate, pH 6.0, using 3 μM GDP-[$^{14}$C]fucose. To determine the apparent Km value for GDP-fucose, 3 μM GDP-[$^{14}$C]fucose was supplemented with different amounts of unlabeled GDP-fucose (Rajan, V. P., Larsen, R. D., Ajmera, S., Ernst, L. K., and Lowe, J. B., *J. Biol. Chem.*, vol. 264, 11158–11167 (1989)) to achieve final GDP-fucose concentrations that ranged from 3 μM to 400 μM. The GDP-fucose Km determination was completed in reactions containing 25 mM phenyl-β-D galactoside, and buffered with 25 mM sodium phosphate, pH 6.0. Apparent Michaelis constants were derived from Lineweaver-Burke plots of substrate concentration-rate determinations. These experiments were completed using the enzyme derived from the pCDNAI-α(1,2)FTSe-short vector.

Pedigree analysis

Human genomic DNA was prepared from peripheral blood samples (Kumazaki, T. and Yoshida, A., *Proc. Natl. Acad. Sci. USA*, vol. 81, 4193–4197 (1984)), or from freshly plucked hairs (Rouquier, S., Lowe, J. B., Kelly, R. J., Fertitta, A. L., Lennon, G. G., and Giorgi, D., *J. Biol. Chem.* (co-submitted paper) (1994)), from 60 individuals. The secretor status of eight of these individuals was determined with standard blood group typing methods, using their red blood cells and saliva (Walker, R. H., *American Association of Blood Banks Technical Manual*. American Association of Blood Banks, Arlington, Va., USA (1990)). PCR analyses were performed using conditions described above. The primers used to sample the Trp143→ter position (GAGGAATACCGCCACATCCCGGGGGAGTAC and ATGGACCCCTACAAAGGTGCCCGGCCGGCT) correspond to positions 369 to 398 and 535 to 564, respectively, of the Sec2 coding sequence. PCR products were fixed to nylon hybridization membranes and probed with $^{32}$P-labeled allele-specific oligonucleotides (Kelly, R. J., Ernst, L. K., Larsen, R. D., Bryant, J. G., Robinson, J. S. and Lowe, J. B., *Proc. Natl. Acad. Sci. USA*, vol. 91, 5843–5847 (1994), Roth, M. S., Antin, J. H., Bingham, E. L., and Ginsburg, D., *Proc. Natl. Acad. Sci. USA*, vol. 49, 714–720 (1990)) (wild type probe TGCTCCTGGACCTTC; Trp143→ter specific probe, TGCTCCTAGACCTTC). Filters were hybridized at 37° C. in 5x SSPE (1x SSPE is 15 mM sodium citrate, 12 mM NaCl, 13 mM sodium phosphate, 1 mM EDTA, pH 7.2), 5x Denhardt's solution, 0.5% SDS, and 0.1 mg of sheared salmon sperm DNA per ml, rinsed twice at room temperature in 2x SSPE, 0.1% SDS, washed for 10 min at either 42° C. (Trp143→ter probe) or 46° C. (wild type probe) in 2x SSPE, 0.1% SDS, and subjected to autoradiography.

RESULTS:

Molecular cloning of two human genomic DNA segments cross-hybridizing with the H blood group antigen α(1,2) fucosyltransferase cDNA (FUT1).

Figure 1:
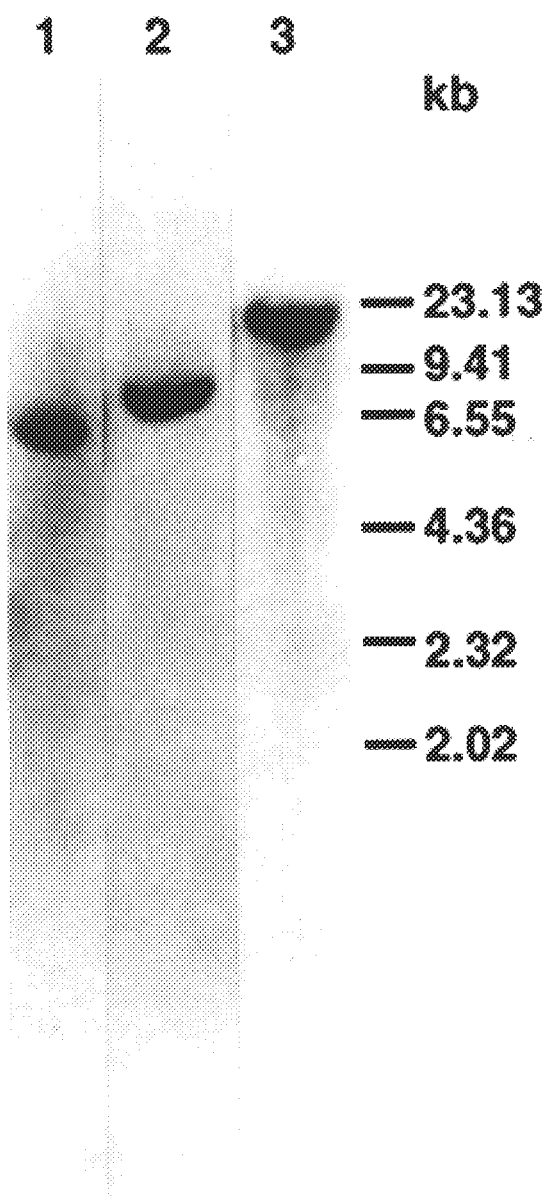
FIG. 1: Shows the results of a genomic Southern blot hybridization. EcoRI digested human genomic DNA (10 μg per lane), prepared from blood samples, was run on a 0.8% agarose gel in 0.5× TBE at 1 V/cm for 10 h, and subjected to Southern blot analysis (See "Materials and Methods"), using as probes, lane 1: 6.4 kb EcoRI fragment (FUT1) from cosmid 27513; lane2: 8.2 kb EcoRI fragment (Sec1) from cosmid 31553; lane 3: 18.5 kb EcoRI fragment (Sec2) from cosmid 31553. The sizes, indicated in kb at the right of the panel, were determined according to a lambda/HindIII marker (BRL) run in parallel.

Low stringency Southern blot hybridization experiments indicated that the coding region of the FUT1 cDNA detects a strongly hybridizing human DNA EcoRI restriction fragment of 6.4 kb (specific for the H gene), as well as a weakly hybridizing 8.2 kb EcoRI fragment (Kelly, R. J., Ernst, L. K., Larsen, R. D., Bryant, J. G., Robinson, J. S. and Lowe, J. B., *Proc. Natl. Acad. Sci. USA*, vol. 91, 5843–5847 (1994)). To ascertain the nature of this cross-hybridizing fragment, and to attempt to isolate candidate sequences for the FUT2 locus, two chromosome 19 cosmid libraries were screened at low stringency with the FUT1 cDNA probe. A total of 13 hybridization-positive cosmid clones were isolated from the eight-fold redundant libraries. Southern blot analysis of an EcoRI digest of these cosmid clones allowed them to be placed into different groups, based upon their restriction patterns, and the size(s) of the fragment(s) that hybridized with the FUT1 probe. Twelve cosmids contained a 6.4 kb EcoRI fragment that hybridized strongly with the FUT1 probe, and that corresponds to the H locus (Kelly, R. J., Ernst, L. K., Larsen, R. D., Bryant, J. G., Robinson, J. S. and Lowe, J. B., *Proc. Natl. Acad. Sci. USA*, vol. 91, 5843–5847 (1994)). The remaining cosmid (31553) contained a weakly hybridizing 8.2 kb EcoRI fragment (corresponding to the fragment detected by the FUT1 probe on human genomic DNA Southern blots), and a second, very weakly hybridizing 18.5 kb EcoRI hybridizing fragment which was not evident on low stringency human genomic Southern blots. Cosmid 27513 was chosen as the reference clone containing the 6.4 kb EcoRI (FUT1) fragment. The 6.4 kb EcoRI fragment (from cosmid 27513), and the 8.2 kb and 18.5 kb EcoRI fragments (from cosmid 31553) were gel purified and used to probe Southern blots containing EcoRI-digested human genomic DNA. As shown in FIG. 1, each probe hybridizes to a single human genomic EcoRI fragment corresponding to its own size. This result demonstrates that these three different cloned DNA fragments accurately represent their counterparts within the human genome.

Fluorescence in situ hybridization localizes the FUT1 cross-hybridizing sequences to 19q13.3.

Figure 2:
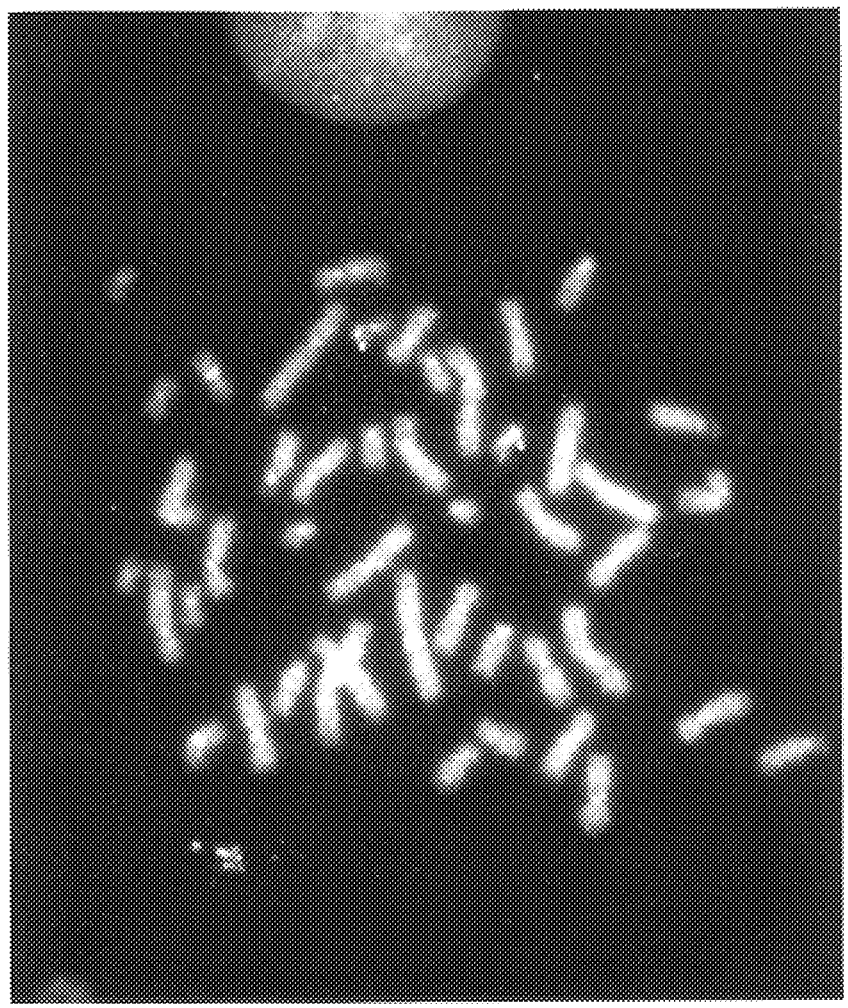
FIG. 2 shows the results of fluorescence in situ hybridization mapping of cosmids 27513 and 31553. Two-color FISH on metaphase chromosomes of cosmids 27513 and 31553 probes using avidin-Texas red (red signals) and digoxygenin-FITC (green signals). A double-exposure photograph of probes provided localization of both signals: a 15-second exposure through a two-color filter permitted detection of Texas red and FITC labels, followed by a short automatic exposure through a separate filter for visualization of DAPI-stained metaphase. A discrete signal is discernable on all four chromosome 19 chromatids for each cosmid. The band location of these signals (q13.3) is determined relative to DAPI/actinomycin bands.

Fluorescent in situ hybridization (FISH) procedures were used to determine if cosmid clones 27513 and 31553 were physically linked on chromosome 19. Both cosmids localize to 19q13.3 when hybridized to metaphase chromosome spreads (FIG. 2). Cosmids 27513 and 31553 are too close to be mapped relative to each other (i.e., less than 1 Mbp, "Materials and Methods"), using two-color metaphase ordering (FIG. 2). The closest flanking markers are cosmid 18618 on the proximal side, and cosmid 15743 on the distal side. These have been previously FISH-mapped on q13.3, and q13.3–13.4, respectively (Trask, B. J., Fertitta, A., Christensen, M., Tynan, K., Youngblom, J., Bergmann, A., Copeland, A., de Jong, P., Mohrenweiser, H., Olsen, A. and Carrano, A. V., *Genomics*, vol. 15, 133–145 (1993)), confirming the chromosome banding results. The distance between cosmids 27513 and 31553 was also found to be too small to be measured precisely when FISH mapping to interphase nuclei was used, indicating that these two cosmids are separated by less than 100 kb (Trask, B. J., Pinkel, D. and van den Engh, G. J., *Genomics*, vol. 5, 710–717 (1989), van den Engh, G. J., Sachs, R. and Trask, B. J., *Science*, vol.257, 1410–1412 (1992)) on 19q13.3.

Characterization of YACs and BACs spanning the region containing the FUT1 cross-hybridizing sequences.

Based on the FISH results, the ICRF YAC library and the Caltech BAC library ("Materials and Methods") were screened in an attempt to isolate one cloned DNA molecule containing FUT1 and FUT1-related sequences. SfiI inserts of cosmids 27513 and 31553 were radioactively labeled and used separately as probes to screen these two libraries.

The YAC library screening yielded a single 450 kb YAC (clone F117A10) that hybridized only with cosmid 27513. FISH and Southern blot analyses, and end probe mapping studies (Larin, Z., Monaco, A. P. and Lehrach, H., *Proc. Natl. Acad. Sci. USA*. vol. 88, 4123–4127 (1991)), demonstrate that YAC F117A10 is chimeric on its left end. No YACs were obtained with cosmid 31553.

Two BACs (28F10, 152C3) were isolated using cosmid 31553, while none were obtained with cosmid 27513. Both BACs contain inserts of approximately 120 kb. EcoRI digestion of these two BACs yields the same pattern, suggesting that they contain the same DNA segment. Southern blot analyses show that both BACs contain sequences that cross-hybridize at high stringency with cosmid 31553, but not with cosmid 27513. Southern blot analyses also show that cosmid 31553 identifies the 8.2 kb and 18.5 kb EcoRI fragments found in cosmid 31553, indicating that both BACs contain the two FUT1-related sequences. Only 28F10 was used for further experiments.

Construction of a cosmid contig and EcoRI map of the region spanning FUT1 and its cross-hybridizing sequences.

Figure 3:
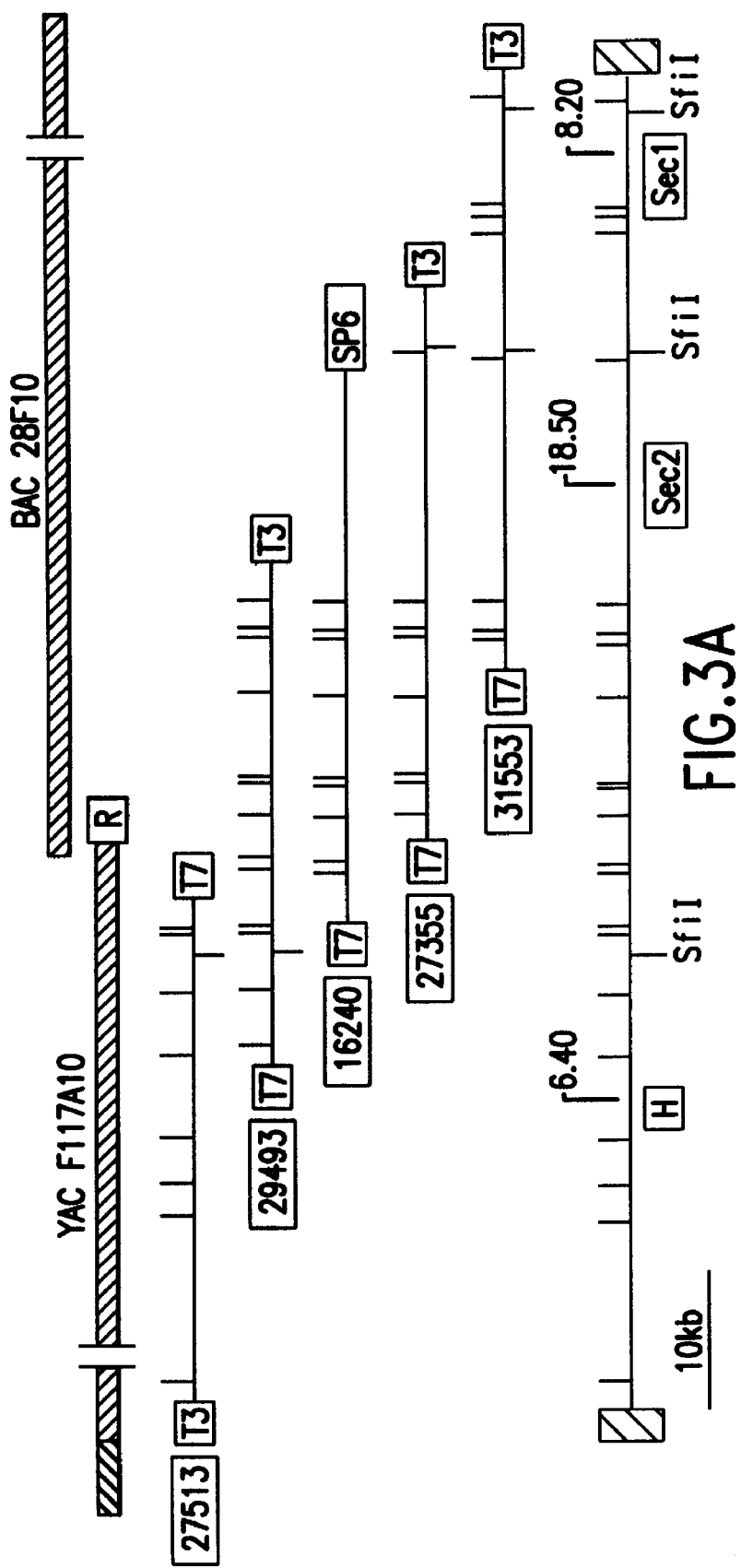
FIGS. 3*a* and *b* are physical maps of the region encompassing the FUT1 and FUT1-related sequences on 19q13.3. (a) Physical map of the FUT1 and FUT1-related region. The region is covered by a set of overlapping cosmids numbered and represented by solid lines. The YAC F117A10 and the BAC 28F10 are represented above the cosmid contig: the shaded lines are the portions belonging to the FUT region. The YAC dashed line indicates the chimeric portion. The boxed R indicates the right arm of the pYAC4 vector. This YAC overlaps the cosmids 27513, 29493 and 16240 and extends the cosmid contig on the left side; the BAC overlaps the cosmids 16240, 27355 and 31553 and extends the cosmid contig on the right side. The precise overlaps between the YAC, the BAC and cosmid 16240 were not determined. The interrupted solid lines in the YAC and BAC indicate they are not drawn to scale. The partial EcoRI digest strategy of the 100 kb encompassing cosmid contig was used to order the EcoRI fragments (See "Materials and Methods"). EcoRI sites are indicated by vertical lines. SfiI sites are positioned. The vector primer sequences (T3, T7 or Sp6) are boxed at each cosmid end. The position of FUT1 (H), Sec1 and Sec2 (boxed) are placed on the genomic map; sizes of the corresponding EcoRI fragments are indicated in kilobases. (b) PstI restriction map of the 18.10 kb EcoRI fragment of cosmid 16240. The PstI restriction map was established by a partial PstI digestion. The FUT1 cDNA probe hybridizes at low stringency (See "Materials and Methods") the 1.3 kb fragment (sec2). The hatched rectangle represents the ~500 bp cDNA.

To establish a single cosmid contig containing the region between FUT1 and the FUT1-related sequences, the two cosmid libraries were screened separately with the SfiI inserts of cosmids 27513 and 31553. Twenty five cosmids hybridized to cosmid 27513 (including cosmid 27513 and the other 11 isolated in the original screen with the FUT1 probe). Nine cosmids hybridized to cosmid 31553. Two unique cosmids (29493 and cosmid 16240) hybridized both to cosmid 27513 and to cosmid 31553. These data, and Southern blot analyses, indicate cosmids 16240, 27355, and 29493 bridge the gap between cosmid 27513 and cosmid 31553, ordered as 27513–29493–16240–27355–31553, and yield the physical map shown in FIG. 3a. The YAC F117A10 and the BAC 28F10 have been positioned relative to the cosmid contig by hybridizing radiolabeled Alu-PCR products derived from each, to the two cosmid libraries, and to a blot containing the EcoRI-digested DNAs derived from cosmids 27513 through 31553. The YAC F117A10 overlaps cosmids 27513, 29493, 16240, and the BAC 28F10 overlaps cosmids 16240, 27355 and 31553 (FIG. 3a). Additional Southern blot analyses ("Materials and Methods") yield a fine EcoRI map of a five cosmid contig that encompasses approximately 100 kb (FIG. 3a), and support the results of the FISH analyses presented above. Additional cosmids adjacent to this contig, and overlapping it, have also been analyzed, and confirm the structure of this region.

Assignment of the FUT1-related sequences to specific EcoRI fragments within the cosmid contig.

Figure 4:
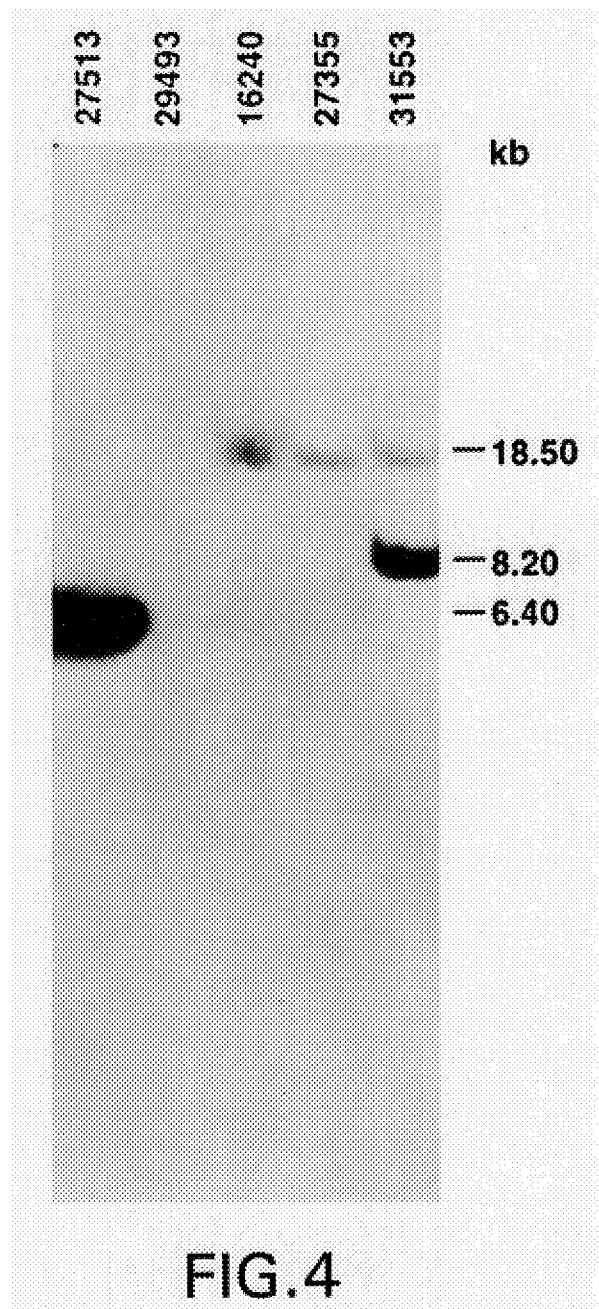
FIG. 4 shows the results of a Low stringency Southern blot analysis of the cosmid contig using the FUT1 fucosyl-transferase cDNA probe. The cosmids were EcoRI digested (1 µg) and analysed by electrophoresis, on a 0.5% agarose gel. The gel was blotted, and the membrane hybridized with radiolabeled FUT1 cDNA probe using low stringency wash conditions. The 8.2 kb Sec1-fragment is contained only in cosmid 31553. The 18.50 kb EcoRI Sec2-fragment is contained in cosmids 16240, 27355 and 31553. The sizes, indicated in kb at the right of the panel, were determined by comparison to a lambda/HindIII and 1 kb ladder standards (BRL) run in parallel.

FIG. 3a displays the position of the H locus within the 6.4 kb EcoRI fragment of cosmid 27513, and the positions of the two FUT1-related sequences within the 8.2 kb and 18.5 kb EcoRI fragments in cosmid 31553. To determine if other FUT1-related sequences might be present within the region bounded by the cosmid contig, a Southern blot of EcoRI digested DNA derived from the 5 cosmids representing this contig was prepared and probed at low stringency using the FUT1 cDNA probe. As shown in FIG. 4, only the three previously identified cross-hybridizing EcoRI fragments are identified (the 6.4 kb fragment of FUT1, the 8.2 kb fragment, and the 18.5 kb fragment), indicating that no other FUT1-related sequences are present within this contig. (The 18.5 kb fragment is slightly truncated to 18.1 kb in cosmid 16240; see FIGS. 3a and b). After high stringency washes, both 8.2 kb and 18.5 kb signals disappeared confirming the heterologous nature of that hybridization. Because these latter EcoRI fragments are closely linked to and cross-hybridize with the FUT1 locus, they represent candidates for the human Secretor blood group locus (FUT2). We therefore termed them Sec1 (for Secretor candidate 1; 8.2 kb fragment) and Sec2 (for Secretor candidate 2; 18.5 kb fragment). The Sec1 and Sec2 EcoRI fragments are separated by 12.0 kb, and are 65.5 kb and 35.0 kb apart, respectively, from the 6.4 kb EcoRI fragment corresponding to FUT1 (FIG. 3a).

Direct selection of cDNAs derived from the cosmid contig.

Figures 5A, 5B:
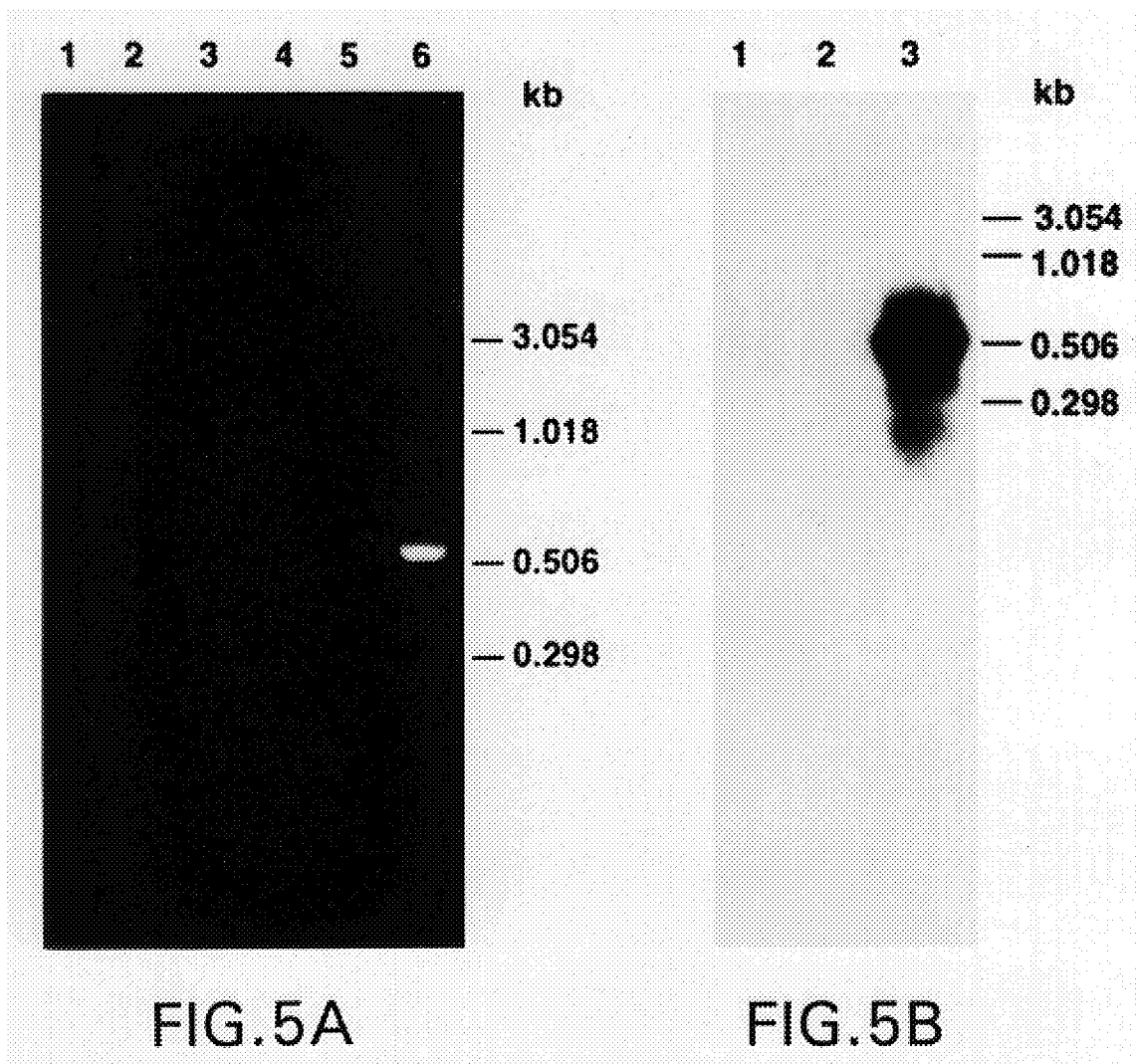
FIGS. 5a and b show the results of direct selection of cDNA using magnetic bead capture. (a) Gel electrophoresis pattern of selected products after first round (lanes 1, 3, 5) and second round (lanes 2, 4, 6) of selection-amplification, utilising cosmids 27513 (lanes 1 and 2), 29493 (lanes 3 and 4) and 31553 (lanes 5 and 6) and using Uni-Amp primers for PCR amplification (See "Materials and Methods"). One fifth of the PCR reaction was loaded on each lane. (b) A gel with the second round of selection-amplification (1/10 of the PCR reaction) of cosmids 27513 (lane 1), 29493 (lane 2) and 31553 (lane 3) was transferred to a nylon membrane and hybridized with the $^{32}$P-labeled SfiI insert of cosmid 31553. Relative mobilities of molecular size markers (1 kb ladder (BRL)) are indicated, in kb, at the right of each picture.

To determine if Sec1 or/and Sec2 are transcribed, a hybrid selection method in which a cloned genomic sequence rescues corresponding transcribed sequences from a population of cDNAs (Parimoo, S., Patanjali, S. R., Shukla, H., Chaplin, D. D. and Weissman, S. M., *Proc. Natl. Acad. Sci. USA*, vol. 88, 9623–9627 (1991), Lovett, M., Kere, J. and Hinton, L., *Proc. Natl. Acad. Sci. USA*, vol. 88, 9628–9632 (1991), Morgan, J. G., Dolganov, G. M., Robbins, S. E., Hinton, L. M. and Lovett, M., *Nuc. Acids Res.*, vol. 20, 5173–5179 (1992), Korn, B., Sedlacek, Zdenek, Manca, A., Kioschis, P., Konecki, D., Lehrach, H. and Poustka, A., *Human Molec. Genet.* vol. 1, 235–242 (1992), Tagle, D. A., Swaroop, M., Lovett, M. and Collins, F., *Nature*. vol. 361, 751–753 (1993)) was used. Double-stranded cDNA prepared from human fetal brain mRNA was subjected to hybrid selection ("Materials and Methods") with cosmid 27513, 29493, or 31553, to represent the minimal spanning set of the contig. An intense ~500 bp PCR product was obtained after the second round of selection with cosmid 31553 (FIG. 5a). This product hybridizes strongly with cosmid 31553 (FIG. 5b), suggesting that it corresponds to a transcribed segment of cosmid 31553. Discrete products were also obtained with cosmid 27513, but not with cosmid 29493 (FIG. 5a). The product derived from cosmid 27513 hybridizes to cosmid 27513, and to a FUT1 cDNA probe, suggesting that it rescued FUT1 cDNAs from the fetal brain cDNA preparation. This sequence was not analyzed further.

The cosmid 31553-selected cDNA corresponds to the Sec2 sequence, and to a 3.35 kb transcript in human intestine and lung.

Figures 6A, 6B:
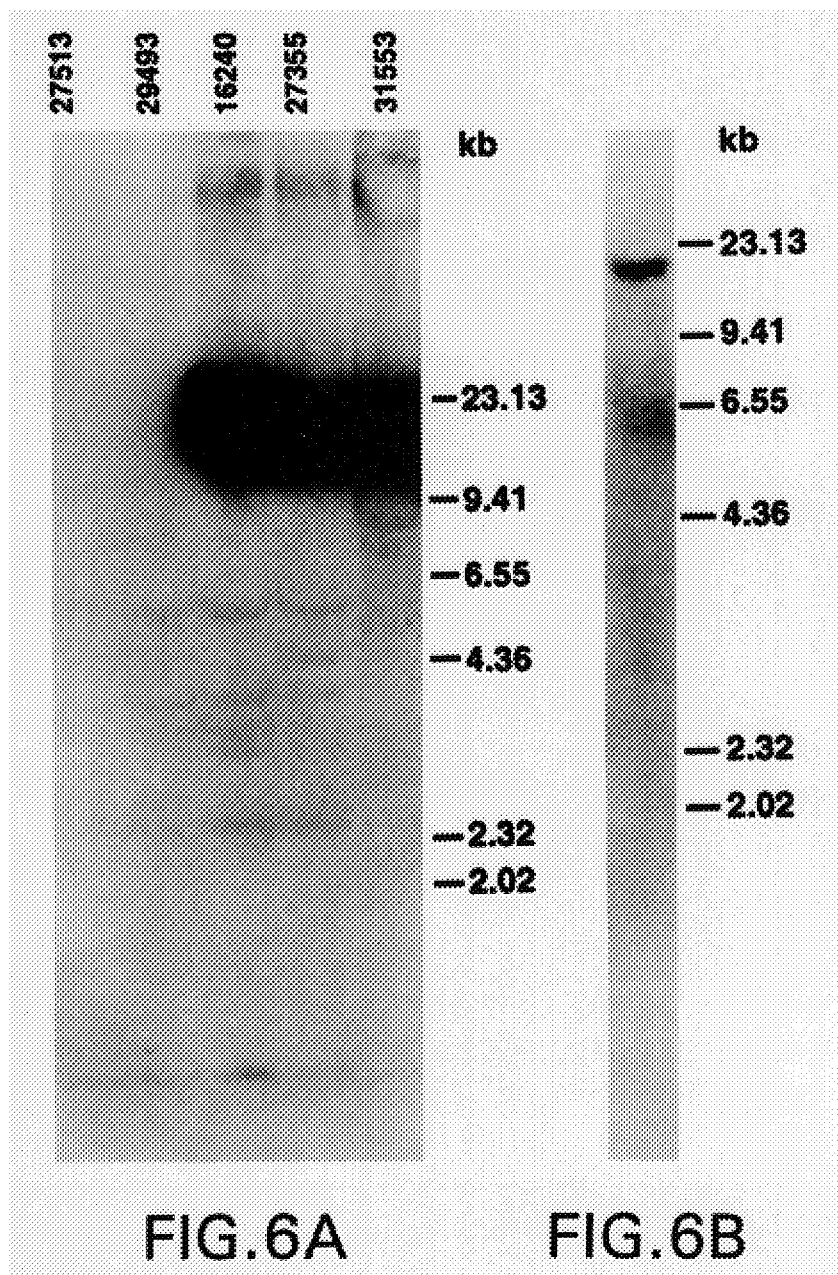
FIGS. 6a and b show the results of a Southern blot hybridization of the hybrid selected cDNA. (a) The cosmids composing the contig described in FIG. 3a were EcoRI digested (1 µg) and analysed by electrophoresis on a 0.5% agarose gel. The gel was blotted, and the membrane hybridized with the Sec2 selected cDNA piece. (b) EcoRI digested human genomic DNA (10 µg per lane), prepared from blood samples, was run on a 0.8% agarose gel in 0.5× TBE at 1 V/cm for 10 h, and subjected to Southern blot analysis using the same probe. The sizes, indicated at the right each panel, were determined according to a lambda/HindIII marker (BRL) run in parallel.

The ~500 bp cosmid 31553-derived hybrid selected cDNA hybridizes to the 18.5 kb EcoRI fragment (containing Sec2) on the cosmid contig (FIG. 6a), and to a single 18.5 kb EcoRI fragment on a human genomic DNA Southern blot (FIG. 6b). These results demonstrate that this ~500 bp cDNA does not contain significant amounts of repetitive sequence, and suggest that it corresponds to the Sec2 sequence within the 18.5 kb EcoRI fragment encompassed by cosmids 16240, 27355 and 31553 (FIG. 3a).

Figure 7:
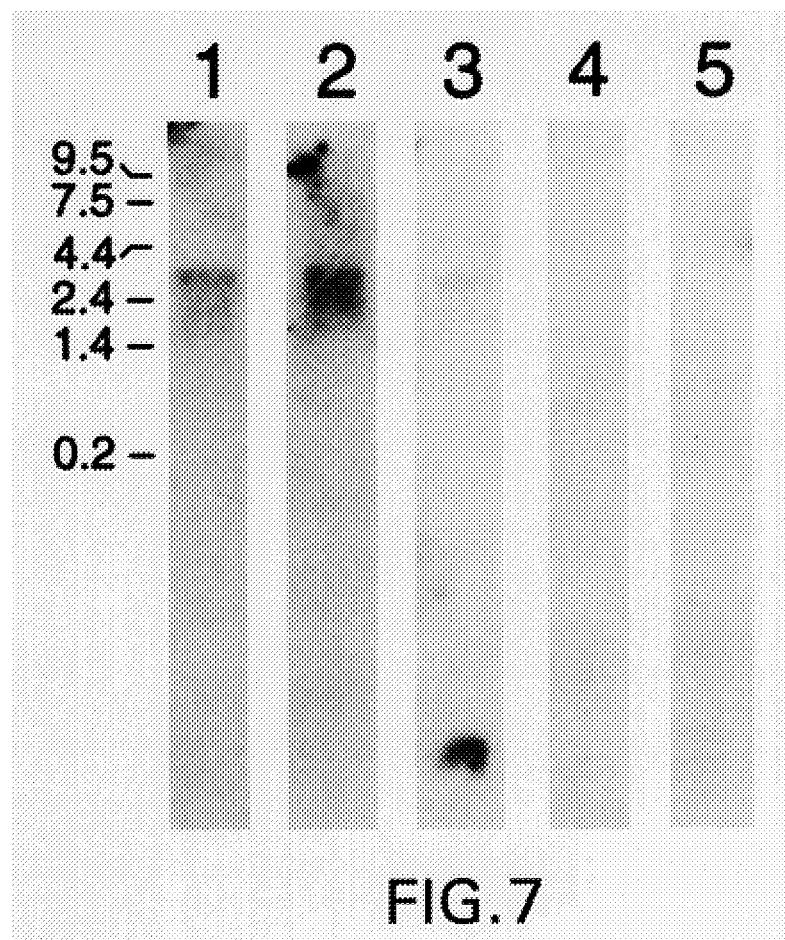
FIG. 7 shows the results of a Northern blot analysis of human mRNA. Northern blots were prepared with five micrograms of polyadenylated mRNA isolated from human tissues (colon, lane 1; small intestine, lane 2; lung, lane 3; liver, lane 4; kidney, lane 5) (see "Materials and Methods"). Blots were probed with the radiolabeled Sec2 cDNA isolated by hybrid selection using cosmid 31553, using hybridization and washing conditions described in "Materials and Methods" and in Smith, D. F., et al, *J. Biol. Chem.*, vol. 265, 6225–6234 (1990). The migration positions of RNA molecular size standards, in kilobases are indicated at right.

This cDNA identifies a 3.35 kb transcript in colon and small intestine, and a less abundant yet similarly sized transcript in lung (FIG. 7). Transcripts corresponding to this cDNA were not detected in kidney or liver. Since the Secretor locus determines expression of H blood group determinants in intestinal, colonic, and pulmonary epithelia, but not in hepatocytes, or in the kidney (Oriol, R., Danilovs, J. and Hawkins, B. R., *Am. J. Hum. Genet.*, vol. 33, 421–431 (1981)), these results are consistent with the possibility that this cDNA and its transcribed locus within Sec2 correspond to the human Secretor, or FUT2, locus.

The sequence of this cDNA and corresponding genomic DNA indicates that it is within the Sec2 sequence in the 18.5 kb EcoRI fragment (FIG. 3a), lies 3' to the termination codon of a novel human α(1,2)fucosyltransferase gene and thus represents the 3' untranslated region of this locus.

Thus, the sequence of the hybrid selected cDNA, and its genomic counterpart, unambiguously assign its cognate transcript to the human Secretor blood group α(1,2) fucosyltransferase locus.

The Sec1 DNA segment is most probably a pseudogene

Sequence analysis of the cross-hybridizing portion of Sec1 identified substantial primary sequence similarity to the human H blood group α(1,2)fucosyltransferase gene (FIG. 8). This sequence yields an open reading frame with primary protein sequence similarity to the H α(1,2)

fucosyltransferase, beginning at a methionine codon at a position that roughly corresponds to the initiator codon of the H α(1,2)fucosyltransferase. This open reading frame predicts an amino terminal hydrophobic segment typical of the membrane spanning signal-anchor sequences found in mammalian glycosyltransferases (Lowe, J. B., *Seminars in Cell Biology*, vol. 2, 289–307 (1991)). Nonetheless, the DNA sequence of the Sec1 fragment does not yield a single long translational reading frame corresponding to the H locus, due to the presence of frameshift and nonsense mutations that disrupt this reading frame, and each of the other two, relative to the H α(1,2)fucosyltransferase reading frame. Maximal and sustained alignment of amino acid sequence residues predicted by the Sec1 DNA sequence with the H α(1,2)fucosyltransferase sequence may be accomplished, however, by conceptual suppression of a single frameshift mutation, and a single non-sense mutation, as shown in FIG. 8. This conceptual sequence maintains several predicted asparagine-linked glycosylation sites (Kornfeld, R., and Kornfeld, S., *Annu. Rev. Biochem.*, vol. 54, 631–664 (1985)), including some that are at positions precisely corresponding to those in the H α(1,2) fucosyltransferase. Expression of this segment in α((1,2) fucosyltransferase-deficient COS-7 cells (via vectors pcDNAI-Sec1 or pcDNAI-Sec1-rev; see "Materials and Methods") generates no detectable α(1,2)fucosyltransferase activity. Furthermore, transcripts corresponding to this gene are not detectable by Northern blot or cDNA selection approaches, although these approaches would not detect unstable Sec1-derived transcripts. Thus, these observations, together with absence of an uninterrupted open reading frame in the Sec1 segment, and its inability to encode detectable α(1,2)fucosyltransferase activity, lead to the conclusion that the Sec1 segment isolated from cosmid 31553 represents a pseudogene.

An open reading frame in the Sec2 DNA seament shares primary sequence similarity with the human H blood group α(1,2)fucosyltransferase Sequence analysis of the Sec2 segment reveals substantial primary DNA sequence similarity to the H blood group α(1,2)fucosyltransferase gene (FIG. 9). Translation of the Sec2 sequence, beginning at either of two closely-spaced, in frame methionine codons, yields a long open reading frame with substantial primary amino acid sequence similarity to the human H blood group α(1,2)fucosyltransferase (FIG. 9). This similarity is most marked, and sustained, beginning at a position corresponding to an alanine residue at position 66 in the H α(1,2)fucosyltransferase. Each of the two closely-spaced in frame methionine codons is an appropriate candidate to be an initiator codon; each falls within a consensus splice acceptor splice site (Rio, D.C., *Curr. Opin. Genet. Dev.*, vol. 3, 574–584 (1993)), as does the initiator codon at the beginning of the single coding exon in the human H α(1,2)fucosyltransferase gene (Kelly, R. J., Ernst, L. K., Larsen, R. D., Bryant, J. G., Robinson, J. S. and Lowe, J. B., *Proc. Natl. Acad. Sci. USA*, vol. 91, 5843–5847 (1994)) (FIG. 9). Furthermore, the sequence context of each putative initiation codon (distal to the predicted splice acceptor junction ↓; N→CCATGC; N↓CCATGG) is substantially similar to the Kozak consensus translation initiation sequence (Kozak, M., *Annu. Rev. Cell. Biol.*, vol. 8, 197–225 (1992)). This arrangement suggests the possibility that alternative splicing events might lead to the synthesis of two different polypeptides, that differ by the presence, or absence, of an 11 amino acid NH2-terminal extension.

Translation from these putative initiator codons predicts the synthesis of either a 332 amino acid long polypeptide, or a 343 amino acid long polypeptide, each of which shares 68% sequence identity with the human α(1,2) fucosyltransferase protein sequence, across 292 corresponding amino acid residues distal to the conserved alanine residue (FIG. 9). The NH2-terminus of the protein(s) consists of 3 residues (or 14 residues) that precede a 14 residue hydrophobic segment. This hydrophobic segment is flanked by charged residues, and is predicted to function as a signal-anchor sequence (FIG. 9), in a motif that corresponds to the type 2 transmembrane topology typical of mammalian glycosyltransferases (Lowe, J. B., *Seminars in Cell Biology*, vol. 2, 289–307 (1991)). By analogy to these enzymes, it is predicted that the 315 residues that comprise the COOH-terminal catalytic domain reside within the lumen of the Golgi apparatus. Three potential asparagine-linked glycosylation sites are present in this COOH-terminal domain; two of these sites are at positions corresponding to the two potential asparagine-linked glycosylation sites previously identified in the H α(1,2)fucosyltransferase (FIG. 9). Sequence analysis also identifies a region of sequence identity between a region 3' to the predicted termination codon in the Sec2 sequence, and the hybrid-selected cDNA derived from human small intestinal tissue (FIG. 9). This suggests that the Sec2 sequence encodes an α(1,2) fucosyltransferase gene expressed in some gastrointestinal epithelial cells.

The open reading frame in the Sec2 DNA segment encodes an α(1,2)fucosyltransferase activity To confirm that this segment encodes an α(1,2) fucosyltransferase, a segment encompassing the 332 amino acid residues initiated at the second putative initiator methionine codon was cloned into a mammalian expression vector ("Materials and Methods"), to create pCDNAI-α(1, 2)FTSe-short. A similar vector, termed pCDNAI-α(1,2) FTSe-long, was assembled to direct synthesis of the 343 amino acid residues initiated at the first putative initiator methionine codon. These vectors, or a control vector, were then transfected into α(1,2)fucosyltransferase-deficient COS-7 cells ("Materials and Methods"). Extracts prepared from the transfected COS-7 cells, or control transfected COS-7 cells, were then subjected to assays for α(1,2) fucosyltransferase activity. Preliminary assays using an acceptor substrate specific for α(1,2)fucosyltransferase activity (phenyl-β-D-galactoside, Chester M. A., et al, *Eur. J. Biochem.*, vol. 69, 583–592 (1976)) indicated that cells transfected with pCDNAI-α(1,2)FTSe-short, or with pCDNAI-α(1,2)FTSe-long, contain substantial amounts of α(1,2)fucosyltransferase activity. Since previous work indicates that the Secretor locus-encoded α(1,2) fucosyltransferase maintains characteristic pH-activity profiles and apparent Michaelis-Menten constants for acceptor substrates and GDP-fucose (Le Pendu, J., Cartron, J. P., Lemieux, R. U. and Oriol, R., *Am. J. Hum. Genet.*, vol. 37, 749–760 (1985), Kumazaki, T. and Yoshida, A., *Proc. Natl. Acad. Sci. USA*, vol. 81, 4193–4197 (1984), Sarnesto, A., Kohlin, T., Thurin, J., and Blaszczyk-Thurin, M., *J. Biol. Chem.*, vol. 265, 15067–15075 (1990), Sarnesto, A., Kohlin, T., Hindsgaul, O., Thurin, J., and Blaszczyk-Thurin, M., *J. Biol. Chem.*, vol. 267, 2737–2744 (1992), Rajan, V. P., Larsen, R. D., Ajmera, S., Ernst, L. K., and Lowe, J. B., *J. Biol. Chem.*, vol. 264, 11158–11167 (1989)), these parameters were determined for the α(1,2)fucosyltransferase encoded by the Sec2 segment.

Figure 10A:
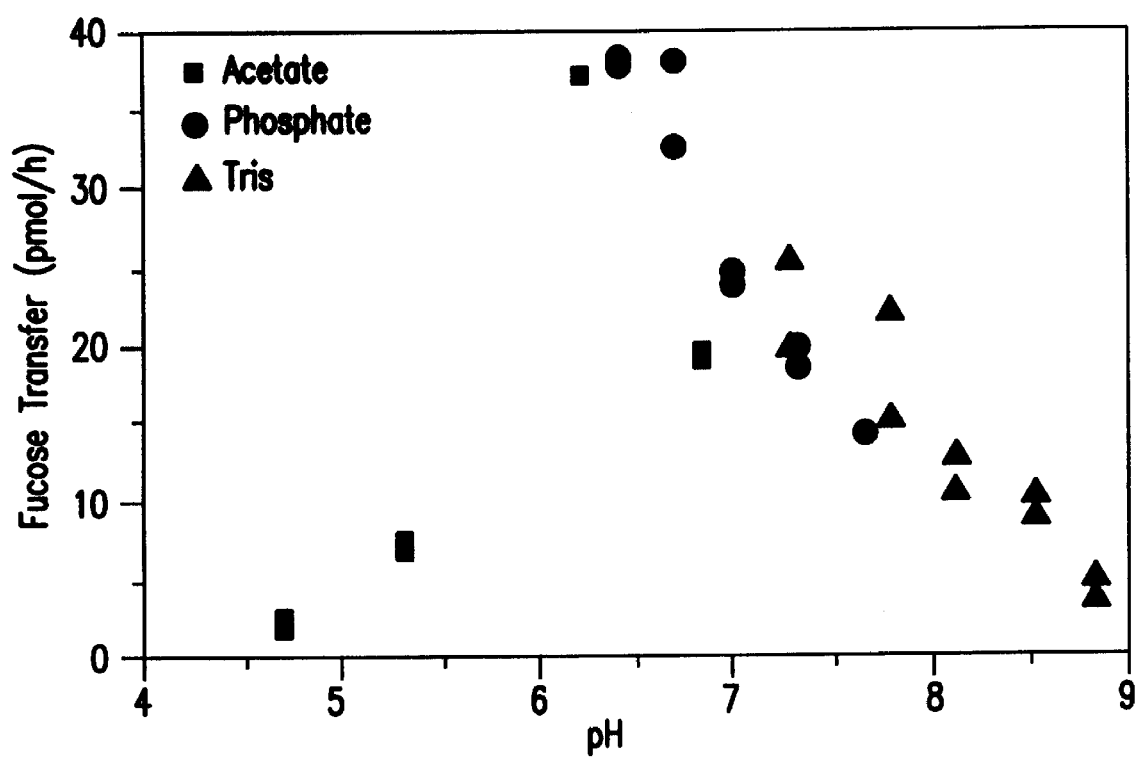
FIGS. 10a–e show the catalytic properties of the Sec2-encoded α(1,2)fucosyltransferase activity. (a) effect of pH on α(1,2)fucosyltransferase activity. Enzyme activity encoded by the Sec2 segment in transfected COS-7 cell extracts was measured using 25 mM phenyl-β-D-galactoside and 3 µM GDP-[$^{14}$C]fucose, as described in "Materials and Methods". Buffers used in assays at various pHs are indicated by the symbols in the boxed legend. The pH values displayed here were determined by measuring the pH of the assay solution, as described in "Materials and Methods". (b) apparent Michaelis constant for phenyl-β-D-galactoside. The apparent $K_m$ ($K_m$=11.5 mM) for the Sec2-encoded α(1,2)fucosyltransferase was determined using 3 µM GDP-[$^{14}$C]fucose, as described in "Materials and Methods". (c) apparent Michaelis constant for lacto-N-biose I. The apparent $K_m$ ($K_m$=3.6 mM) for the Sec2-encoded α(1,2)fucosyltransferase was determined using 3 µM GDP-[$^{14}$C] fucose as described in "Materials and Methods". (d) apparent Michaelis constant for N-acetyllactosamine. The apparent $K_m$ ($K_m$=3.8 mM) for the Sec2-encoded α(1,2) fucosyltransferase was determined using 3 µM GDP-[$^{14}$C] fucose as described in "Materials and Methods". (e) apparent Michaelis constant for GDP-fucose. The apparent $K_m$ ($K_m$=197 µM) for the Sec2-encoded β(1,2) fucosyltransferase was determined using 25 mM phenyl-β-D-galactoside as described in "Materials and Methods"
Figure 10B:
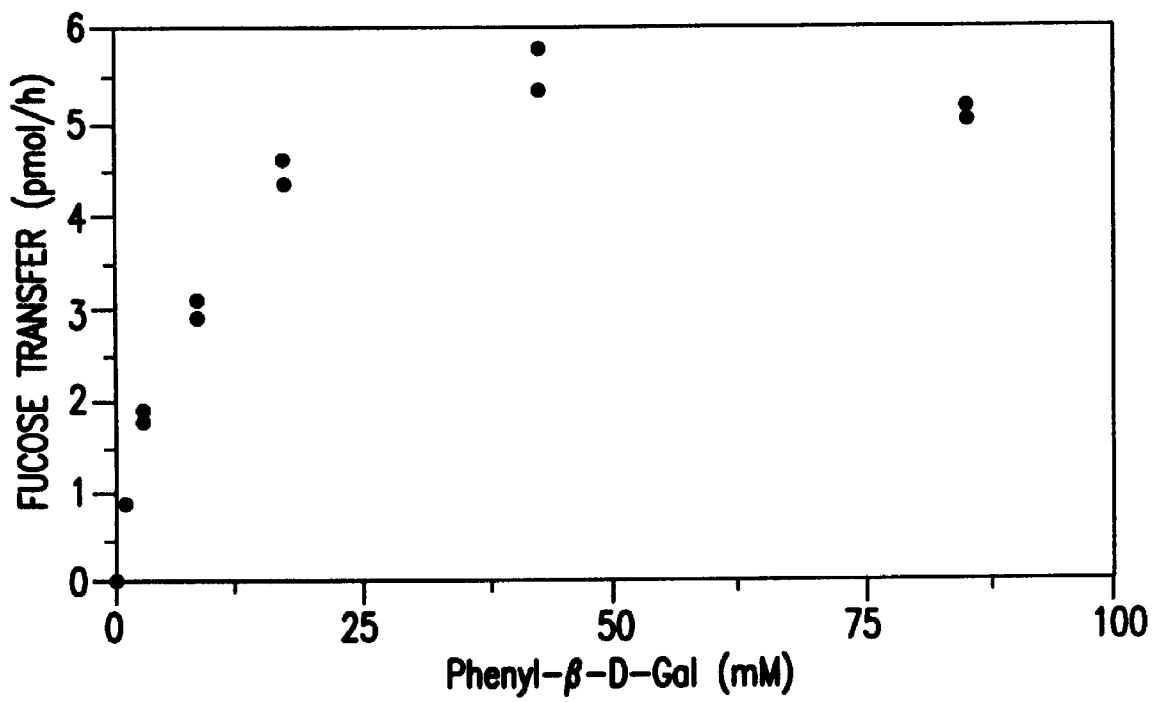
Figure 10C:
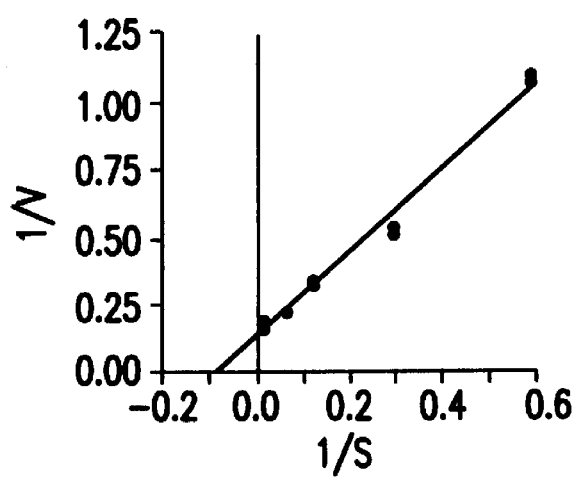
Figure 10D:
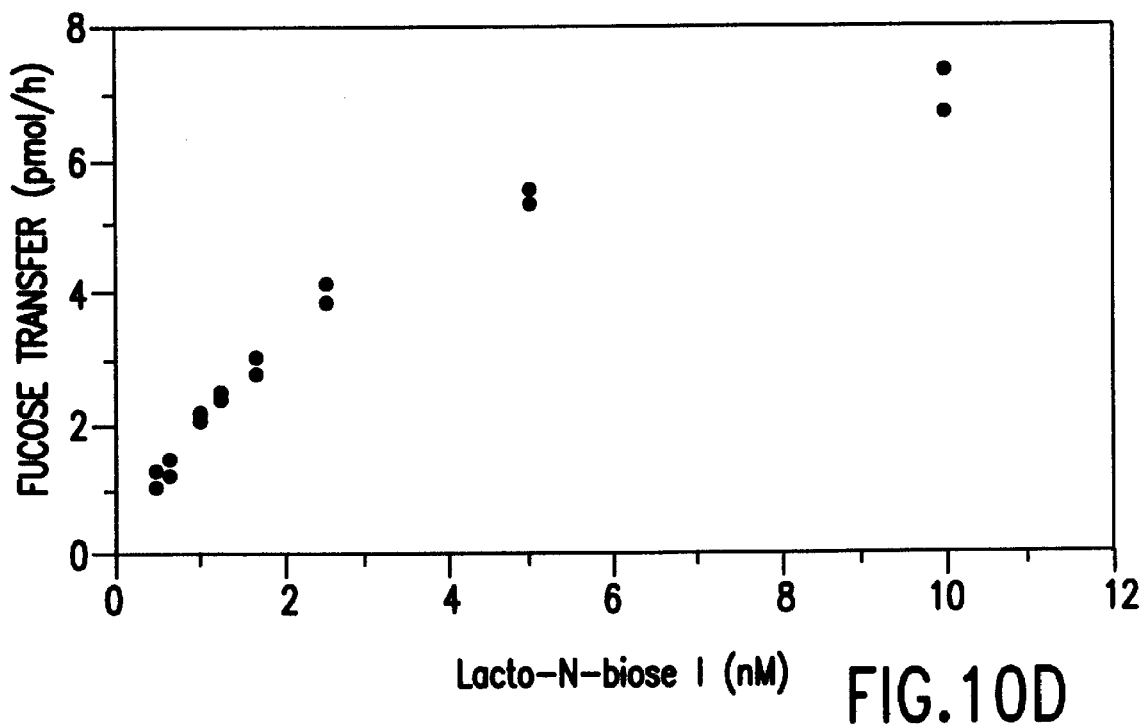

The Sec2-encoded α(1,2)fucosyltransferase is catalytically similar to the α(1,2)fucosyltransferase determined by the human Secretor blood group locus The pH optimum of the α(1,2)fucosyltransferase activity in transfected cell extracts ("Materials and Methods") is approximately 6.5 (FIG. 10a). This value is similar to that reported previously for the Secretor α(1,2) fucosyltransferase (Rajan, V. P., Larsen, R. D., Ajmera, S., Ernst, L. K., and Lowe, J. B., *J. Biol. Chem.*, vol. 264, 11158–11167 (1989)). Kinetic analyses demonstrate that this α(1,2)fucosyltransferase activity maintains an apparent Michaelis-Menten constant of 11.5 mM (FIG. 10b) for the artificial acceptor phenyl-β-D-galactoside. This $K_m$ is similar to the apparent $K_m$ of 15.1 mM obtained for a preparation of human Secretor α(1,2)fucosyltransferase partially purified from human milk (Kumazaki, T. and Yoshida, A., *Proc. Natl. Acad. Sci. USA*, vol. 81, 4193–4197 (1984), Rajan, V. P., Larsen, R. D., Ajmera, S., Ernst, L. K., and Lowe, J. B., *J. Biol. Chem.*, vol. 264, 11158–11167 (1989)), and is essentially identical to the apparent $K_m$ of 11.4 mM reported for a preparation of the human Secretor α(1,2) fucosyltransferase purified from human serum (Sarnesto, A., Kohlin, T., Hindsgaul, O., Thurin, J., and Blaszczyk-Thurin, M., *J. Biol. Chem.*, vol. 267, 2737–2744 (1992)). The apparent $K_m$s for the acceptor substrates lacto-N-biose I (3.6 mM, FIG. 10c), and N-acetyllactosamine (3.8 mM, FIG. 10d) are also generally quite similar to those determined by others for the Secretor locus-encoded α(1,2) fucosyltransferase (Le Pendu, J., Cartron, J. P., Lemieux, R. U. and Oriol, R., *Am. J. Hum. Genet.*, vol. 37, 749–760 (1985), Kumazaki, T. and Yoshida, A., *Proc. Natl. Acad. Sci. USA*, vol. 81, 4193–4197 (1984), Sarnesto, A., Kohlin, T., Hindsgaul, O., Thurin, J., and Blaszczyk-Thurin, M., *J. Biol. Chem.*, vol. 267, 2737–2744 (1992)) (Table I).

TABLE I

| Substrate | Enzyme | Apparent Km (mM) |
|---|---|---|
| phenyl-β-D-galactoside | H | 2.4 |
| | H | 3.0 |
| | H | 3.1 |
| | H | 1.4 |
| | H | 4.6, 6.4 |
| | pCDNAI-α(1,2)FTSe | 11.5 |
| | Secretor | 11.4 |
| | Secretor | 15.1 |
| | Secretor | 10.0 |
| | Secretor | 46.0 |
| lacto-N-biose I | H | 2.0 |
| | H | 3.5 (—O—Me) |
| | pCDNAI-α(1,2)FTSe | 3.6 |
| | Secretor | 1.4 (—O—Me) |
| | Secretor (lacto-N-tetraose) | 1.6 |
| | Secretor | 1.0 |
| N-acetyllactosamine | H | 1.9 |
| | H | 25.0 |
| | pCDNAI-α(1,2)FTSe | 3.8 |
| | Secretor | 5.7 |
| | Secretor | 36 |
| GDP-fucose | H | 0.016, 0.018 |
| | H | 0.027 |
| | H | 0.008 |
| | pCDNAI-α(1,2)FTSe | 0.197 |
| | Secretor | 0.108 |
| | Secretor | 0.123 |

Figure 10E:
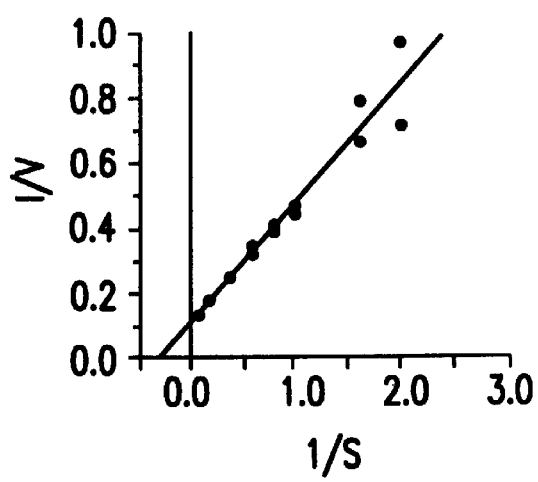
Figure 10F:
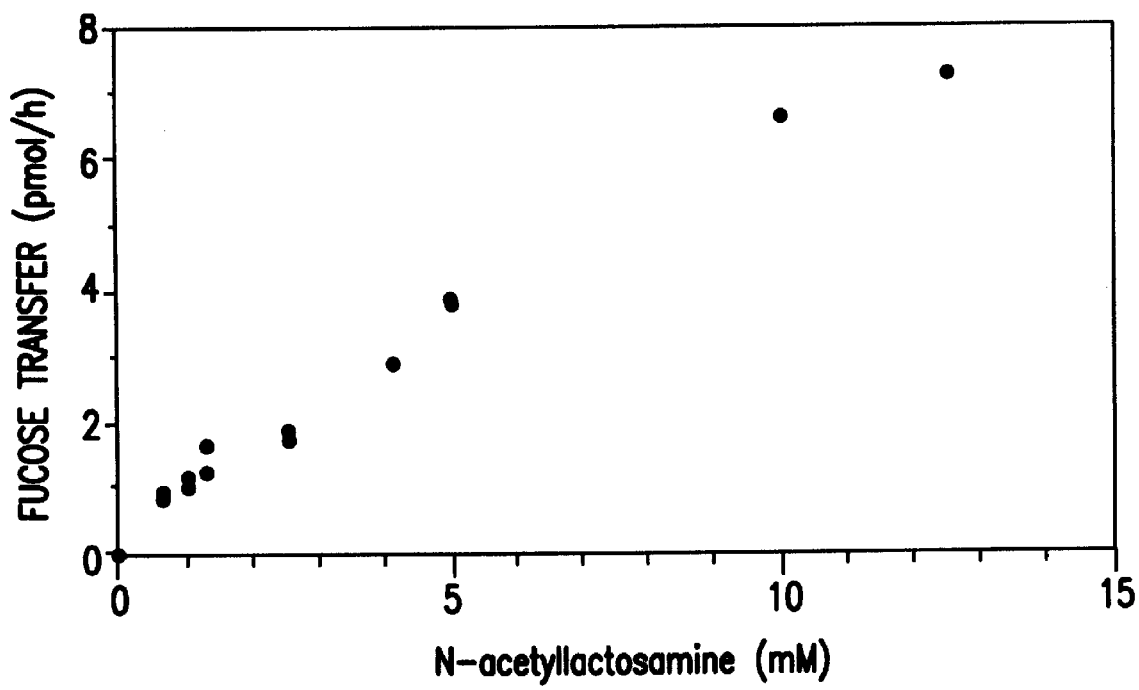
Figure 10G:
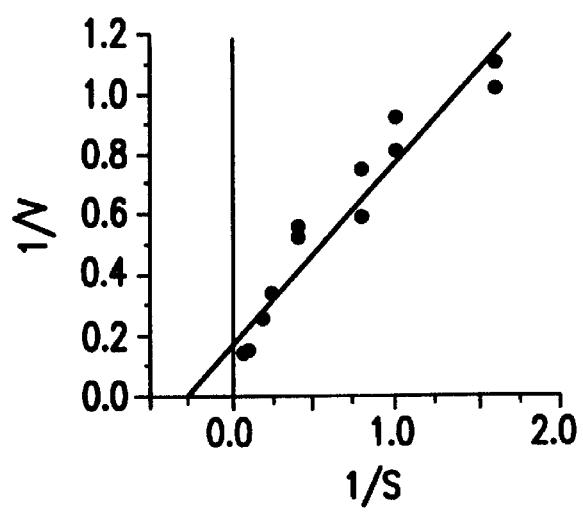
Figure 10H:
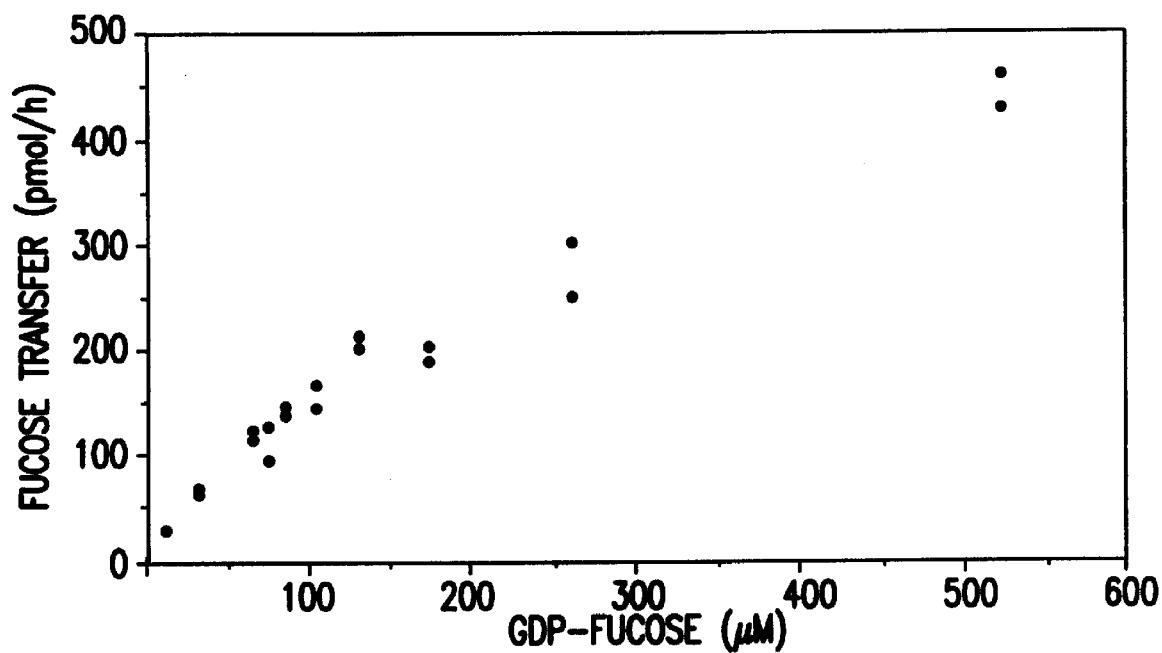
Figure 10I:
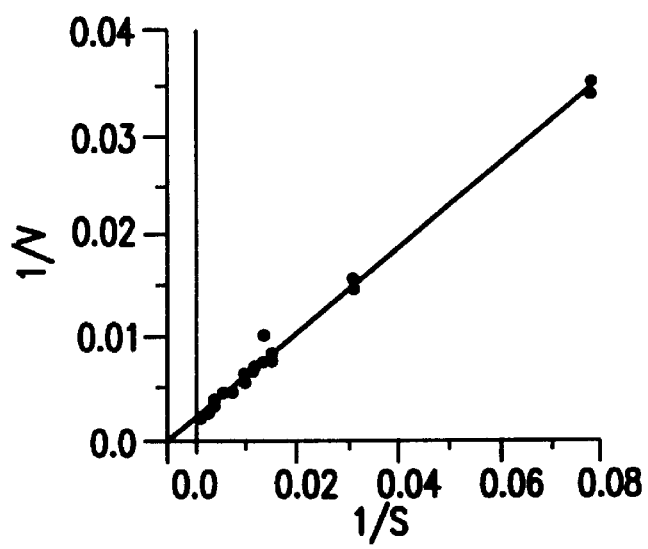

Likewise, this enzyme exhibits an apparent $K_m$ of 197 μM for the substrate GDP-fucose (FIG. 10e). This is similar to the relatively high apparent Michaelis constant for this substrate reported previously (Sarnesto, A., Kohlin, T., Hindsgaul, O., Thurin, J., and Blaszczyk-Thurin, M., *J. Biol. Chem.*, vol. 267, 2737–2744 (1992), Rajan, V. P., Larsen, R. D., Ajmera, S., Ernst, L. K., and Lowe, J. B., *J. Biol. Chem.*, vol. 264, 11158–11167 (1989)) for an α(1,2) fucosyltransferase activity believed to be encoded by the Secretor locus (Table I).

The Secretor locus-determined α(1,2)fucosyltransferase activity is detectable in soluble form in milk, and in other body fluids (Oriol, R., *J. Immunogenet.*, vol. 17, 235–245 (1990), Chester, M. A., Yates, A. D., and Watkins, W. M., *Eur. J. Biochem.*, vol. 69, 583–592 (1976)). To determine if this biosynthetic process is recapitulated in COS-7 cells, COS-7 cells were transfected with pCDNAI-α(1,2)FTSe-short, or with pCDNAI-α(1,2)FTSe-long, and the cell-associated and soluble α(1,2)fucosyltransferase activity produced by each vector (see "Materials and Methods") was quantitated. Media isolated from a 100 mm dish of COS-7 cells transfected with pCDNAI-α(1,2)FTSe-short contained approximately 868 total units of activity. By contrast, the cell extract prepared from the same plate of transfected cells contained approximately 118 total units of α(1,2) fucosyltransferase activity, for a media/cell extract ratio of approximately 7.4. Similar results were obtained when pCDNAI-α(1,2)FTSe-long was used in these experiments (357 units in media, versus 55 units in cell extract; media/ cell extract ratio of approximately 6.5). These data indicate that both forms of this enzyme are released from the transfected COS-7 cells in a relatively efficient manner. This contrasts with the H blood group cDNA-encoded α(1,2) fucosyltransferase activity, which is largely cell-associated when expressed in COS-7 cells (Larsen, R. D., Ernst, L. K., Nair, R. P. and Lowe, J. B., *Proc. Natl. Acad. Sci. USA*, vol. 87, 6674–6678 (1990)).

In aggregate, these data confirm that the Sec2 segment encodes an α(1,2)fucosyltransferase. They are also consistent with the hypothesis that this sequence corresponds to an α(1,2)fucosyltransferase locus, presumed to be the Secretor blood group locus, that encodes an α(1,2)fucosyltransferase found in the serum and milk of secretor-positive individuals.

A naturally-occuring nonsense mutation (Trp149→ter) yields an inactive Sec2 allele It is well established that approximately 20% of humans are homozygous for null alleles at the Secretor locus (Mourant, A. E., Kopèc, A. C., and Domaniewska-Sobczak, K., *The distribution of the human blood groups and other biochemical polymorphisms*, 2nd Ed., Oxford University Press, London. (1976), Gaensslen, R. E., Bell, S. C., and Lee, H. C., *J. of Forensic Sciences*, vol. 32, 1016–1058 (1987)). Naturally-occuring coding sequence mutations yield null alleles at other blood group glycosyltransferase loci, including the human ABO (Yamamoto, F-I., Clausen, H., White, T., Marken, J., and Hakomori, S-I., *Nature*, vol. 345, 229–233) (1990), H (Kelly, R. J., Ernst, L. K., Larsen, R. D., Bryant, J. G., Robinson, J. S. and Lowe, J. B., *Proc. Natl. Acad. Sci. USA* vol. 91, 5843–5847 (1994)) and Lewis (Mollicone, R., Reguigne, I., Kelly, R. J., Fletcher, A., Watt, J., Chatfield, S., Aziz, A., Cameron, H. S., Weston, B. W., Lowe, J. B., and Oriol, R. (1994) *J. Biol Chem.*, vol. 269, 20987–20994) blood group loci. During the course of DNA sequence analysis of alleles corresponding to the Sec2 DNA fragment, a DNA sequence polymorphism that yields a translation termination codon within the open reading frame in Sec2, as shown in FIG. 9 was identified. This DNA sequence polymorphism corresponds to the tryptophan residue at codon number 143 (numbered from the putative initiator methionine of the "short" protein, FIG. 9), yields a stop codon at this position, and is predicted to truncate a large part (189 amino acid residues) of the enzyme's COOH terminal segment.

To determine if this polymorphism yields an inactive allele, the expression vector pCDNAI-α(1,2)FTse ("Materials and Methods"), containing the termination codon at position 143, was tested by transfection for its ability to encode a functional α(1,2)fucosyltransferase. No α(1,2)fucosyltransferase activity was detected in COS-7 cells transfected with vector pCDNAI-α(1,2)FTse. One other DNA sequence polymorphism that yields a protein coding sequence alteration is also present in the Trp143→ter allele derived from cosmid 31553 (Gly247→Ser; FIG. 9). An expression vector (pcDNAI-α(1,2)FTSe-int, "Materials and Methods") containing this other amino acid sequence polymorphism, on the wild type sequence background, was constructed and tested for its ability to express α(1,2) fucosyltransferase activity. This vector determined expression of wild type levels of α(1,2)fucosyltransferase activity when expressed in COS-7 cells. The results indicate that the DNA sequence polymorphism that creates the translation termination codon inactivates this allele, whereas the other polymorphism is functionally neutral in a qualitative α(1,2)fucosyltransferase activity assay.

The frequency of the Trp43→ter mutation corresponds to the frequency of the se allele, and is present in double dose in non-secretors but not in secretor-positive individuals Allele-specific oligonucleotide analyses (FIG. 11a) indicated that 10 of 52 unselected, unrelated individuals were homozygous for the Trp143→ter null allele. This frequency (19%) is virtually identical to the frequency of the non-secretor phenotype in most populations (~20%, refs. Mourant, A. E., Kopec, A. C., and Domaniewska-Sobczak, K., *The distribution of the human blood groups and other biochemical polymorphisms*, 2nd Ed., Oxford University Press, London. (1976), Gaensslen, R. E., Bell, S. C., and Lee, H. C., *J. of Forensic Sciences*, vol. 32, 1016–1058 (1987)). The remaining persons maintain at least one functional allele at this locus, an observation consistent with the possibility that these persons are secretor-positive by virtue of maintaining at least one functional copy of the Sec2 locus.

To further explore the possibility that homozygosity for the Trp143→ter null allele is commonly responsible for the non-secretor phenotype, the Sec2 sequence at this position in a group of individuals whose secretor phenotypes had been previously determined ("Materials and Methods") was analyzed. Each of six non-secretor individuals were found to be homozygous for the Trp143→ter null allele, whereas all secretor-positive persons were found to maintain at least one wild type allele at codon 143 (FIG. 11b). Taken together with the physical linkage analyses and the biochemical analyses, these genetic results lead us to conclude that the Sec2 locus corresponds to a structural gene encoding the Secretor locus α(1,2)fucosyltransferase. They further indicate that the non-secretor phenotype is often, though perhaps not exclusively, due to homozygosity for a common Trp143→ter null allele at this locus.

A low stringency hybridization screen of two chromosome 19 specific cosmid libraries with the FUT1 cDNA yielded one cosmid clone (31553) containing the 8.2 kb EcoRI fragment. The cross-hybridizing sequence in this fragment has been termed Sec1. It was also found that cosmid 31553 contains a second, distinct cross-hybridizing sequence that was termed Sec2. This sequence is found on an 18.5 kb EcoRI fragment. This 18.5 kb EcoRI fragment was not detectable on human genomic Southern blots probed at low stringency with the FUT1 cDNA.

To determine if either of these two sequences were transcribed, an hybrid selection strategy (Parimoo, S., Patanjali, S. R., Shukla, H., Chaplin, D. D. and Weissman, S. M., *Proc. Natl. Acad. Sci. USA*, vol. 88, 9623–9627 (1991), Lovett, M., Kere, J. and Hinton, L., *Proc. Natl. Acad. Sci. USA*, vol. 88, 9628–9632 (1991), Morgan, J. G., Dolganov, G. M., Robbins, S. E., Hinton, L. M. and Lovett, M., *Nuc. Acids Res.*, vol. 20, 5173–5179 (1992), Korn, B., Sedlacek, Zdenek, Manca, A., Kioschis, P., Konecki, D., Lehrach, H. and Poustka, A., *Human Molec. Genet.*, vol. 1, 235–242 (1992), Tagle, D. A., Swaroop, M., Lovett, M. and Collins, F., *Nature*, vol. 361, 751–753 (1993)) capable of isolating cDNAs corresponding to non-abundant transcripts emanating from genes whose boundaries fall within cosmid 31553 was used. This approach yielded a ~500 bp cDNA that hybridizes only with the Sec2-containing 18.5 kb EcoRI fragment. Northern blot analyses demonstrate that this cDNA detects mRNA transcripts in small intestine, colon, and lung, but not in liver or kidney. Sequence analysis of this cDNA, and of the corresponding genomic DNA region of Sec2, indicates that this cDNA is derived from the 3' untranslated region of a novel human α(1,2)fucosyltransferase gene. Since previous observations indicate that the Secretor α(1,2)fucosyltransferase gene is expressed in secretory epithelia (Le Pendu, J., Cartron, J. P., Lemieux, R. U. and Oriol, R., *Am. J. Hum. Genet.*, vol. 37, 749–760 (1985)), these results are consistent with the possibility that Sec2 corresponds to the human Secretor (FUT2) blood group locus.

No transcripts corresponding to Sec1 were detected, and no cDNAs corresponding to this sequence by the hybrid selection approach were isolated. These observations suggest that Sec1 might represent a pseudogene. This conclusion is supported by DNA sequence data for Sec1.

A physical mapping strategy was used to position the FUT1 (H) gene and the two FUT1-related sequences along a 100 kb region of human chromosome 19. This map indicates that FUT1 and the Sec2 locus are separated by a distance of roughly 35 kb. Since previous linkage analyses (Oriol, R., Danilovs, J. and Hawkins, B. R., *Am. J. Hum. Genet.*, vol. 33, 421–431 (1981); Le Pendu, J., Cartron, J. P., Lemieux, R. U. and Oriol, R., *Am. J. Hum. Genet.*, vol. 37, 749–760 (1985); Kelly, R. J., Ernst, L. K., Larsen, R. D., Bryant, J. G., Robinson, J. S. and Lowe, J. B., *Proc. Natl. Acad. Sci. USA*, vol. 91, 5843–5847 (1994); Oriol, R., Le Pendu, J., Bernez, L. Lambert, F., Dalix, A. M. and Hawkins, B. R., *Cytogenet. Cell. Genet.*, vol. 37, 564 (1984)) have established that the H and Secretor loci are closely linked on 19q, the close physical proximity of the FUT1 and Sec2 loci is also consistent with the studies here that assign Sec2 to the Secretor locus.

The positions of these sequences is also consistent with biochemical studies suggesting that the H locus arose via a gene duplication from an ancestral Secretor-type α(1,2) fucosyltransferase gene (Le Pendu, J., Cartron, J. P., Lemieux, R. U. and Oriol, R., *Am. J. Hum. Genet.*, vol. 37, 749–760 (1985)). This situation is analogous to that observed for members of human α(1,3)fucosyltransferase genes, that cluster on the short arm of chromosome 19 (Lowe, J. B., Kukowska-Latallo, J. F., Nair, R. P., Larsen, R. D., Marks, R. M., Macher, B. A., Kelly, R. J. and Ernst, L., *J. Biol. Chem.*, vol. 266, 17467–17477 (1991); Weston, B. W., Nair, R. P., Larsen, R. D. and Lowe, J. B., *J. Biol. Chem.*, vol. 267, 4152–4160 (1992); Weston, B. W., Smith, P. L., Kelly, R. J. and Lowe, J. B., *J. Biol. Chem.*, vol. 267, 24575–24584 (1992); Kukowska-Latallo, J. F., Larsen, R. D., Nair, R. P. and Lowe, J. B., *Genes & Dev.* 4, 1288–1303 (1990), Nishihara, S., Nakazato, M., Kudo, T., Kimura, H., Ando, T. and Narimatsu, H., *Biochem. Biophys. Res. Commun.*, vol. 190, 42–46 (1993)).

The present results indicate that the Sec2 DNA segment corresponds to the human Secretor blood group locus. They also confirm the hypothesis (Oriol, R., *J. Immunogenet.*, vol. 17, 235–245 (1990)) that the H and Secretor loci represent two distinct but closely linked α(1,2)fucosyltransferase loci, and demonstrate, with other data (Kelly, R. J., Ernst, L. K., Larsen, R. D., Bryant, J. G., Robinson, J. S. and Lowe, J. B., *Proc. Natl. Acad. Sci. USA*, vol. 91, 5843–5847 (1994)), that homozygosity for null alleles at these two loci can explain virtually all known recessively-inherited H-deficient phenotypes in humans.

The abbreviations used are: α(1,2) fucosyltransferase, GDP-L-fucose:β-D-galactoside 2-α-L-fucosyltransferase; α(1,3) fucosyltransferase, GDP-fucose:µ-D-N-acetylglucosaminide 3-α-L-fucosyltransferase; PCR, polymerase chain reaction; bp, base pair(s), kb, kilobase(s); Mb, Megabase.

The plasmids pCDNAI-Se2 and pCDNAI-α(1,2)FT Se-short were deposited at the American Type Culture Collection, 12301 Parklawn Drive, Rockville, Md., 20852 USA on Feb. 28, 1995.

Obviously, numerous modifications and variations of the present invention are possible in light of the above teachings. It is therefore to be understood that, within the scope of the appended claims, the invention may be practiced otherwise than as specifically described herein.

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
        ( A ) LENGTH: 1144 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 56..721

( i x ) FEATURE:
        ( A ) NAME/KEY: CDS
        ( B ) LOCATION: 723..1097

( x i ) SEQUENCE DESCRIPTION: SEQ ID NO:1:

```
CTTTGGCAGG  GGGTGGGTGA  AGAGACTCCT  GTCCCCCCAG  CCCTGCCTCC  TGACC ATG       58
                                                                  Met
                                                                    1

TCC  TCT  CTC  CTC  CCC  ACA  GCC  GTC  AAG  GGA  TTC  TGG  GCC  ACC  CGC  CCT      106
Ser  Ser  Leu  Leu  Pro  Thr  Ala  Val  Lys  Gly  Phe  Trp  Ala  Thr  Arg  Pro
               5                   10                       15

TCC  TTC  TCC  ACC  TTC  TAC  TTC  GTC  TTT  GCC  ATT  TTT  GTG  GTG  TCC  ACC      154
Ser  Phe  Ser  Thr  Phe  Tyr  Phe  Val  Phe  Ala  Ile  Phe  Val  Val  Ser  Thr
          20                        25                       30

ATC  TTT  CAC  TGC  CAC  CAG  CAC  CTG  GCT  CTG  GTG  CCT  GCG  CCC  TGG  GCA      202
Ile  Phe  His  Cys  His  Gln  His  Leu  Ala  Leu  Val  Pro  Ala  Pro  Trp  Ala
     35                        40                        45

TAC  TCA  GCC  CGT  GTG  GTC  CTG  GCC  CCC  AGA  CAC  CTG  CCC  CGG  GAG  GAC      250
Tyr  Ser  Ala  Arg  Val  Val  Leu  Ala  Pro  Arg  His  Leu  Pro  Arg  Glu  Asp
50                       55                        60                       65

CTG  TTC  ACT  ATC  AAC  TCC  AAG  GGC  CGC  CTG  GGG  AAC  CAG  ATG  GGC  GAG      298
Leu  Phe  Thr  Ile  Asn  Ser  Lys  Gly  Arg  Leu  Gly  Asn  Gln  Met  Gly  Glu
                    70                       75                        80

TAC  GCC  ACG  CTG  TAC  GCC  CTG  GCC  AAG  ATG  AAC  GGG  CGG  CCC  GCC  TTC      346
Tyr  Ala  Thr  Leu  Tyr  Ala  Leu  Ala  Lys  Met  Asn  Gly  Arg  Pro  Ala  Phe
               85                        90                       95

ATC  CCG  GCC  CAG  ATG  CAC  AGC  AGG  GTG  GCC  CCC  ATC  TTC  AGA  ATC  ACC      394
Ile  Pro  Ala  Gln  Met  His  Ser  Arg  Val  Ala  Pro  Ile  Phe  Arg  Ile  Thr
          100                      105                      110

CTG  CCG  GTG  CTG  CAC  AGC  GCC  ACG  GCC  AGC  AGG  ATC  CCC  TGG  CAG  AAC      442
Leu  Pro  Val  Leu  His  Ser  Ala  Thr  Ala  Ser  Arg  Ile  Pro  Trp  Gln  Asn
     115                      120                      125

TAC  CAC  CTG  AAC  GAC  TGG  ATG  GAG  GAG  GAG  TAC  CGC  CAC  ATC  CCG  GGG      490
Tyr  His  Leu  Asn  Asp  Trp  Met  Glu  Glu  Glu  Tyr  Arg  His  Ile  Pro  Gly
130                      135                      140                      145
```

```
CGC  TGT  GTC  CAC  CTC  ACG  GGC  TAC  CCC  TGC  TCC  TGG  ACC  TTC  TAC  CAC    538
Arg  Cys  Val  His  Leu  Thr  Gly  Tyr  Pro  Cys  Ser  Trp  Thr  Phe  Tyr  His
               150                      155                      160

CAC  CTC  CGC  CAG  GAG  ATC  CTC  CAG  GAG  TTC  ACC  CTG  CAC  GAC  CAC  GTG    586
His  Leu  Arg  Gln  Glu  Ile  Leu  Gln  Glu  Phe  Thr  Leu  His  Asp  His  Val
               165                      170                      175

CGC  GAG  GAG  GCC  CAG  AAG  TTC  CTG  CGG  GGC  CTG  CAG  GCC  AAG  TGG  GCA    634
Arg  Glu  Glu  Ala  Gln  Lys  Phe  Leu  Arg  Gly  Leu  Gln  Ala  Lys  Trp  Ala
               180                      185                      190

GGG  CAG  GCG  ACC  TTC  GTG  GGG  GTC  CAC  GTG  CGC  CGG  GGG  GAC  TAT  GTC    682
Gly  Gln  Ala  Thr  Phe  Val  Gly  Val  His  Val  Arg  Arg  Gly  Asp  Tyr  Val
               195                      200                      205

CGT  GTC  ATG  CCG  CGC  GTA  TGG  AAG  GGG  GTG  CTG  GCC  GAC  C    GGC  TAC    728
Arg  Val  Met  Pro  Arg  Val  Trp  Lys  Gly  Val  Leu  Ala  Asp       Gly  Tyr
210                           215                      220                 1

CTG  CAG  CGG  GCC  CTG  GAC  TGG  TTC  CGG  GCC  TGC  TGC  CGC  CTC  CCG  GTC    776
Leu  Gln  Arg  Ala  Leu  Asp  Trp  Phe  Arg  Ala  Cys  Cys  Arg  Leu  Pro  Val
          5                        10                       15

TTT  GTG  GTC  ACC  AGC  GAT  GAC  ATG  GCC  TGG  TGC  CGG  GAG  AGC  ATC  AAC    824
Phe  Val  Val  Thr  Ser  Asp  Asp  Met  Ala  Trp  Cys  Arg  Glu  Ser  Ile  Asn
          20                       25                       30

AGC  TCC  CTT  GGG  GAC  GTG  GTG  TTC  GCT  GGC  AAT  GGC  CTC  CAG  GGC  TCA    872
Ser  Ser  Leu  Gly  Asp  Val  Val  Phe  Ala  Gly  Asn  Gly  Leu  Gln  Gly  Ser
35                       40                       45                       50

CCT  GCC  AAG  GAC  TTC  GCA  CTG  CTC  ACA  CAG  TGC  AAC  CAC  ACC  ATC  ATC    920
Pro  Ala  Lys  Asp  Phe  Ala  Leu  Leu  Thr  Gln  Cys  Asn  His  Thr  Ile  Ile
                    55                       60                       65

ACC  GTG  GGC  ACC  TTC  GGG  GTC  TGG  GCC  GCG  TAC  CTC  GCG  GGC  GGG  GAC    968
Thr  Val  Gly  Thr  Phe  Gly  Val  Trp  Ala  Ala  Tyr  Leu  Ala  Gly  Gly  Asp
               70                       75                       80

ACT  GTC  TAC  CTG  GCC  AAC  TTC  ACC  CTG  CCC  AAC  TCC  CCT  TTC  AAC  GTG   1016
Thr  Val  Tyr  Leu  Ala  Asn  Phe  Thr  Leu  Pro  Asn  Ser  Pro  Phe  Asn  Val
          85                       90                       95

GTC  TTT  AGG  CCG  TAA  GCG  GCC  TTC  CTG  CCA  GAG  TGG  GTG  GGC  CTT  GCG   1064
Val  Phe  Arg  Pro  *    Ala  Ala  Phe  Leu  Pro  Glu  Trp  Val  Gly  Leu  Ala
     100                      105                      110

GCT  GAC  CTT  GGA  CAG  GCT  GGA  CAG  AAC  GGC  CTC  TAGCCAGCCC TGCATGTGCC     1117
Ala  Asp  Leu  Gly  Gln  Ala  Gly  Gln  Asn  Gly  Leu
115                      120                      125

TGGTCCTCAT CCTGTGACCC GAGGGGC                                                    1144
```

( 2 ) INFORMATION FOR SEQ ID NO:2:

( i ) SEQUENCE CHARACTERISTICS:
        ( A ) LENGTH: 222 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Ser  Ser  Leu  Leu  Pro  Thr  Ala  Val  Lys  Gly  Phe  Trp  Ala  Thr  Arg
1                   5                        10                       15

Pro  Ser  Phe  Ser  Thr  Phe  Tyr  Phe  Val  Phe  Ala  Ile  Phe  Val  Val  Ser
               20                       25                       30

Thr  Ile  Phe  His  Cys  His  Gln  His  Leu  Ala  Leu  Val  Pro  Ala  Pro  Trp
          35                       40                       45

Ala  Tyr  Ser  Ala  Arg  Val  Val  Leu  Ala  Pro  Arg  His  Leu  Pro  Arg  Glu
     50                       55                       60
```

```
Asp  Leu  Phe  Thr  Ile  Asn  Ser  Lys  Gly  Arg  Leu  Gly  Asn  Gln  Met  Gly
 65                  70                  75                            80

Glu  Tyr  Ala  Thr  Leu  Tyr  Ala  Leu  Ala  Lys  Met  Asn  Gly  Arg  Pro  Ala
                85                       90                            95

Phe  Ile  Pro  Ala  Gln  Met  His  Ser  Arg  Val  Ala  Pro  Ile  Phe  Arg  Ile
               100                      105                      110

Thr  Leu  Pro  Val  Leu  His  Ser  Ala  Thr  Ala  Ser  Arg  Ile  Pro  Trp  Gln
               115                      120                      125

Asn  Tyr  His  Leu  Asn  Asp  Trp  Met  Glu  Glu  Glu  Tyr  Arg  His  Ile  Pro
          130                 135                      140

Gly  Arg  Cys  Val  His  Leu  Thr  Gly  Tyr  Pro  Cys  Ser  Trp  Thr  Phe  Tyr
145                      150                      155                      160

His  His  Leu  Arg  Gln  Glu  Ile  Leu  Gln  Glu  Phe  Thr  Leu  His  Asp  His
                    165                      170                      175

Val  Arg  Glu  Glu  Ala  Gln  Lys  Phe  Leu  Arg  Gly  Leu  Gln  Ala  Lys  Trp
               180                      185                      190

Ala  Gly  Gln  Ala  Thr  Phe  Val  Gly  Val  His  Val  Arg  Arg  Gly  Asp  Tyr
          195                      200                      205

Val  Arg  Val  Met  Pro  Arg  Val  Trp  Lys  Gly  Val  Leu  Ala  Asp
210                      215                      220
```

( 2 ) INFORMATION FOR SEQ ID NO:3:

( i ) SEQUENCE CHARACTERISTICS:
        ( A ) LENGTH: 102 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

```
Gly  Tyr  Leu  Gln  Arg  Ala  Leu  Asp  Trp  Phe  Arg  Ala  Cys  Cys  Arg  Leu
 1                   5                   10                            15

Pro  Val  Phe  Val  Val  Thr  Ser  Asp  Asp  Met  Ala  Trp  Cys  Arg  Glu  Ser
                20                       25                      30

Ile  Asn  Ser  Ser  Leu  Gly  Asp  Val  Val  Phe  Ala  Gly  Asn  Gly  Leu  Gln
           35                       40                      45

Gly  Ser  Pro  Ala  Lys  Asp  Phe  Ala  Leu  Leu  Thr  Gln  Cys  Asn  His  Thr
      50                       55                      60

Ile  Ile  Thr  Val  Gly  Thr  Phe  Gly  Val  Trp  Ala  Ala  Tyr  Leu  Ala  Gly
 65                       70                      75                       80

Gly  Asp  Thr  Val  Tyr  Leu  Ala  Asn  Phe  Thr  Leu  Pro  Asn  Ser  Pro  Phe
                85                       90                      95

Asn  Val  Val  Phe  Arg  Pro
               100
```

( 2 ) INFORMATION FOR SEQ ID NO:4:

( i ) SEQUENCE CHARACTERISTICS:
        ( A ) LENGTH: 22 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Ala  Ala  Phe  Leu  Pro  Glu  Trp  Val  Gly  Leu  Ala  Ala  Asp  Leu  Gly  Gln
 1                   5                         10                           15

Ala  Gly  Gln  Asn  Gly  Leu
                20
```

( 2 ) INFORMATION FOR SEQ ID NO:5:

( i ) SEQUENCE CHARACTERISTICS:
        ( A ) LENGTH: 1199 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 51..1145

( x i ) SEQUENCE DESCRIPTION: SEQ ID NO:5:

```
CCTCCTCAGC CTCAGTGCAT TTGCTAATTC GCCTTTCCTC CCCTGCAGCC ATG TGG          56
                                                        Met Trp

CTC CGG AGC CAT CGT CAG CTC TGC CTG GCC TTC CTG CTA GTC TGT GTC         104
Leu Arg Ser His Arg Gln Leu Cys Leu Ala Phe Leu Leu Val Cys Val
        130             135                 140

CTC TCT GTA ATC TTC TTC CTC CAT ATC CAT CAA GAC AGC TTT CCA CAT         152
Leu Ser Val Ile Phe Phe Leu His Ile His Gln Asp Ser Phe Pro His
145             150                 155

GGC CTA GGC CTG TCG ATC CTG TGT CCA GAC CGC CGC CTG GTG ACA CCC         200
Gly Leu Gly Leu Ser Ile Leu Cys Pro Asp Arg Arg Leu Val Thr Pro
160             165                 170                     175

CCA GTG GCC ATC TTC TGC CTG CCG GGT ACT GCG ATG GGC CCC AAC GCC         248
Pro Val Ala Ile Phe Cys Leu Pro Gly Thr Ala Met Gly Pro Asn Ala
                180             185                 190

TCC TCT TCC TGT CCC CAG CAC CCT GCT TCC CTC TCC GGC ACC TGG ACT         296
Ser Ser Ser Cys Pro Gln His Pro Ala Ser Leu Ser Gly Thr Trp Thr
            195             200             205

GTC TAC CCC AAT GGC CGG TTT GGT AAT CAG ATG GGA CAG TAT GCC ACG         344
Val Tyr Pro Asn Gly Arg Phe Gly Asn Gln Met Gly Gln Tyr Ala Thr
        210                 215                 220

CTG CTG GCT CTG GCC CAG CTC AAC GGC CGC CGG GCC TTT ATC CTG CCT         392
Leu Leu Ala Leu Ala Gln Leu Asn Gly Arg Arg Ala Phe Ile Leu Pro
225                 230                 235

GCC ATG CAT GCC GCC CTG GCC CCG GTA TTC CGC ATC ACC CTG CCC GTG         440
Ala Met His Ala Ala Leu Ala Pro Val Phe Arg Ile Thr Leu Pro Val
240             245                 250                     255

CTG GCC CCA GAA GTG GAC AGC CGC ACG CCG TGG CGG GAG CTG CAG CTT         488
Leu Ala Pro Glu Val Asp Ser Arg Thr Pro Trp Arg Glu Leu Gln Leu
                260             265                 270

CAC GAC TGG ATG TCG GAG GAG TAC GCG GAC TTG AGA GAT CCT TTC CTG         536
His Asp Trp Met Ser Glu Glu Tyr Ala Asp Leu Arg Asp Pro Phe Leu
            275             280                 285

AAG CTC TCT GGC TTC CCC TGC TCT TGG ACT TTC TTC CAC CAT CTC CGG         584
Lys Leu Ser Gly Phe Pro Cys Ser Trp Thr Phe Phe His His Leu Arg
        290                 295                 300

GAA CAG ATC CGC AGA GAG TTC ACC CTG CAC GAC CAC CTT CGG GAA GAG         632
Glu Gln Ile Arg Arg Glu Phe Thr Leu His Asp His Leu Arg Glu Glu
305                 310                 315

GCG CAG AGT GTG CTG GGT CAG CTC CGC CTG GGC CGC ACA GGG GAC CGC         680
Ala Gln Ser Val Leu Gly Gln Leu Arg Leu Gly Arg Thr Gly Asp Arg
320             325                 330                     335

CCG CGC ACC TTT GTC GGC GTC CAC GTG CGC CGT GGG GAC TAT CTG CAG         728
Pro Arg Thr Phe Val Gly Val His Val Arg Arg Gly Asp Tyr Leu Gln
                340             345                 350

GTT ATG CCT CAG CGC TGG AAG GGT GTG GTG GGC GAC AGC GCC TAC CTC         776
Val Met Pro Gln Arg Trp Lys Gly Val Val Gly Asp Ser Ala Tyr Leu
            355                 360                 365
```

| | | | | | | | | | | | | | | | | |
|---|---|---|---|---|---|---|---|---|---|---|---|---|---|---|---|---|
| CGG | CAG | GCC | ATG | GAC | TGG | TTC | CGG | GCA | CGG | CAC | GAA | GCC | CCC | GTT | TTC | 824 |
| Arg | Gln | Ala | Met | Asp | Trp | Phe | Arg | Ala | Arg | His | Glu | Ala | Pro | Val | Phe | |
| | | 370 | | | | | 375 | | | | | 380 | | | | |
| GTG | GTC | ACC | AGC | AAC | GGC | ATG | GAG | TGG | TGT | AAA | GAA | AAC | ATC | GAC | ACC | 872 |
| Val | Val | Thr | Ser | Asn | Gly | Met | Glu | Trp | Cys | Lys | Glu | Asn | Ile | Asp | Thr | |
| 385 | | | | | | 390 | | | | | 395 | | | | | |
| TCC | CAG | GGC | GAT | GTG | ACG | TTT | GCT | GGC | GAT | GGA | CAG | GAG | GCT | ACA | CCG | 920 |
| Ser | Gln | Gly | Asp | Val | Thr | Phe | Ala | Gly | Asp | Gly | Gln | Glu | Ala | Thr | Pro | |
| 400 | | | | 405 | | | | | 410 | | | | | | 415 | |
| TGG | AAA | GAC | TTT | GCC | CTG | CTC | ACA | CAG | TGC | AAC | CAC | ACC | ATT | ATG | ACC | 968 |
| Trp | Lys | Asp | Phe | Ala | Leu | Leu | Thr | Gln | Cys | Asn | His | Thr | Ile | Met | Thr | |
| | | | | 420 | | | | | 425 | | | | | 430 | | |
| ATT | GGC | ACC | TTC | GGC | TTC | TGG | GCT | GCC | TAC | CTG | GCT | GGC | GGA | GAC | ACT | 1016 |
| Ile | Gly | Thr | Phe | Gly | Phe | Trp | Ala | Ala | Tyr | Leu | Ala | Gly | Gly | Asp | Thr | |
| | | | 435 | | | | | 440 | | | | | 445 | | | |
| GTC | TAC | CTG | GCC | AAC | TTC | ACC | CTG | CCA | GAC | TCT | GAG | TTC | CTG | AAG | ATC | 1064 |
| Val | Tyr | Leu | Ala | Asn | Phe | Thr | Leu | Pro | Asp | Ser | Glu | Phe | Leu | Lys | Ile | |
| | | 450 | | | | | 455 | | | | | 460 | | | | |
| TTT | AAG | CCG | GAG | GCG | GCC | TTC | CTG | CCC | GAG | TGG | GTG | GGC | ATT | AAT | GCA | 1112 |
| Phe | Lys | Pro | Glu | Ala | Ala | Phe | Leu | Pro | Glu | Trp | Val | Gly | Ile | Asn | Ala | |
| | 465 | | | | | 470 | | | | | 475 | | | | | |
| GAC | TTG | TCT | CCA | CTC | TGG | ACA | TTG | GCT | AAG | CCT | TGAGAGCCAG | | GGAGACTTTC | | | 1165 |
| Asp | Leu | Ser | Pro | Leu | Trp | Thr | Leu | Ala | Lys | Pro | | | | | | |
| 480 | | | | | 485 | | | | | 490 | | | | | | |
| TGAAGTAGCC | | TGATCTTTCT | | AGAGCCAGCA | | GTAC | | | | | | | | | | 1199 |

( 2 ) INFORMATION FOR SEQ ID NO:6:

( i ) SEQUENCE CHARACTERISTICS:
        ( A ) LENGTH: 365 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| | | | | | | | | | | | | | | |
|---|---|---|---|---|---|---|---|---|---|---|---|---|---|---|
| Met | Trp | Leu | Arg | Ser | His | Arg | Gln | Leu | Cys | Leu | Ala | Phe | Leu | Leu | Val |
| 1 | | | | 5 | | | | | 10 | | | | | 15 | |
| Cys | Val | Leu | Ser | Val | Ile | Phe | Phe | Leu | His | Ile | His | Gln | Asp | Ser | Phe |
| | | | | 20 | | | | | 25 | | | | | 30 | |
| Pro | His | Gly | Leu | Gly | Leu | Ser | Ile | Leu | Cys | Pro | Asp | Arg | Leu | Val | |
| | | | 35 | | | | | 40 | | | | | 45 | | |
| Thr | Pro | Pro | Val | Ala | Ile | Phe | Cys | Leu | Pro | Gly | Thr | Ala | Met | Gly | Pro |
| | 50 | | | | | 55 | | | | | 60 | | | | |
| Asn | Ala | Ser | Ser | Ser | Cys | Pro | Gln | His | Pro | Ala | Ser | Leu | Ser | Gly | Thr |
| 65 | | | | | 70 | | | | | 75 | | | | | 80 |
| Trp | Thr | Val | Tyr | Pro | Asn | Gly | Arg | Phe | Gly | Asn | Gln | Met | Gly | Gln | Tyr |
| | | | | 85 | | | | | 90 | | | | | 95 | |
| Ala | Thr | Leu | Leu | Ala | Leu | Ala | Gln | Leu | Asn | Gly | Arg | Arg | Ala | Phe | Ile |
| | | | 100 | | | | | 105 | | | | | 110 | | |
| Leu | Pro | Ala | Met | His | Ala | Ala | Leu | Ala | Pro | Val | Phe | Arg | Ile | Thr | Leu |
| | | 115 | | | | | 120 | | | | | 125 | | | |
| Pro | Val | Leu | Ala | Pro | Glu | Val | Asp | Ser | Arg | Thr | Pro | Trp | Arg | Glu | Leu |
| | 130 | | | | | 135 | | | | | 140 | | | | |
| Gln | Leu | His | Asp | Trp | Met | Ser | Glu | Glu | Tyr | Ala | Asp | Leu | Arg | Asp | Pro |
| 145 | | | | | 150 | | | | | 155 | | | | | 160 |
| Phe | Leu | Lys | Leu | Ser | Gly | Phe | Pro | Cys | Ser | Trp | Thr | Phe | Phe | His | His |
| | | | | 165 | | | | | 170 | | | | | 175 | |

| | | | | | | | | | | | | | | |
|---|---|---|---|---|---|---|---|---|---|---|---|---|---|---|
| Leu | Arg | Glu | Gln | Ile | Arg | Arg | Glu | Phe | Thr | Leu | His | Asp | His | Leu | Arg |
| | | | 180 | | | | 185 | | | | | 190 | | | |
| Glu | Glu | Ala | Gln | Ser | Val | Leu | Gly | Gln | Leu | Arg | Leu | Gly | Arg | Thr | Gly |
| | | | 195 | | | | 200 | | | | 205 | | | | |
| Asp | Arg | Pro | Arg | Thr | Phe | Val | Gly | Val | His | Val | Arg | Arg | Gly | Asp | Tyr |
| | | 210 | | | | 215 | | | | | 220 | | | | |
| Leu | Gln | Val | Met | Pro | Gln | Arg | Trp | Lys | Gly | Val | Val | Gly | Asp | Ser | Ala |
| 225 | | | | 230 | | | | 235 | | | | | | 240 | |
| Tyr | Leu | Arg | Gln | Ala | Met | Asp | Trp | Phe | Arg | Ala | Arg | His | Glu | Ala | Pro |
| | | | 245 | | | | 250 | | | | | 255 | | | |
| Val | Phe | Val | Val | Thr | Ser | Asn | Gly | Met | Glu | Trp | Cys | Lys | Glu | Asn | Ile |
| | | | 260 | | | | 265 | | | | | 270 | | | |
| Asp | Thr | Ser | Gln | Gly | Asp | Val | Thr | Phe | Ala | Gly | Asp | Gly | Gln | Glu | Ala |
| | | 275 | | | | | 280 | | | | | 285 | | | |
| Thr | Pro | Trp | Lys | Asp | Phe | Ala | Leu | Leu | Thr | Gln | Cys | Asn | His | Thr | Ile |
| | 290 | | | | | 295 | | | | | 300 | | | | |
| Met | Thr | Ile | Gly | Thr | Phe | Gly | Phe | Trp | Ala | Ala | Tyr | Leu | Ala | Gly | Gly |
| 305 | | | | | 310 | | | | 315 | | | | | 320 | |
| Asp | Thr | Val | Tyr | Leu | Ala | Asn | Phe | Thr | Leu | Pro | Asp | Ser | Glu | Phe | Leu |
| | | | | 325 | | | | 330 | | | | | 335 | | |
| Lys | Ile | Phe | Lys | Pro | Glu | Ala | Ala | Phe | Leu | Pro | Glu | Trp | Val | Gly | Ile |
| | | | 340 | | | | 345 | | | | | 350 | | | |
| Asn | Ala | Asp | Leu | Ser | Pro | Leu | Trp | Thr | Leu | Ala | Lys | Pro | | | |
| | | 355 | | | | | 360 | | | | | 365 | | | |

(2) INFORMATION FOR SEQ ID NO:7:

(i) SEQUENCE CHARACTERISTICS:
        (A) LENGTH: 2115 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 64..1092

(xi) SEQUENCE DESCRIPTION: SEQ ID NO:7:

```
TTCACCAGCG CCCCGGGCCT CCATCTCCCA GCTAACGTGT CCCGTTTTCC TCCCCTGACA             60

GCC ATG CTG GTC GTT CAG ATG CCT TTC TCC TTT CCC ATG GCC CAC TTC             108
    Met Leu Val Val Gln Met Pro Phe Ser Phe Pro Met Ala His Phe
                        370             375                     380

ATC CTC TTT GTC TTT ACG GTT TCC ACT ATA TTT CAC GTT CAG CAG CGG             156
Ile Leu Phe Val Phe Thr Val Ser Thr Ile Phe His Val Gln Gln Arg
                385                 390                 395

CTA GCG AAG ATT CAA GCC ATG TGG GAG TTA CCG GTG CAG ATA CCA GTG             204
Leu Ala Lys Ile Gln Ala Met Trp Glu Leu Pro Val Gln Ile Pro Val
                400                 405                 410

CTA GCC TCA ACA TCA AAG GCA CTG GGA CCC AGC CAG CTC AGG GGG ATG             252
Leu Ala Ser Thr Ser Lys Ala Leu Gly Pro Ser Gln Leu Arg Gly Met
                415                 420                 425

TGG ACG ATC AAT GCA ATA GGC CGC CTG GGG AAC CAG ATG GGC GAG TAC             300
Trp Thr Ile Asn Ala Ile Gly Arg Leu Gly Asn Gln Met Gly Glu Tyr
        430                 435                 440

GCC ACA CTG TAC GCC CTG GCC AAG ATG AAC GGG CGG CCC GCC TTC ATC             348
Ala Thr Leu Tyr Ala Leu Ala Lys Met Asn Gly Arg Pro Ala Phe Ile
445                 450                 455                 460
```

| | | | | | | | | | | | | | | | | |
|---|---|---|---|---|---|---|---|---|---|---|---|---|---|---|---|---|
| CCG | GCC | CAG | ATG | CAC | AGC | ACC | CTG | GCC | CCC | ATC | TTC | AGA | ATC | ACC | CTG | 396 |
| Pro | Ala | Gln | Met | His | Ser | Thr | Leu | Ala | Pro | Ile | Phe | Arg | Ile | Thr | Leu | |
| | | | | 465 | | | | | 470 | | | | | 475 | | |
| CCG | GTG | CTG | CAC | AGC | GCC | ACG | GCC | AGC | AGG | ATC | CCC | TGG | CAG | AAC | TAC | 444 |
| Pro | Val | Leu | His | Ser | Ala | Thr | Ala | Ser | Arg | Ile | Pro | Trp | Gln | Asn | Tyr | |
| | | | 480 | | | | | 485 | | | | | 490 | | | |
| CAC | CTG | AAC | GAC | TGG | ATG | GAG | GAG | GAA | TAC | CGC | CAC | ATC | CCG | GGG | GAG | 492 |
| His | Leu | Asn | Asp | Trp | Met | Glu | Glu | Glu | Tyr | Arg | His | Ile | Pro | Gly | Glu | |
| | | 495 | | | | | 500 | | | | | 505 | | | | |
| TAC | GTC | CGC | TTC | ACC | GGC | TAC | CCC | TGC | TCC | TGG | ACC | TTC | TAC | CAC | CAC | 540 |
| Tyr | Val | Arg | Phe | Thr | Gly | Tyr | Pro | Cys | Ser | Trp | Thr | Phe | Tyr | His | His | |
| | 510 | | | | | 515 | | | | | 520 | | | | | |
| CTC | CGC | CAG | GAG | ATC | CTC | CAG | GAG | TTC | ACC | CTG | CAC | GAC | CAC | GTG | CGG | 588 |
| Leu | Arg | Gln | Glu | Ile | Leu | Gln | Glu | Phe | Thr | Leu | His | Asp | His | Val | Arg | |
| 525 | | | | | 530 | | | | | 535 | | | | | 540 | |
| GAG | GAG | GCC | CAG | AAG | TTC | CTG | CGG | GGC | CTG | CAG | GTG | AAC | GGG | AGC | CGG | 636 |
| Glu | Glu | Ala | Gln | Lys | Phe | Leu | Arg | Gly | Leu | Gln | Val | Asn | Gly | Ser | Arg | |
| | | | | 545 | | | | | 550 | | | | | 555 | | |
| CCG | GGC | ACC | TTT | GTA | GGG | GTC | CAT | GTT | CGC | CGA | GGG | GAT | TAT | GTC | CAT | 684 |
| Pro | Gly | Thr | Phe | Val | Gly | Val | His | Val | Arg | Arg | Gly | Asp | Tyr | Val | His | |
| | | | 560 | | | | | 565 | | | | | 570 | | | |
| GTC | ATG | CCA | AAA | GTG | TGG | AAG | GGG | GTG | GTG | GCC | GAC | CGG | CGA | TAC | CTA | 732 |
| Val | Met | Pro | Lys | Val | Trp | Lys | Gly | Val | Val | Ala | Asp | Arg | Arg | Tyr | Leu | |
| | | 575 | | | | | 580 | | | | | 585 | | | | |
| CAG | CAG | GCC | CTG | GAC | TGG | TTC | CGA | GCT | CGC | TAC | AGC | TCC | CTC | ATC | TTC | 780 |
| Gln | Gln | Ala | Leu | Asp | Trp | Phe | Arg | Ala | Arg | Tyr | Ser | Ser | Leu | Ile | Phe | |
| | 590 | | | | | 595 | | | | | 600 | | | | | |
| GTG | GTC | ACC | AGT | AAT | GGC | ATG | GCC | TGG | TGT | CGG | GAG | AAC | ATT | GAC | ACC | 828 |
| Val | Val | Thr | Ser | Asn | Gly | Met | Ala | Trp | Cys | Arg | Glu | Asn | Ile | Asp | Thr | |
| 605 | | | | | 610 | | | | | 615 | | | | | 620 | |
| TCC | CAC | GGT | GAT | GTG | GTG | TTT | GCT | GGC | GAT | GGC | ATT | GAG | GGC | TCA | CCT | 876 |
| Ser | His | Gly | Asp | Val | Val | Phe | Ala | Gly | Asp | Gly | Ile | Glu | Gly | Ser | Pro | |
| | | | | 625 | | | | | 630 | | | | | 635 | | |
| GCC | AAA | GAT | TTT | GCT | CTA | CTC | ACA | CAG | TGT | AAC | CAC | ACC | ATC | ATG | ACC | 924 |
| Ala | Lys | Asp | Phe | Ala | Leu | Leu | Thr | Gln | Cys | Asn | His | Thr | Ile | Met | Thr | |
| | | | 640 | | | | | 645 | | | | | 650 | | | |
| ATT | GGG | ACG | TTC | GGG | ATC | TGG | GCC | GCA | TAC | CTC | ACG | GGC | GGA | GAC | ACC | 972 |
| Ile | Gly | Thr | Phe | Gly | Ile | Trp | Ala | Ala | Tyr | Leu | Thr | Gly | Gly | Asp | Thr | |
| | | 655 | | | | | 660 | | | | | 665 | | | | |
| ATC | TAC | CTG | GCC | AAT | TAC | ACC | CTC | CCC | GAC | TCC | CCT | TTC | CTC | AAA | ATC | 1020 |
| Ile | Tyr | Leu | Ala | Asn | Tyr | Thr | Leu | Pro | Asp | Ser | Pro | Phe | Leu | Lys | Ile | |
| | 670 | | | | | 675 | | | | | 680 | | | | | |
| TTT | AAG | CCA | GAG | GCA | GCC | TTC | CTG | CCG | GAG | TGG | ACA | GGG | ATT | GCC | GCA | 1068 |
| Phe | Lys | Pro | Glu | Ala | Ala | Phe | Leu | Pro | Glu | Trp | Thr | Gly | Ile | Ala | Ala | |
| 685 | | | | 690 | | | | | 695 | | | | | 700 | | |
| GAC | CTG | TCC | CCC | TTA | CTC | AAG | CAC | TAATGCTGGC | CCGTCCTTTG | AGACCTTTTC | | | | | | 1122 |
| Asp | Leu | Ser | Pro | Leu | Leu | Lys | His | | | | | | | | | |
| | | | | 705 | | | | | | | | | | | | |

| | | | | |
|---|---|---|---|---|
| TCCTTCTCTG | CCTCCCTCAA | GATGAGTGCC | CGGGCATGAG | AAGCACATGG | TTCCATGAGC | 1182 |
| AGGACCCATC | TCTCTTCTGT | GAAGATGCGT | TGGGCTGCAA | GTAACAGAAA | TCTCAGTGAA | 1242 |
| CAGTGGCCTG | GCGTGGTGGC | TCATGCCTGT | AATGCTCGCA | CTTTGGGAGG | CCAGGGTGGG | 1302 |
| TGGATCACTT | GAGGTCAGGA | GTTCAAGACT | AGCCTGGCCA | ACATGGTGAA | ACCCCATCTC | 1362 |
| GACTAAAAAT | ACAAAAATTA | GCCAGGCGTG | GTGGTGCACA | CTTGTAATCC | CAGCTACTCG | 1422 |
| GGAGGCTGAG | GCAAGAGAAT | CACTTGAACC | CAGGAGGCGG | AGGTTGCAGT | GAGCCAAGAT | 1482 |
| GGTGCCGCTG | CACTCCAGCC | TGGGTGACAC | AGCAAGACTC | CATCTCAAAA | AAAAAAAAAG | 1542 |
| AAAAAGAAAT | GAACGGGTTC | AAAGACCATA | ATCATGCATA | TCACATAAGA | CCAGAAGTGG | 1602 |

-continued

| | | | | | |
|---|---|---|---|---|---|
| CCCAGGTCCA | GGGTCAGTTA | ATTTAGCAGC | TCCACAAAGT | CATCAGTCAC | CTGAGCTCCA | 1662 |
| TCCATCTTCA | CATGCTGTGC | TACCATTTCT | TAGCTGTATC | ATCCATGGT | CCCAAAAGGG | 1722 |
| CTGCTACACA | TCCAGCCATC | ACATGCAGAT | AATTCCTTTC | AAAAACAGCA | GAAAGAGGCT | 1782 |
| CGTTCTTGTC | TTGGTCCCTT | TTGAAGAATG | AATGAAACCT | TCCTAAGCCT | TCCAGCAATT | 1842 |
| TCCCCCCAAC | TCCGATGGGT | AGGAATTGTC | ACATACCCAT | GTGACCCGAT | AGGAGGCAAA | 1902 |
| AGAAATGAGA | CTTCTGGGAT | TAGTTTAGCC | TCAGATTCTG | CAGCTGAGAA | GTTGATCAGC | 1962 |
| CACCTCTGAA | GGACATGCAG | CTTGCAGAAA | ATTAGGGTGG | TGTTACCAAG | GTGAAAAGGG | 2022 |
| GAAATGGCTT | TAGAGTAGAC | AACAGAGATG | CCCTGAGGGG | TTGTGTAGGT | TGTTCACTGC | 2082 |
| AGGAAGTCCC | CTGGTTAAGA | AGGCAAGTGG | GGT | | | 2115 |

( 2 ) INFORMATION FOR SEQ ID NO:8:

( i ) SEQUENCE CHARACTERISTICS:
        ( A ) LENGTH: 343 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Met Leu Val Val Gln Met Pro Phe Ser Phe Pro Met Ala His Phe Ile
  1               5                  10                  15

Leu Phe Val Phe Thr Val Ser Thr Ile Phe His Val Gln Gln Arg Leu
                 20                  25                  30

Ala Lys Ile Gln Ala Met Trp Glu Leu Pro Val Gln Ile Pro Val Leu
             35                  40                  45

Ala Ser Thr Ser Lys Ala Leu Gly Pro Ser Gln Leu Arg Gly Met Trp
         50                  55                  60

Thr Ile Asn Ala Ile Gly Arg Leu Gly Asn Gln Met Gly Glu Tyr Ala
 65                  70                  75                  80

Thr Leu Tyr Ala Leu Ala Lys Met Asn Gly Arg Pro Ala Phe Ile Pro
                 85                  90                  95

Ala Gln Met His Ser Thr Leu Ala Pro Ile Phe Arg Ile Thr Leu Pro
            100                 105                 110

Val Leu His Ser Ala Thr Ala Ser Arg Ile Pro Trp Gln Asn Tyr His
        115                 120                 125

Leu Asn Asp Trp Met Glu Glu Glu Tyr Arg His Ile Pro Gly Glu Tyr
130                 135                 140

Val Arg Phe Thr Gly Tyr Pro Cys Ser Trp Thr Phe Tyr His His Leu
145                 150                 155                 160

Arg Gln Glu Ile Leu Gln Glu Phe Thr Leu His Asp His Val Arg Glu
                165                 170                 175

Glu Ala Gln Lys Phe Leu Arg Gly Leu Gln Val Asn Gly Ser Arg Pro
            180                 185                 190

Gly Thr Phe Val Gly Val His Val Arg Arg Gly Asp Tyr Val His Val
        195                 200                 205

Met Pro Lys Val Trp Lys Gly Val Val Ala Asp Arg Arg Tyr Leu Gln
        210                 215                 220

Gln Ala Leu Asp Trp Phe Arg Ala Arg Tyr Ser Ser Leu Ile Phe Val
225                 230                 235                 240

Val Thr Ser Asn Gly Met Ala Trp Cys Arg Glu Asn Ile Asp Thr Ser
                245                 250                 255

His Gly Asp Val Val Phe Ala Gly Asp Gly Ile Glu Gly Ser Pro Ala
            260                 265                 270
```

| | | | | | | | | | | | | | | |
|---|---|---|---|---|---|---|---|---|---|---|---|---|---|---|
|Lys|Asp|Phe|Ala|Leu|Leu|Thr|Gln|Cys|Asn|His|Thr|Ile|Met|Thr|Ile|
| |275| | | | |280| | | |285| | | | |
|Gly|Thr|Phe|Gly|Ile|Trp|Ala|Ala|Tyr|Leu|Thr|Gly|Gly|Asp|Thr|Ile|
| |290| | | |295| | | |300| | | | | |
|Tyr|Leu|Ala|Asn|Tyr|Thr|Leu|Pro|Asp|Ser|Pro|Phe|Leu|Lys|Ile|Phe|
|305| | | |310| | | |315| | | | |320| |
|Lys|Pro|Glu|Ala|Ala|Phe|Leu|Pro|Glu|Trp|Thr|Gly|Ile|Ala|Ala|Asp|
| | | |325| | | |330| | | | |335| | |
|Leu|Ser|Pro|Leu|Leu|Lys|His| | | | | | | | | |
| | | |340| | | | | | | | | | | | |

(2) INFORMATION FOR SEQ ID NO:9:

(i) SEQUENCE CHARACTERISTICS:
(A) LENGTH: 1136 base pairs
(B) TYPE: nucleic acid
(C) STRANDEDNESS: double
(D) TOPOLOGY: linear (ix) FEATURE:
(A) NAME/KEY: CDS
(B) LOCATION: 39..1133

(xi) SEQUENCE DESCRIPTION: SEQ ID NO:9:

```
CAGTGCATTT GCTAATTCGC CTTTCCTCCC CTGCAGCC ATG TGG CTC CGG AGC        53
                                          Met Trp Leu Arg Ser
                                              345

CAT CGT CAG CTC TGC CTG GCC TTC CTG CTA GTC TGT GTC CTC TCT GTA     101
His Arg Gln Leu Cys Leu Ala Phe Leu Leu Val Cys Val Leu Ser Val
    350             355                 360

ATC TTC TTC CTC CAT ATC CAT CAA GAC AGC TTT CCA CAT GGC CTA GGC     149
Ile Phe Phe Leu His Ile His Gln Asp Ser Phe Pro His Gly Leu Gly
365             370                 375                 380

CTG TCG ATC CTG TGT CCA GAC CGC CGC CTG GTG ACA CCC CCA GTG GCC     197
Leu Ser Ile Leu Cys Pro Asp Arg Arg Leu Val Thr Pro Pro Val Ala
                385                 390                 395

ATC TTC TGC CTG CCG GGT ACT GCG ATG GGC CCC AAC GCC TCC TCT TCC     245
Ile Phe Cys Leu Pro Gly Thr Ala Met Gly Pro Asn Ala Ser Ser Ser
            400                 405                 410

TGT CCC CAG CAC CCT GCT TCC CTC TCC GGC ACC TGG ACT GTC TAC CCC     293
Cys Pro Gln His Pro Ala Ser Leu Ser Gly Thr Trp Thr Val Tyr Pro
        415                 420                 425

AAT GGC CGG TTT GGT AAT CAG ATG GGA CAG TAT GCC ACG CTG CTG GCT     341
Asn Gly Arg Phe Gly Asn Gln Met Gly Gln Tyr Ala Thr Leu Leu Ala
    430                 435                 440

CTG GCC CAG CTC AAC GGC CGC CGG GCC TTT ATC CTG CCT GCC ATG CAT     389
Leu Ala Gln Leu Asn Gly Arg Arg Ala Phe Ile Leu Pro Ala Met His
445                 450                 455                 460

GCC GCC CTG GCC CCG GTA TTC CGC ATC ACC CTG CCC GTG CTG GCC CCA     437
Ala Ala Leu Ala Pro Val Phe Arg Ile Thr Leu Pro Val Leu Ala Pro
                465                 470                 475

GAA GTG GAC AGC CGC ACG CCG TGG CGG GAG CTG CAG CTT CAC GAC TGG     485
Glu Val Asp Ser Arg Thr Pro Trp Arg Glu Leu Gln Leu His Asp Trp
            480                 485                 490

ATG TCG GAG GAG TAC GCG GAC TTG AGA GAT CCT TTC CTG AAG CTC TCT     533
Met Ser Glu Glu Tyr Ala Asp Leu Arg Asp Pro Phe Leu Lys Leu Ser
        495                 500                 505

GGC TTC CCC TGC TCT TGG ACT TTC TTC CAC CAT CTC CGG GAA CAG ATC     581
Gly Phe Pro Cys Ser Trp Thr Phe Phe His His Leu Arg Glu Gln Ile
    510                 515                 520
```

| | | | | | | | | | | | | | | | | |
|---|---|---|---|---|---|---|---|---|---|---|---|---|---|---|---|---|
| CGC | AGA | GAG | TTC | ACC | CTG | CAC | GAC | CAC | CTT | CGG | GAA | GAG | GCG | CAG | AGT | 629 |
| Arg | Arg | Glu | Phe | Thr | Leu | His | Asp | His | Leu | Arg | Glu | Glu | Ala | Gln | Ser | |
| 525 | | | | | 530 | | | | | 535 | | | | | 540 | |
| GTG | CTG | GGT | CAG | CTC | CGC | CTG | GGC | CGC | ACA | GGG | GAC | CGC | CCG | CGC | ACC | 677 |
| Val | Leu | Gly | Gln | Leu | Arg | Leu | Gly | Arg | Thr | Gly | Asp | Arg | Pro | Arg | Thr | |
| | | | | 545 | | | | | 550 | | | | | 555 | | |
| TTT | GTC | GGC | GTC | CAC | GTG | CGC | CGT | GGG | GAC | TAT | CTG | CAG | GTT | ATG | CCT | 725 |
| Phe | Val | Gly | Val | His | Val | Arg | Arg | Gly | Asp | Tyr | Leu | Gln | Val | Met | Pro | |
| | | | 560 | | | | | 565 | | | | | 570 | | | |
| CAG | CGC | TGG | AAG | GGT | GTG | GTG | GGC | GAC | AGC | GCC | TAC | CTC | CGG | CAG | GCC | 773 |
| Gln | Arg | Trp | Lys | Gly | Val | Val | Gly | Asp | Ser | Ala | Tyr | Leu | Arg | Gln | Ala | |
| | | 575 | | | | | 580 | | | | | 585 | | | | |
| ATG | GAC | TGG | TTC | CGG | GCA | CGG | CAC | GAA | GCC | CCC | GTT | TTC | GTG | GTC | ACC | 821 |
| Met | Asp | Trp | Phe | Arg | Ala | Arg | His | Glu | Ala | Pro | Val | Phe | Val | Val | Thr | |
| | 590 | | | | | 595 | | | | | 600 | | | | | |
| AGC | AAC | GGC | ATG | GAG | TGG | TGT | AAA | GAA | AAC | ATC | GAC | ACC | TCC | CAG | GGC | 869 |
| Ser | Asn | Gly | Met | Glu | Trp | Cys | Lys | Glu | Asn | Ile | Asp | Thr | Ser | Gln | Gly | |
| 605 | | | | | 610 | | | | | 615 | | | | | 620 | |
| GAT | GTG | ACG | TTT | GCT | GGC | GAT | GGA | CAG | GAG | GCT | ACA | CCG | TGG | AAA | GAC | 917 |
| Asp | Val | Thr | Phe | Ala | Gly | Asp | Gly | Gln | Glu | Ala | Thr | Pro | Trp | Lys | Asp | |
| | | | | 625 | | | | | 630 | | | | | 635 | | |
| TTT | GCC | CTG | CTC | ACA | CAG | TGC | AAC | CAC | ACC | ATT | ATG | ACC | ATT | GGC | ACC | 965 |
| Phe | Ala | Leu | Leu | Thr | Gln | Cys | Asn | His | Thr | Ile | Met | Thr | Ile | Gly | Thr | |
| | | | 640 | | | | | 645 | | | | | 650 | | | |
| TTC | GGC | TTC | TGG | GCT | GCC | TAC | CTG | GCT | GGC | GGA | GAC | ACT | GTC | TAC | CTG | 1013 |
| Phe | Gly | Phe | Trp | Ala | Ala | Tyr | Leu | Ala | Gly | Gly | Asp | Thr | Val | Tyr | Leu | |
| | | 655 | | | | | 660 | | | | | 665 | | | | |
| GCC | AAC | TTC | ACC | CTG | CCA | GAC | TCT | GAG | TTC | CTG | AAG | ATC | TTT | AAG | CCG | 1061 |
| Ala | Asn | Phe | Thr | Leu | Pro | Asp | Ser | Glu | Phe | Leu | Lys | Ile | Phe | Lys | Pro | |
| | | 670 | | | | 675 | | | | | 680 | | | | | |
| GAG | GCG | GCC | TTC | CTG | CCC | GAG | TGG | GTG | GGC | ATT | AAT | GCA | GAC | TTG | TCT | 1109 |
| Glu | Ala | Ala | Phe | Leu | Pro | Glu | Trp | Val | Gly | Ile | Asn | Ala | Asp | Leu | Ser | |
| 685 | | | | | 690 | | | | | 695 | | | | | 700 | |
| CCA | CTC | TGG | ACA | TTG | GCT | AAG | CCT | TGA | | | | | | | | 1136 |
| Pro | Leu | Trp | Thr | Leu | Ala | Lys | Pro | | | | | | | | | |
| | | | | 705 | | | | | | | | | | | | |

( 2 ) INFORMATION FOR SEQ ID NO:10:

( i ) SEQUENCE CHARACTERISTICS:
        ( A ) LENGTH: 365 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

| | | | | | | | | | | | | | | |
|---|---|---|---|---|---|---|---|---|---|---|---|---|---|---|
| Met | Trp | Leu | Arg | Ser | His | Arg | Gln | Leu | Cys | Leu | Ala | Phe | Leu | Leu | Val |
| 1 | | | | 5 | | | | | 10 | | | | | 15 | |
| Cys | Val | Leu | Ser | Val | Ile | Phe | Phe | Leu | His | Ile | His | Gln | Asp | Ser | Phe |
| | | | 20 | | | | | 25 | | | | | 30 | | |
| Pro | His | Gly | Leu | Gly | Leu | Ser | Ile | Leu | Cys | Pro | Asp | Arg | Arg | Leu | Val |
| | | | 35 | | | | | 40 | | | | | 45 | | |
| Thr | Pro | Pro | Val | Ala | Ile | Phe | Cys | Leu | Pro | Gly | Thr | Ala | Met | Gly | Pro |
| | | 50 | | | | | 55 | | | | | 60 | | | |
| Asn | Ala | Ser | Ser | Ser | Cys | Pro | Gln | His | Pro | Ala | Ser | Leu | Ser | Gly | Thr |
| 65 | | | | | 70 | | | | | 75 | | | | | 80 |
| Trp | Thr | Val | Tyr | Pro | Asn | Gly | Arg | Phe | Gly | Asn | Gln | Met | Gly | Gln | Tyr |
| | | | | 85 | | | | | 90 | | | | | 95 | |
| Ala | Thr | Leu | Leu | Ala | Leu | Ala | Gln | Leu | Asn | Gly | Arg | Arg | Ala | Phe | Ile |
| | | | 100 | | | | | 105 | | | | | 110 | | |

```
Leu  Pro  Ala  Met  His  Ala  Ala  Leu  Ala  Pro  Val  Phe  Arg  Ile  Thr  Leu
          115                120                135            125

Pro  Val  Leu  Ala  Pro  Glu  Val  Asp  Ser  Arg  Thr  Pro  Trp  Arg  Glu  Leu
     130                135                     140

Gln  Leu  His  Asp  Trp  Met  Ser  Glu  Glu  Tyr  Ala  Asp  Leu  Arg  Asp  Pro
145                 150                     155                          160

Phe  Leu  Lys  Leu  Ser  Gly  Phe  Pro  Cys  Ser  Trp  Thr  Phe  Phe  His  His
                    165                170                               175

Leu  Arg  Glu  Gln  Ile  Arg  Arg  Glu  Phe  Thr  Leu  His  Asp  His  Leu  Arg
               180                185                          190

Glu  Glu  Ala  Gln  Ser  Val  Leu  Gly  Gln  Leu  Arg  Leu  Gly  Arg  Thr  Gly
          195                     200                     205

Asp  Arg  Pro  Arg  Thr  Phe  Val  Gly  Val  His  Val  Arg  Arg  Gly  Asp  Tyr
     210                     215                     220

Leu  Gln  Val  Met  Pro  Gln  Arg  Trp  Lys  Gly  Val  Val  Gly  Asp  Ser  Ala
225                      230                235                          240

Tyr  Leu  Arg  Gln  Ala  Met  Asp  Trp  Phe  Arg  Ala  Arg  His  Glu  Ala  Pro
                    245                     250                     255

Val  Phe  Val  Val  Thr  Ser  Asn  Gly  Met  Glu  Trp  Cys  Lys  Glu  Asn  Ile
               260                     265                     270

Asp  Thr  Ser  Gln  Gly  Asp  Val  Thr  Phe  Ala  Gly  Asp  Gly  Gln  Glu  Ala
          275                     280                     285

Thr  Pro  Trp  Lys  Asp  Phe  Ala  Leu  Leu  Thr  Gln  Cys  Asn  His  Thr  Ile
     290                          295                     300

Met  Thr  Ile  Gly  Thr  Phe  Gly  Phe  Trp  Ala  Ala  Tyr  Leu  Ala  Gly  Gly
305                           310                315                          320

Asp  Thr  Val  Tyr  Leu  Ala  Asn  Phe  Thr  Leu  Pro  Asp  Ser  Glu  Phe  Leu
                    325                     330                          335

Lys  Ile  Phe  Lys  Pro  Glu  Ala  Ala  Phe  Leu  Pro  Glu  Trp  Val  Gly  Ile
               340                     345                     350

Asn  Ala  Asp  Leu  Ser  Pro  Leu  Trp  Thr  Leu  Ala  Lys  Pro
          355                     360                     365
```

( 2 ) INFORMATION FOR SEQ ID NO:11:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:11:

GCGCGAATTC TATAAACACA CTTGAGATAC ATGCCTGTGC      40

( 2 ) INFORMATION FOR SEQ ID NO:12:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:12:

GCGCTCTAGA ATGGACCCCT ACAAAGGTGC CCGGCCGGCT      40

( 2 ) INFORMATION FOR SEQ ID NO:13:

( i ) SEQUENCE CHARACTERISTICS:
    ( A ) LENGTH: 40 base pairs (B) TYPE: nucleic acid
(C) STRANDEDNESS: single
(D) TOPOLOGY: linear (xi) SEQUENCE DESCRIPTION: SEQ ID NO:13:

GCGCGAATTC GAGGAATACC GCCACATCCC GGGGGAGTAC         40

(2) INFORMATION FOR SEQ ID NO:14:

(i) SEQUENCE CHARACTERISTICS:
(A) LENGTH: 40 base pairs
(B) TYPE: nucleic acid
(C) STRANDEDNESS: single
(D) TOPOLOGY: linear (xi) SEQUENCE DESCRIPTION: SEQ ID NO:14:

GCGCTCTAGA GAACCATGTG CTTCTCATGC CCGGGCACTC         40

(2) INFORMATION FOR SEQ ID NO:15:

(i) SEQUENCE CHARACTERISTICS:
(A) LENGTH: 40 base pairs
(B) TYPE: nucleic acid
(C) STRANDEDNESS: single
(D) TOPOLOGY: linear (xi) SEQUENCE DESCRIPTION: SEQ ID NO:15:

GCGCGAATTC CCTTTCTCCT TTCCCATGGC CCACTTCATC         40

(2) INFORMATION FOR SEQ ID NO:16:

(i) SEQUENCE CHARACTERISTICS:
(A) LENGTH: 40 base pairs
(B) TYPE: nucleic acid
(C) STRANDEDNESS: single
(D) TOPOLOGY: linear (xi) SEQUENCE DESCRIPTION: SEQ ID NO:16:

GCGCTCTAGA GGAGAAAAGG TCTCAAAGGA CGGGCCAGCA         40

(2) INFORMATION FOR SEQ ID NO:17:

(i) SEQUENCE CHARACTERISTICS:
(A) LENGTH: 40 base pairs
(B) TYPE: nucleic acid
(C) STRANDEDNESS: single
(D) TOPOLOGY: linear (xi) SEQUENCE DESCRIPTION: SEQ ID NO:17:

GCGCGAATTC ATGGACCCCT ACAAAGGTGC CCGGCCGGCT         40

(2) INFORMATION FOR SEQ ID NO:18:

(i) SEQUENCE CHARACTERISTICS:
(A) LENGTH: 40 base pairs
(B) TYPE: nucleic acid
(C) STRANDEDNESS: single
(D) TOPOLOGY: linear (xi) SEQUENCE DESCRIPTION: SEQ ID NO:18:

GCGCGAATTC CCATGCTGGT CGTTCAGATG CCTTTCTCCT         40

(2) INFORMATION FOR SEQ ID NO:19:

(i) SEQUENCE CHARACTERISTICS:
(A) LENGTH: 30 base pairs
(B) TYPE: nucleic acid
(C) STRANDEDNESS: single (D) TOPOLOGY: linear (xi) SEQUENCE DESCRIPTION: SEQ ID NO:19:

GAGGAATACC GCCACATCCC GGGGGAGTAC 30

(2) INFORMATION FOR SEQ ID NO:20:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (xi) SEQUENCE DESCRIPTION: SEQ ID NO:20:

ATGGACCCCT ACAAAGGTGC CCGGCCGGCT 30

(2) INFORMATION FOR SEQ ID NO:21:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (xi) SEQUENCE DESCRIPTION: SEQ ID NO:21:

TGCTCCTGGA CCTTC 15

(2) INFORMATION FOR SEQ ID NO:22:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (xi) SEQUENCE DESCRIPTION: SEQ ID NO:22:

TGCTCCTAGA CCTTC 15

What is claimed as new and is desired to be secured by Letters Patent of the Unites States is:

1. An isolated sequence of DNA, which comprises a sequence of DNA selected from the group consisting of:
   (a) a DNA sequence corresponding to from position 1 to position 2115 of SEQ ID NO: 7;
   (b) a DNA sequence corresponding to from position 148 to position 1092 of SEQ ID NO: 7; and
   (c) a DNA sequence corresponding to from position 120 to position 1092 of SEQ ID NO: 7.

2. The isolated sequence of DNA of claim 1, which comprises said sequence of DNA corresponding to from position 1 to position 2115 of SEQ ID NO: 7.

3. The isolated sequence of DNA of claim 1, which comprises said sequence of DNA corresponding to from position 148 to position 1092 of SEQ ID NO: 7.

4. The isolated sequence of DNA of claim 1, which comprises said sequence of DNA corresponding to from position 120 to position 1092 of SEQ ID NO: 7.

5. A plasmid, comprising a sequence of DNA, wherein said sequence of DNA comprises a sequence of DNA selected from the group consisting of:
   (a) a DNA sequence corresponding to from position 1 to position 2115 of SEQ ID NO: 7;
   (b) a DNA sequence corresponding to from position 148 to position 1092 of SEQ ID NO: 7; and
   (c) a DNA sequence corresponding to from position 120 to position 1092 of SEQ ID NO: 7.

6. The plasmid of claim 5, wherein said sequence of DNA comprises said sequence of DNA corresponding to from position 1 to position 2115 of SEQ ID NO: 7.

7. The plasmid of claim 5, wherein said sequence of DNA comprises said sequence of DNA corresponding to from position 148 to position 1092 of SEQ ID NO: 7.

8. The plasmid of claim 5, wherein said sequence of DNA comprises said sequence of DNA corresponding to from position 120 to position 1092 of SEQ ID NO: 7.

9. A transformed cell, comprising a plasmid, wherein said plasmid comprises a sequence of DNA, wherein said sequence of DNA comprises a sequence of DNA selected from the group consisting of:
   (a) a DNA sequence corresponding to from position 1 to position 2115 of SEQ ID NO: 7;
   (b) a DNA sequence corresponding to from position 148 to position 1092 of SEQ ID NO: 7; and
   (c) a DNA sequence corresponding to from position 120 to position 1092 of SEQ ID NO: 7.

10. The transformed cell of claim 9, wherein said sequence of DNA comprises said sequence of DNA corresponding to from position 1 to position 2115 of SEQ ID NO: 7.

11. The transformed cell of claim 9, wherein said sequence of DNA comprises said sequence of DNA corresponding to from position 148 to position 1092 of SEQ ID NO: 7.

12. The transformed cell of claim 9, wherein said sequence of DNA comprises said sequence of DNA corresponding to from position 120 to position 1092 of SEQ ID NO: 7.

* * * * *

UNITED STATES PATENT AND TRADEMARK OFFICE
CERTIFICATE OF CORRECTION

PATENT NO. : 5,807,732
DATED : September 15, 1998
INVENTOR(S) : John B. Lowe et al.

It is certified that error appears in the above-identified patent and that said Letters Patent is hereby corrected as shown below:

Column 2,
Line 23, "Cytogenet," should read -- *Cytogenet.* --; and
Line 58, "Kop èc" should read -- Kopèc --

Column 3,
Line 7, "In:" should read -- *In:* --.

Column 6,
Line 9, "FIGS. 8*a* and *b*" should read -- FIGS. 8*a-d* -- ;
Line 11, "sequence." should read -- sequence (SEQ ID NOS: 1-6). --;
Line 24, "sequence identity" should read -- sequence (SEQ ID NOS: 5-10) identity --;
Line 47, "FIGS. 9*a, b* and *c*" should read -- FIGS. 9*a-e* --.

Column 7,
Line 57, "FIGS. 10*a-e*" should read -- FIGS. 10*a-i* --.

Column 8,
Line 13, "β(1,2)" should read -- α(1,2) --.

Column 17,
Line 5, "at 50° C.). should read -- at 50° C). --.

Column 19,
Line 24, "Alto, Calif.)," should read -- Alto, CA), --.

Column 22,
Line 4, "CATGCCTGTGC; should read -- CATGCCTGTGC (SEQ ID NO: 11); --;
Line 7, "CCGGCT;" should read -- CCGGCT (SEQ ID NO: 12);--;
Line 12 "CGGGGGAGTAC;" should read -- CGGGGGAGTAC (SEQ ID NO:13); --;
Line 16, "CACTC;" should read -- CACTC (SEQ ID NO: 14);--:
Line 49, "GCCCACTTCATC;" shoud read -- GCCCACTTCATC (SEQ ID NO: 15); --;
Line 53, "GCCAGCA;" should read -- GCCAGCA (SEQ ID NO: 16); --.

Column 23,
Line 15, "ACACTTGAGATACATGCCTGTGC;" should read
-- ACACTTGAGATACATGCCTGTGC (SEQ ID NO: 11); --;
Line 20, "CCGGCCGGCT; should read -- CCGGCCGGCT (SEQ ID NO: 17); --

UNITED STATES PATENT AND TRADEMARK OFFICE
CERTIFICATE OF CORRECTION

PATENT NO. : 5,807,732
DATED : September 15, 1998
INVENTOR(S) : John B. Lowe et al.

It is certified that error appears in the above-identified patent and that said Letters Patent is hereby corrected as shown below:

Column 23,
Line 40, "CT<u>C</u>CT;" should read -- CTCCT (SEQ ID NO: 18); --;
Line 44, "<u>GTGCCCGGCCGGCT</u>;" should read -- <u>GTGCCCGGCCGGCT</u> (SEQ ID NO: 17); --.

Column 25,
Line 31, "(GAGGAATACCGCCACATCCCGGGGGAGTAC and" should read --(GAGGAATACCGCCACATCCCGGGGGAGTAC (SEQ ID NO: 19) and --; and
Line 32, "ATGGACCCCTACAAAGGTGCCCGGCCGGCT) corre-" should read -- ATGGACCCCTACAAAGGTGCCCGGCCGGCT (SEQ ID NO: 20) corre- --.
Line 41, "type probe TGCTCCTG̲GACCTTC;" should read -- type probe TGCTCCTG̲GACCTTC (SEQ ID NO: 21);--; and
Line 42, "probe, TGCTCCTA̲GACCTTC)." should read -- probe, TGCTCCTA̲GACCTTC (SEQ ID NO: 22)). --.

Column 29,
Line 36, "seament" should read -- segment --.

Column 35,
Line 11, "GDP-fucose:μ-D-N-" should read -- GDP-fucose:β-D-N- --.

Signed and Sealed this

Fifteenth Day of January, 2002

Attest:

Attesting Officer

JAMES E. ROGAN
*Director of the United States Patent and Trademark Office*